Figure 1:
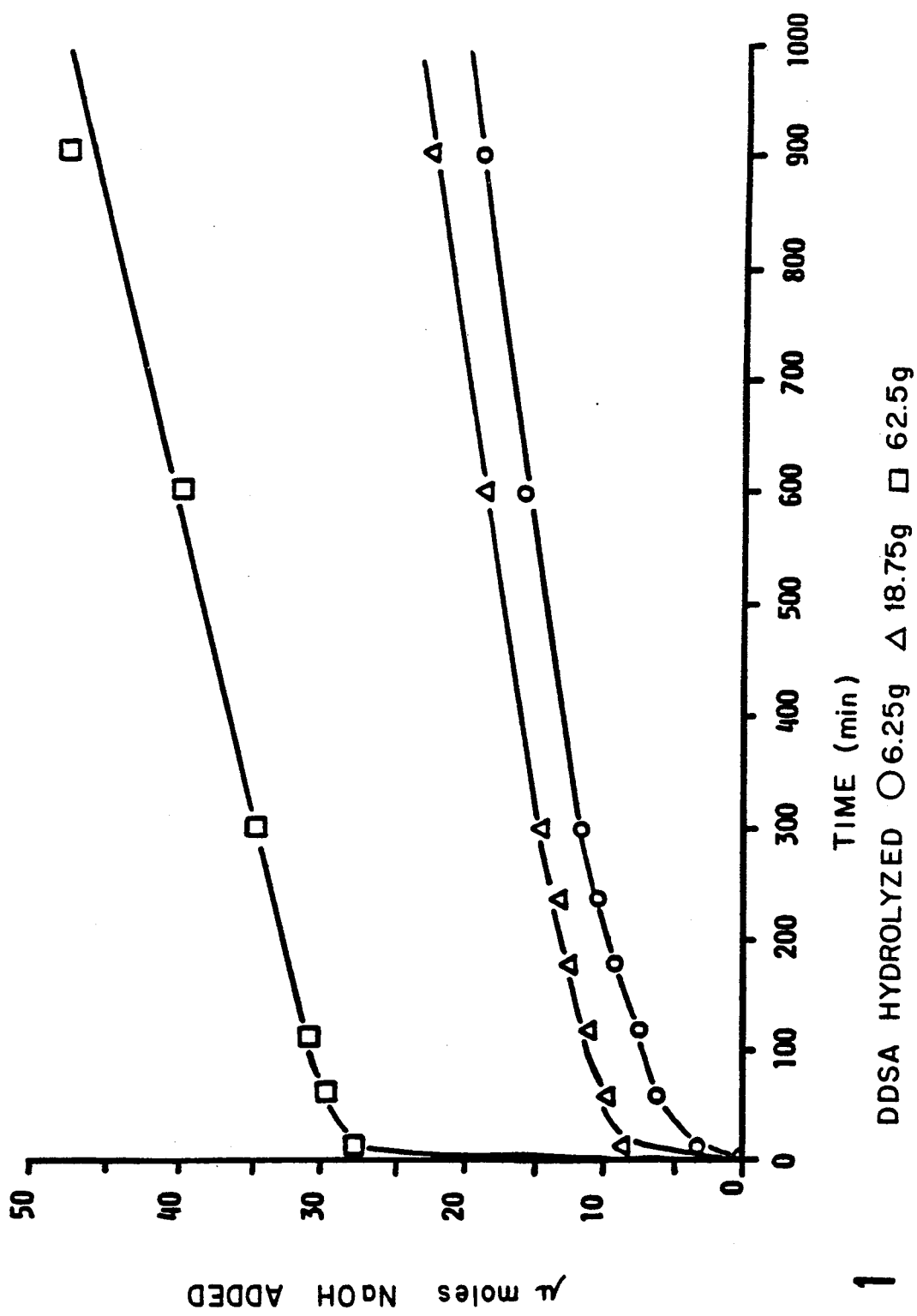

United States Patent [19]
Nestaas et al.

[11] Patent Number: 5,212,235
[45] Date of Patent: May 18, 1993

[54] HYDROPHOBICALLY MODIFIED PROTEINS

[75] Inventors: Eirik Nestaas, Trondheim, Norway; Kevin R. Hrebenar, Jacksonville, Fla.; Jerome M. Lewis; George M. Whitesides, both of Newton, Mass.

[73] Assignee: Emulsan Biotechnologies, Inc., New York, N.Y.

[21] Appl. No.: 634,369

[22] Filed: Dec. 27, 1990

Related U.S. Application Data

[63] Continuation of Ser. No. 22,443, Mar. 3, 1987, abandoned.

[51] Int. Cl.$^5$ ............................. C07K 1/12; C08H 1/06
[52] U.S. Cl. ................................... 525/54.1; 530/343; 530/354; 530/356
[58] Field of Search ...................... 525/54.1; 424/70; 530/343, 354, 356

[56] References Cited

U.S. PATENT DOCUMENTS

| | | | |
|---|---|---|---|
| 3,619,206 | 11/1971 | Lawrence et al. | 426/605 |
| 4,168,262 | 9/1979 | Kinsella et al. | 530/824 |
| 4,195,077 | 3/1980 | Marsh et al. | 424/70 |
| 4,705,682 | 11/1987 | Moeller et al. | 424/70 |

FOREIGN PATENT DOCUMENTS 1200419  7/1970  United Kingdom.

OTHER PUBLICATIONS

Allinger et al, Organic Chemistry, Worth Publishers, Inc. N.Y., N.Y. 1971, pp. 756–757.
Shetty, et al. "Isolation of Yeast Protein with Reduced Nucleic Acid Level Using Reversible Acylating Reagents: Some Properties of the Isolated Protein" J. Agric. Food Chem. 1982, 30, 1166–1171.
K. Pearce et al., "Emulsifying Properties of Proteins: Evaluation of a Turbiedimetric Technique", J. Agr. Food Chem. 1978, 26(3), 716–723.
E. Childs et al. "Functional Properties of Acylated Gladless Cottonseed Flour", J. Food Sci. 1976, 41, 713–714.
K. Franzen et al., "Functional Properties of Succinylated and Acetylated Soy Protein", J. of Agri. Food Chem. 1976, 24(4), 788–795.
H. McElwain et al., "Some Functional Properties of Succinylated Single Cell Protein Concentrate", J. Milk Food Technol. 1975, 38(9), 521–526.
Li-Fu Chen et al., "Some Functional Properties of Succinylated Proteins From Fish Protein Concentrate", J. Milk Food Technol. 1975, 38(2), 89–93.
H. Groniger, "Preparation and Properties of Succinylated Fish Myofibrillar Protein", J. of Agri. Food Chem. 1973, 21(6), 978–981.
L. K. Creamer et al., "Preparation and Evaluation of Some Acid Soluble Casein Derivatives", New Zealand J. of Dairy Sci. and Technol. 1971, 107–11.
S. Krishna Gandhi et al., "Chemical Modification of Egg White with 3,3–Dimethylglutaric Anhydride", J. of Food Sci. 1968, 33, 163–169.

*Primary Examiner*—Nathan M. Nutter
*Attorney, Agent, or Firm*—Pennie & Edmonds

[57] ABSTRACT

This invention relates to the production of oil-in-water emulsifiers and emulsion stabilizers. More particularly, this invention relates to methods for the production of novel hydrophobically modified proteins which may be used as emulsifiers or to stabilize emulsions.

This invention also relates to products incorporating these hydrophobically modified protein emulsifiers and emulsion stabilizers. These compounds may be used in many applications such as paints, dyes and cosmetics.

3 Claims, 32 Drawing Sheets

HYDROPHOBICALLY MODIFIED PROTEINS

This is a continuation of application Ser. No. 07/022,443, filed Mar. 3, 1987 and now abandoned.

1. INTRODUCTION

This invention relates to the production of oil-in-water emulsion stabilizers. More particularly, this invention relates to methods for the production of novel modified proteins which may be used to stabilize emulsions. Proteins which are modified by this method are rendered significantly more surface active than they are in their natural state and may be used in a wide range of consumer product and industrial applications.

This invention also relates to the novel modified protein emulsion stabilizers themselves. These emulsion stabilizers are naturally white in color and, therefore, may be used in many applications which cannot tolerate a colored compound, such as paints, dyes and cosmetics. Moreover, the starting materials used to create these novel compounds are safe, inexpensive and readily available.

2. BACKGROUND OF THE INVENTION

2.1. Alkenylsuccinic Anhydrides and DDSA

Dodecenylsuccinic anhydride ("DDSA") is often employed as a readily-available member of a class of long-chain (usually $C_6$ to $C_{30}$) alkenyl succinic anhydrides ("ASA's") (shorter chain members being alkyl succinic anhydrides). These compounds may also be alternatively referred to herein as hydrophobic, lipid or fatty acid anhydrides and, generally, as derivatives of succinic anhydride. The chemical characteristics of ASA's are derived from their reactions with nucleophiles (RXH) to give a compound of the following type:

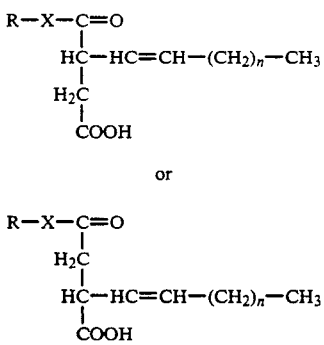

The combination of the alkenyl (or alkyl) chain and the polar and carboxylic acid moiety give such compounds both a hydrophobic and hydrophilic nature.

2.2. Anti-Corrosion Compositions

ASA's have been components in a number of patented rust and corrosion inhibitors. The compound formed by reaction of aliphatic hydroxy acids with ASA's has been added as an anti-corrosion additive to fuels [U.S. Pat. No. 4,148,605]. Generally, ASA's are mentioned as anticorrosive components in fuel [U.S. Pat. No. 3,615,290 or European Patent Application 83.3004404, 1983]. A mixture of an ASA and partially polymerized linoleic acid has been used as a lubricant additive [U.S. Pat. No. 3,208,945]. It has also been claimed that better results are obtained with a combination of polymerized unsaturated aliphatic acids and alkenylsuccinic acids [U.S Pat. No. 4,214,876]. A lithium salt of a hydrocarbon substituted acid or anhydride has been used as a rust inhibitor [U.S. Pat. No. 3,634,240].

2.3. Reactions with Polyesters

ASA's have long been used as curing agents for epoxy resins [6 Encyclopedia of Polymer Science and Technology 234 (1967); 9 Encyclopedia of Chemical Technology 280 (3 ed.) 1980]. An epoxy resin formed from reaction of a hydroxy-terminated polyester and a mixture of a tricarboxylic acid anhydride and an ASA has been used as a coating. A metal coating with this resin is said to experience "substantially reduced cratering" over compositions lacking ASA's [U.S. Pat. No. 3,650,997]. Resins including ASA's have reduced melt viscosity and better dye receptivity over those not including ASA's [U.S. Pat. No. 3,542,737]. In addition, polyester has been obtained by condensation of polyester glycol, a polyhydrine alcohol, and an ASA. The composition can be used at a concentration of 5-100 ppm to break up water-in-oil emulsions [U.K. Patent Application No. 7841858]. ASA's have also been used as compatibilizing agents, reacting with hydroxy-terminal polyesters to facilitate blending of the polyesters with rubber [European Patent Application 84.6300424].

2.4. Reactions with Wool

Wool has been subjected to anhydrous treatment with an acid anhydride (preferably an ASA such as DDSA) in the presence of cresol [U.S Pat. No. 3,332,733]. The product wool has a decreased tendency to shrink when washed with water, and has increased resistance to acids. The patent does not discuss the exact nature or the chemical reaction between the wool and anhydride.

2.5. Cyclic Anhydrides and Proteins

2.5.1 General Effects on Physical Properties

Cyclic anhydrides react with the terminal amino functions of lysines in polypeptides, to form an imide linkage and a terminal carboxylic acid. Anhydrides also react with other amino acid nucleophilic side-chain functionalities, but generally at a lesser rate. This transformation of a basic to an acidic terminus affects the interactions of the polypeptide both with itself and its environment, resulting in an altered tertiary structure, dissociation of subunits, and a decrease in the protein molecule's sedimentation coefficient. Reactions with maleic anhydrides tend to be reversible (the diacid can be removed by treatment with mild aqueous acid) while succinic anhydride derivatives have been fond to be more stable (such that removal requires acid strength that also damages the protein) [Klapper and Klotz, *Acylation with Dicarboxylic Acid Anhydrides,* 25 Methods of Enzymology 531 (1972); Kinsella and Shetty, *Chemical Modification for Improving Functional Properties of Plant and Yeast Proteins,* 1979 A.C.S. Symp. Ser. 37].

In general, succinylation of proteins has led to dissociation/deaggregation, [Chu and Chun, "Microorganisms Detection Methods and the Separation of Agglutinized Microorganisms", European Patent Application No. 84301507.4 (1983)—pretreatment of specimens with succinic anhydride to prevent autoagglutination], and an increase in solubility, solution viscosity, waterholding, oil-holding, emulsifying, and emulsion stabilizing ability. The emulsifying activity (EA) of bovine serum albumin and yeast protein has also improved after succinylation. [Respectively, *Protein Stabilized Emulsions: Effects of Modification or the Emulsifying Activity of Bovine Serum Albumin in a Model System*, 29 J. Agric. Food Chem. 826, 830 (1981); Waniska, et al., and Kinsella in *Protein Structure and Functional Properties: Emulsification and Flavor Binding Effects*, 1982 A.C.S Symp. Ser. 301.]

2.5.2 Separation of Proteins and Nucleic Acids

Yeast protein has been subjected to succinylation to permit separation of the succinylated protein from the other cell materials and nucleic acids. [U.S. Pat. No. 4,168,262; Shetty and Kinsella, *Preparation of Yeast Protein Isolate with Low Nucleic Acid by Succinylation*, 44 J. Food Science 633 1979); Shetty and Kinsella, *Novel Method for the Reduction of Nucleic Acids in Yeasts Proteins*, 21 Biotech and Bioeng 329 (1979)]. The processes exploit (1) the general insolubility of the cell wall material, (2) the solubility of the succinylated protein at pH 8.5 (the pH of the succinylation reaction), (3) the insolubility of the succinylated protein at pH 4.2–4.5, and (4) the general (pH independent) solubility of nucleic acids. Thus, by succinylating and either acidifying/centrifuging or centrifuging/acidifying/centrifuging, the succinylated protein can be separated from nucleic acids either with or without the cell wall material. The method was also modified to use maleic anhydrides, thus facilitating removal of the diacid and recovery of underivatized protein [U.S. Pat. No. 4,348,479; Shetty and Kinsella, *Isolation of Yeast Protein with Reduced Nucleic Acid Level Using Reversible Acylating Reagents: Some Properties of the Isolated Proteins*, 30 J. Agric. Food Chem. 1166 (1982); Shetty and Kinsella, *Reversible Modification of Lysine: Separation of Proteins and Nucleic Acis in Yeast*, 1982 Adv. in Chem. Ser. 169].

2.5.3 Succinylation of Rennet

Rennet has been treated with maleic and succinic anhydrides [U.S. Pat. No. 4,362,818 and European Application No. 83103406.1 filed Apr. 1983]. While the treatment with maleic acid apparently increases the coagulating ability of the enzyme, succinic acid treatment is purportedly superior because of the irreversibility of the reaction and the poisonous effects of released maleic acid.

2.5.4 Succinylation Reactions with Proteins and Emulsification Properties

Succinylation reactions with proteins have been described as affecting the emulsification properties of the protein [Kinsella, supra., 1982; Waniska et al., supra.; Kinsella and Shetty; supra.]. The succinylation-modified proteins have been used in food products. Proteins modified by this type of reaction, which typically utilizes succinic anhydride, have been often found to have altered properties relating to their emulsifying activity. The emulsifying activity level after succinylation was unpredictable and it could either be increased or decreased depending on a variety of factors. The use of alkenyl or alkyl succinic anhydrides to affect or otherwise enhance the emulsification properties of a protein is absent from the art.

In this context, it is an object of the present invention to provide such novel succinylated proteins which have enhanced emulsification and emulsion stabilization properties and methods for selectively producing them along with novel products incorporating such modified proteins. To our knowledge, prior to this invention, alkenyl or alkyl succinylated proteins have not been utilized as emulsifiers or emulsion stabilizers nor have proteins in solution been reacted with these succinic anhydride derivatives.

3. Summary of the Invention

Covalently attached protein-lipid or fatty acid compounds of the present invention, show remarkable abilities to stabilize oil-in-water emulsions. The properties of this type of compound enables their use with different oils by changing both the ratio of the fatty acid to protein, the type of protein or the structure of the lipid anhydride (i.e. the anhydrides) alkenylsuccinic anhydrides or fatty acid employed. The compounds are naturally white in color which means that they can be used in many applications which cannot tolerate a colored compound, such as paints, dyes, cosmetics, etc.

Preliminary experiments indicate that in some cases compounds such as Casein:DDSA derivatives, need use only minimal preservatives (or none at all in other cases). This property simplifies the storage and use of these types of compounds. While the safety of this class of compounds such as (Casein:DDSA), is unknown at this time, they are probably very safe. One of the starting materials is a protein, such as a milk protein, and the others are fatty acid derivatives which are commonly used. In addition, the reactions are performed in water, hence the final product or side products cannot contain any anhydrides. The starting materials are also inexpensive and widely commercially available.

Prior to the present invention, applicants believe there has been no report of alkeny or alkyl succinylated proteins being useful as emulsion stabilizers or emulsifiers. This invention, therefore, provides an improved succinylated protein emulsifier or emulsion stabilizer. In addition, this invention provides a new process for producing these enhanced and novel emulsifiers and emulsion stabilizers. Essentially, the improved aspect of this invention is the use of a succinic anhydride derivative as a carrier to attach hydrophobic fatty acid (or lipid) tails onto proteins thus conferring significant emulsification or emulsion stabilization activity upon such modified proteins. The lipids may be of a non-biological origin (i.e. synthetic).

It is, therefore, an object of this invention to provide a variety of these modified proteins which may be utilized emulsifiers and emulsion stabilizers in various consumer and industrial products and compositions. The modified proteins may be utilized alone as an emulsifier or, in another preferred embodiment, in combination with other emulsifiers like the lipopolysaccharide, Emulsan [U.S. Pat. No. 4,395,391.

Another aspect of this invention is that the proteins to be reacted with the lipid anhydrides may be in either a pure or homogeneous form or in a fermentation broth containing whole and/or lysed cells. The fermentation broth may be derived from microbial, plant or animal cells. The microbial cells may also be producing, concurrently, another product, such as the emulsifier and emulsion stabilizer, Emulsan. Homogeneous peptide preparations may also be reacted according to processes discussed herein.

4. Brief Description of the Figures

Figure 2:
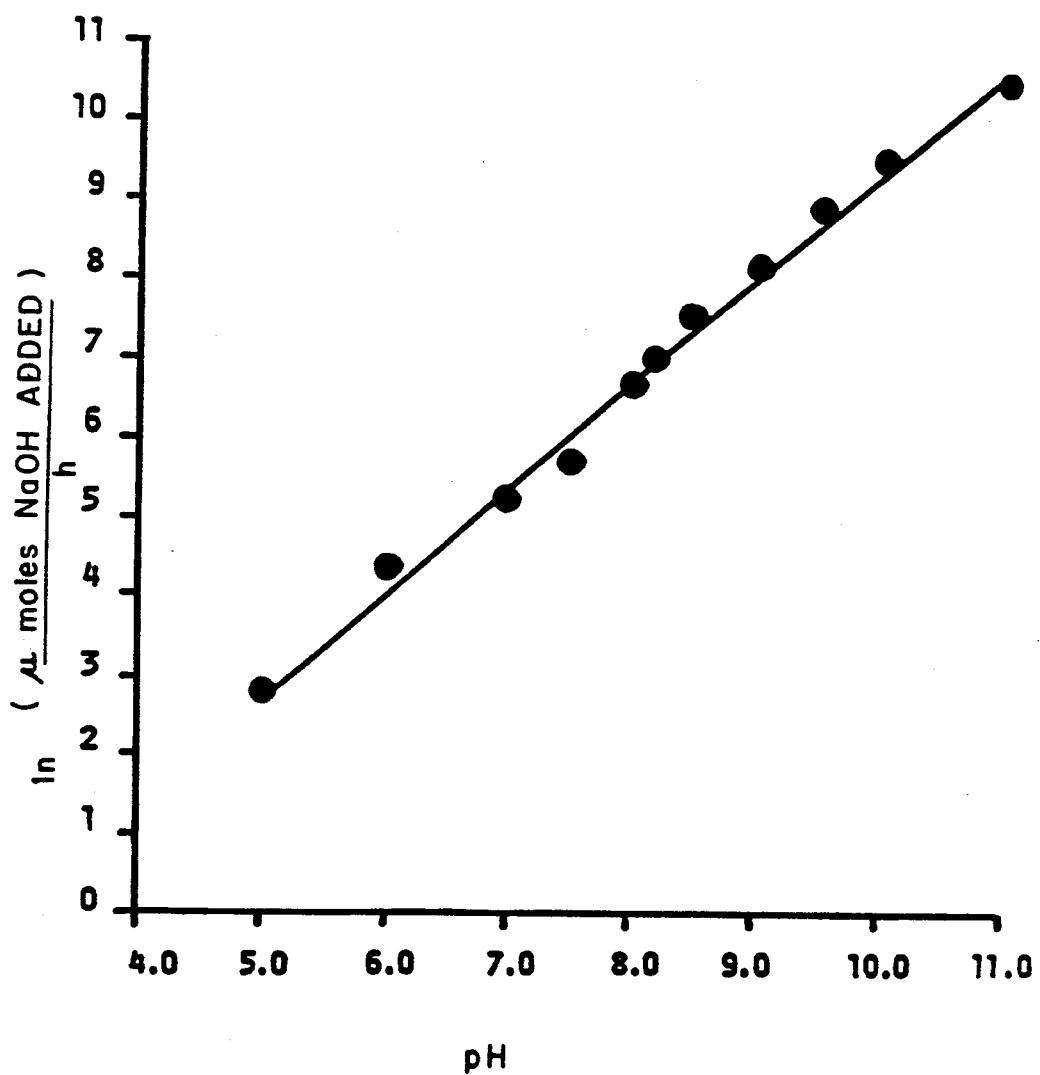
Figure 3:
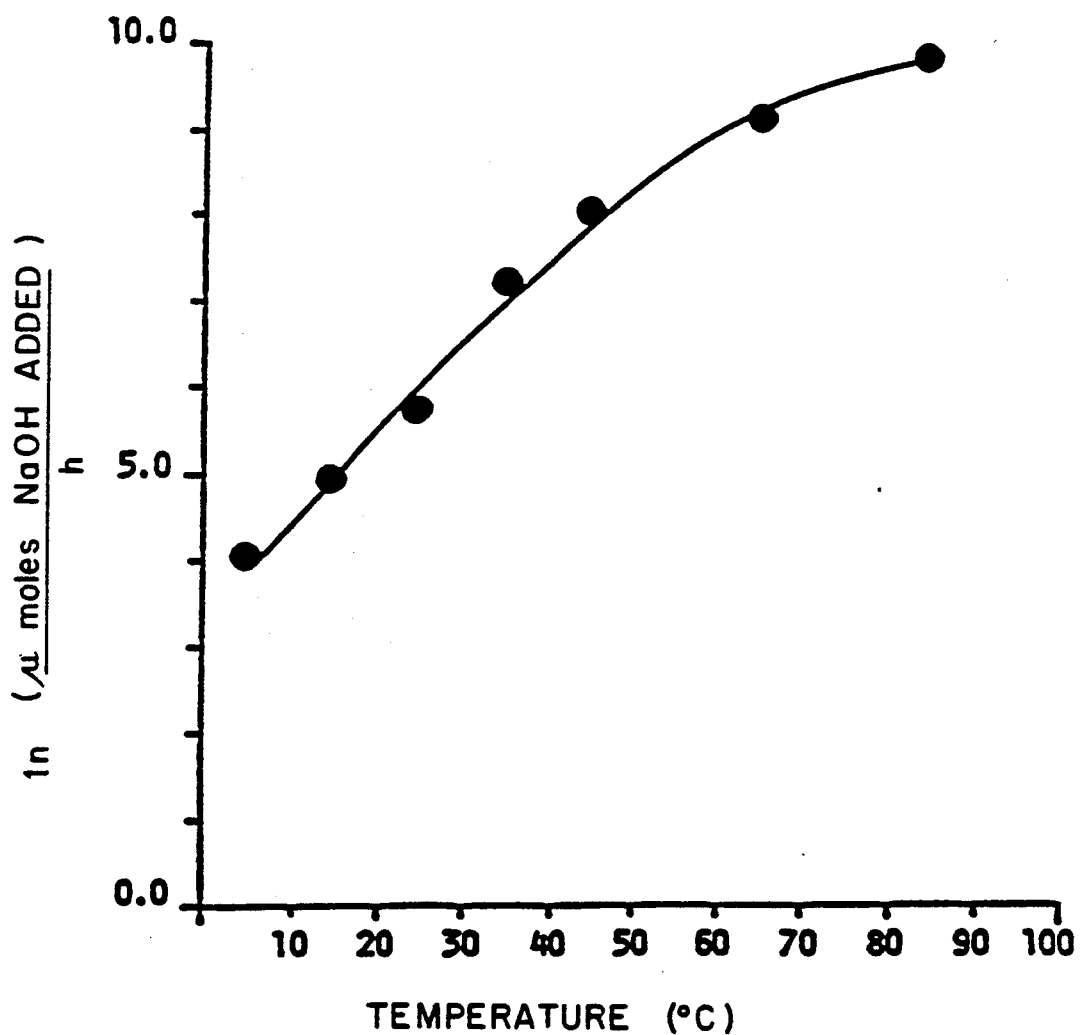
Figure 4:
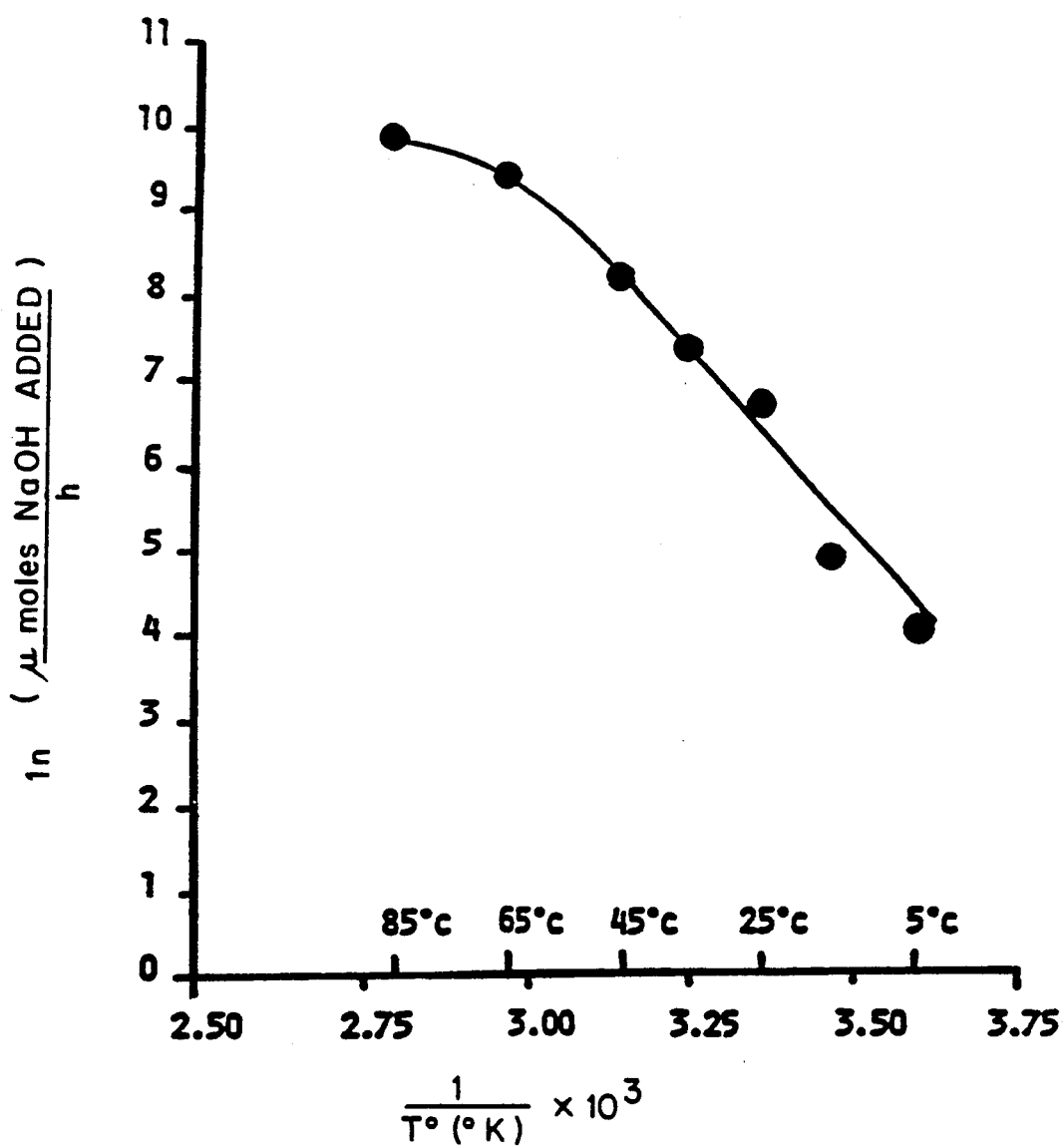
Figure 5:
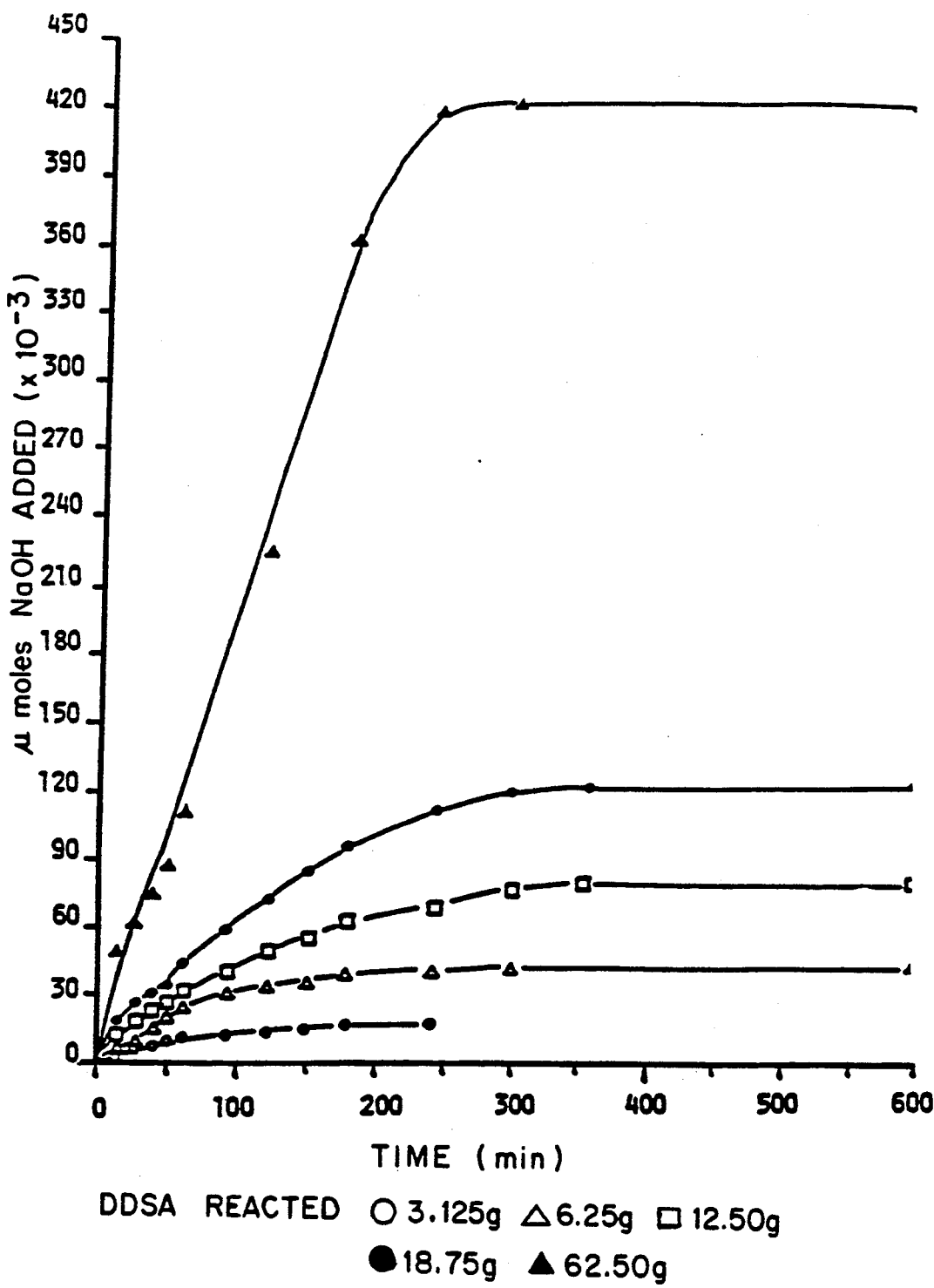
Figure 6:
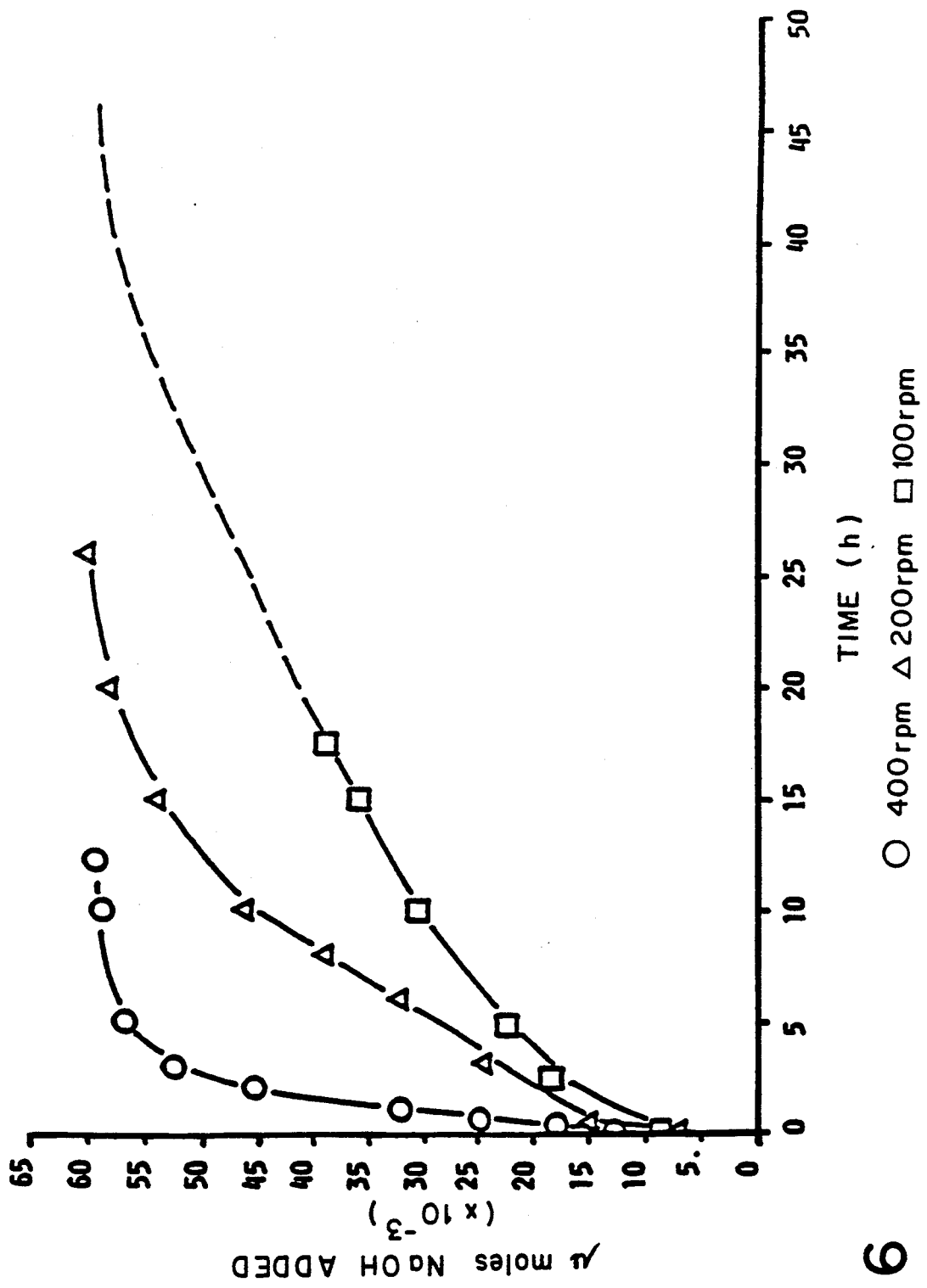
Figure 7:
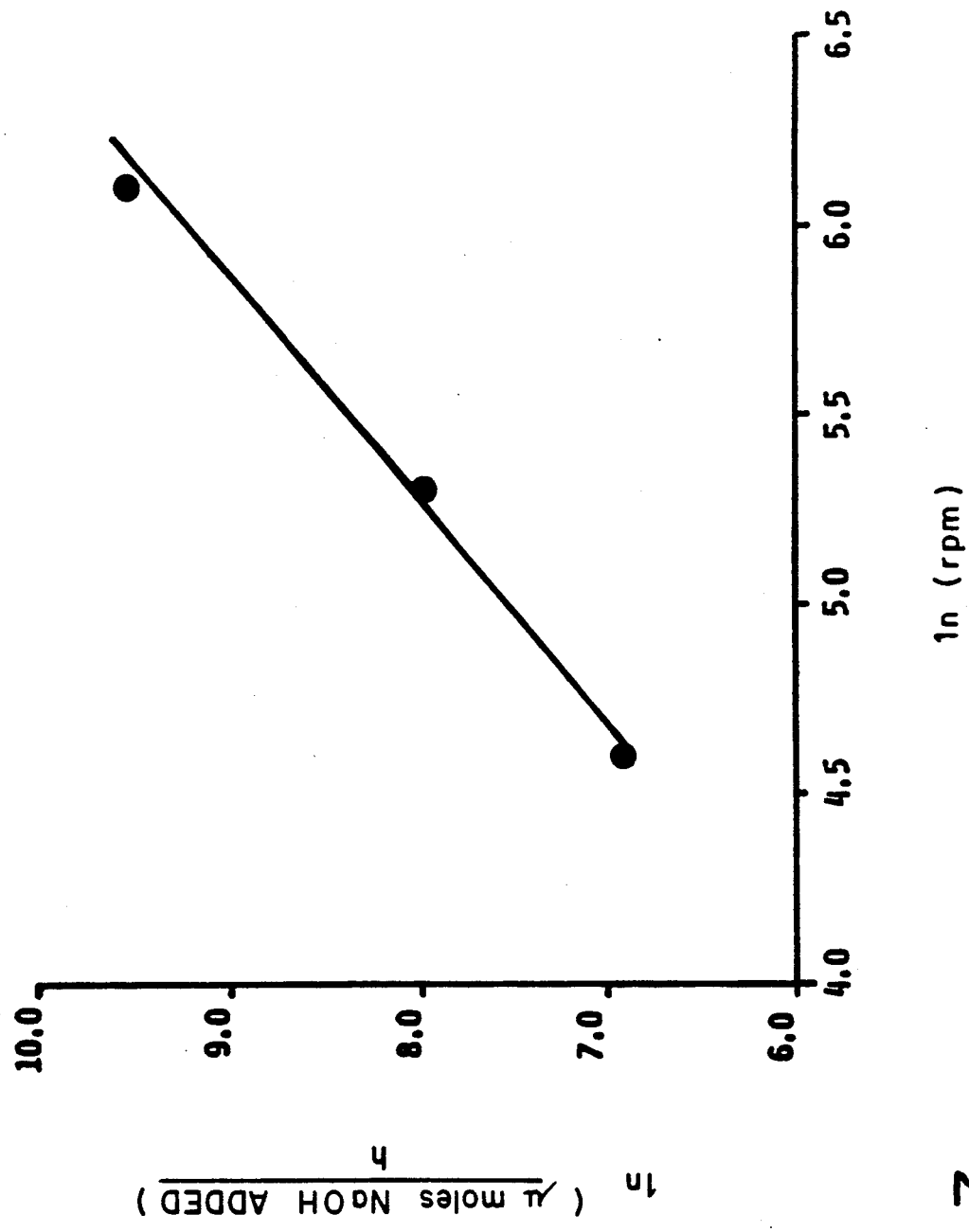
Figure 8:
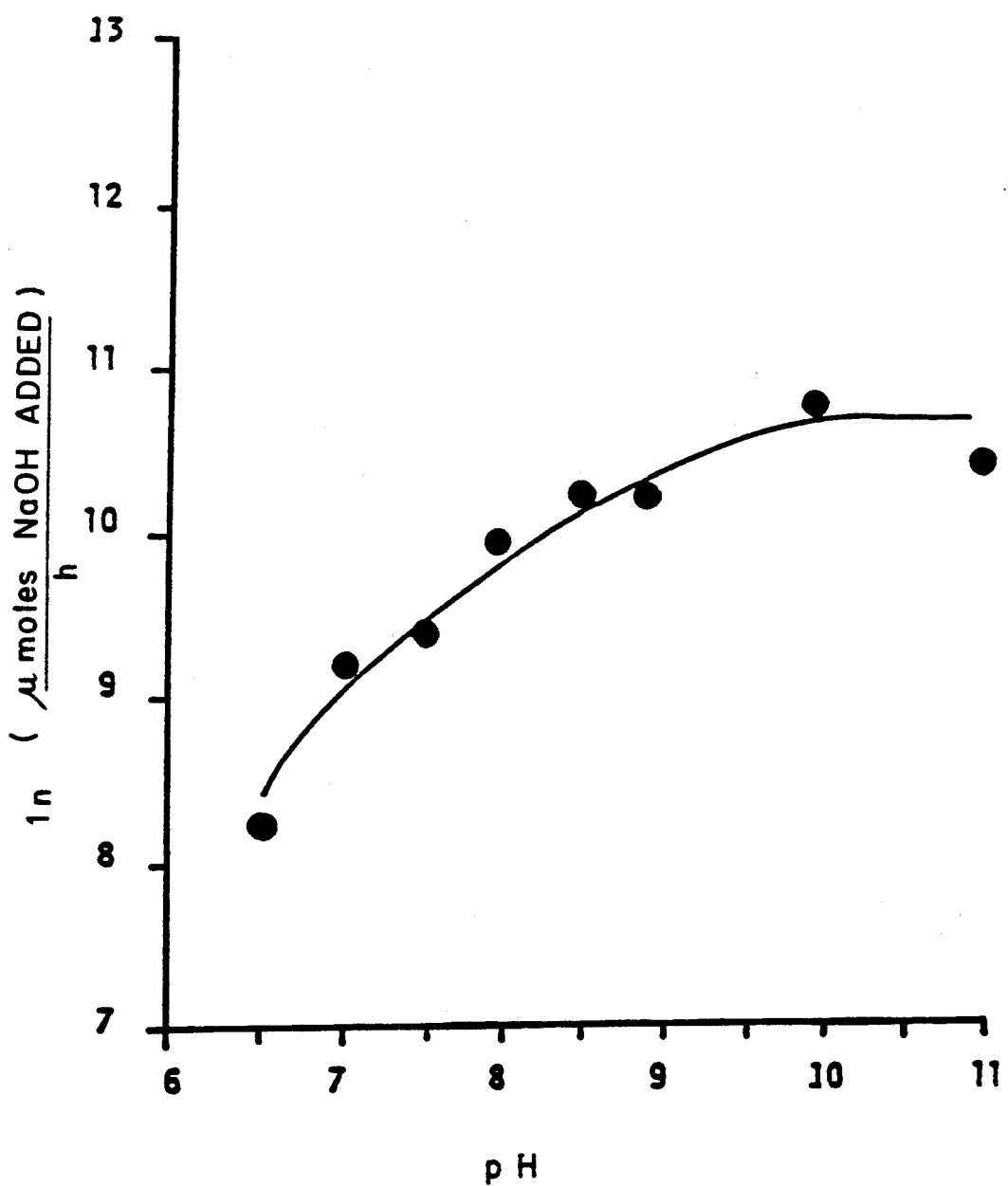
Figure 9:
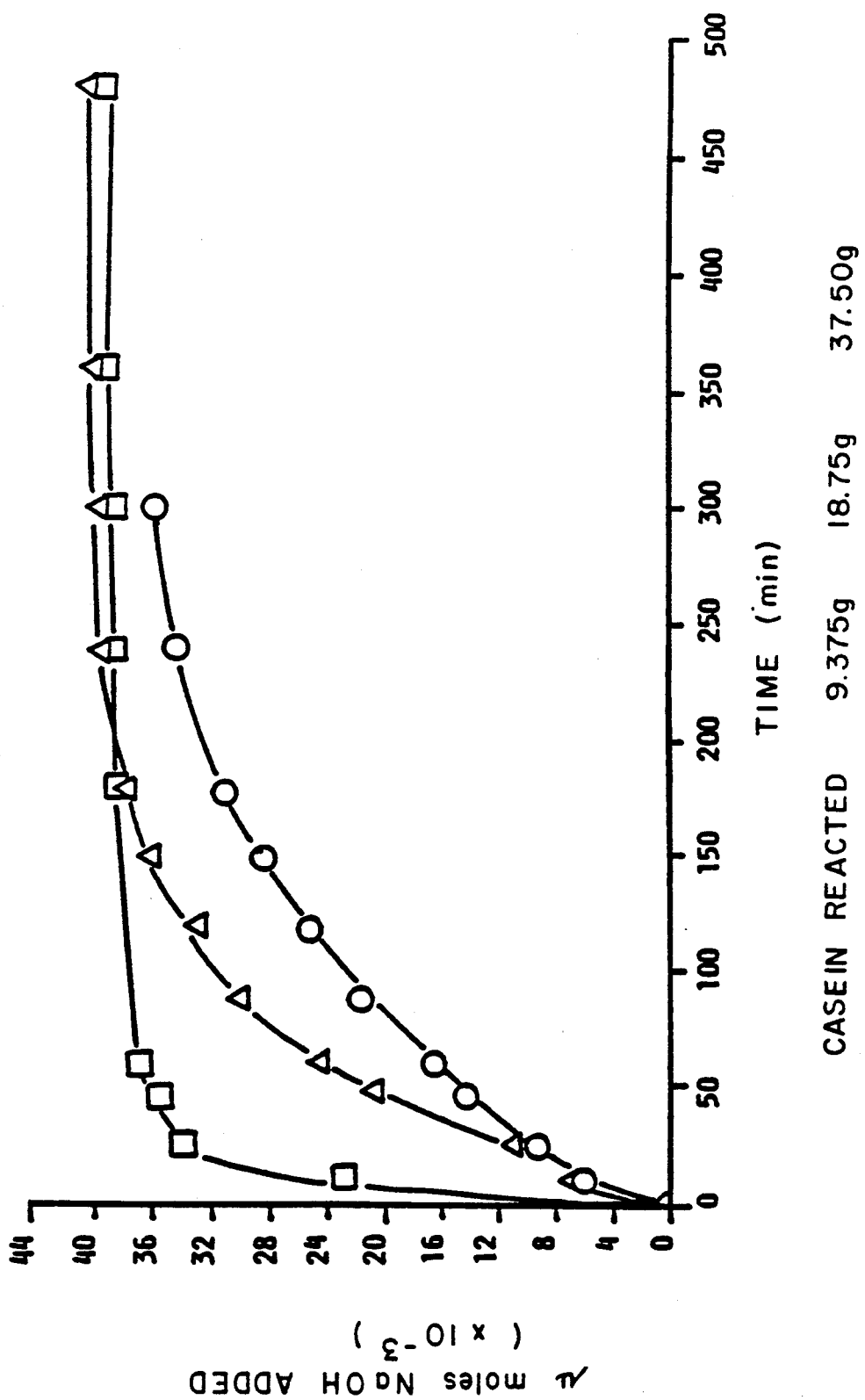
Figure 10:
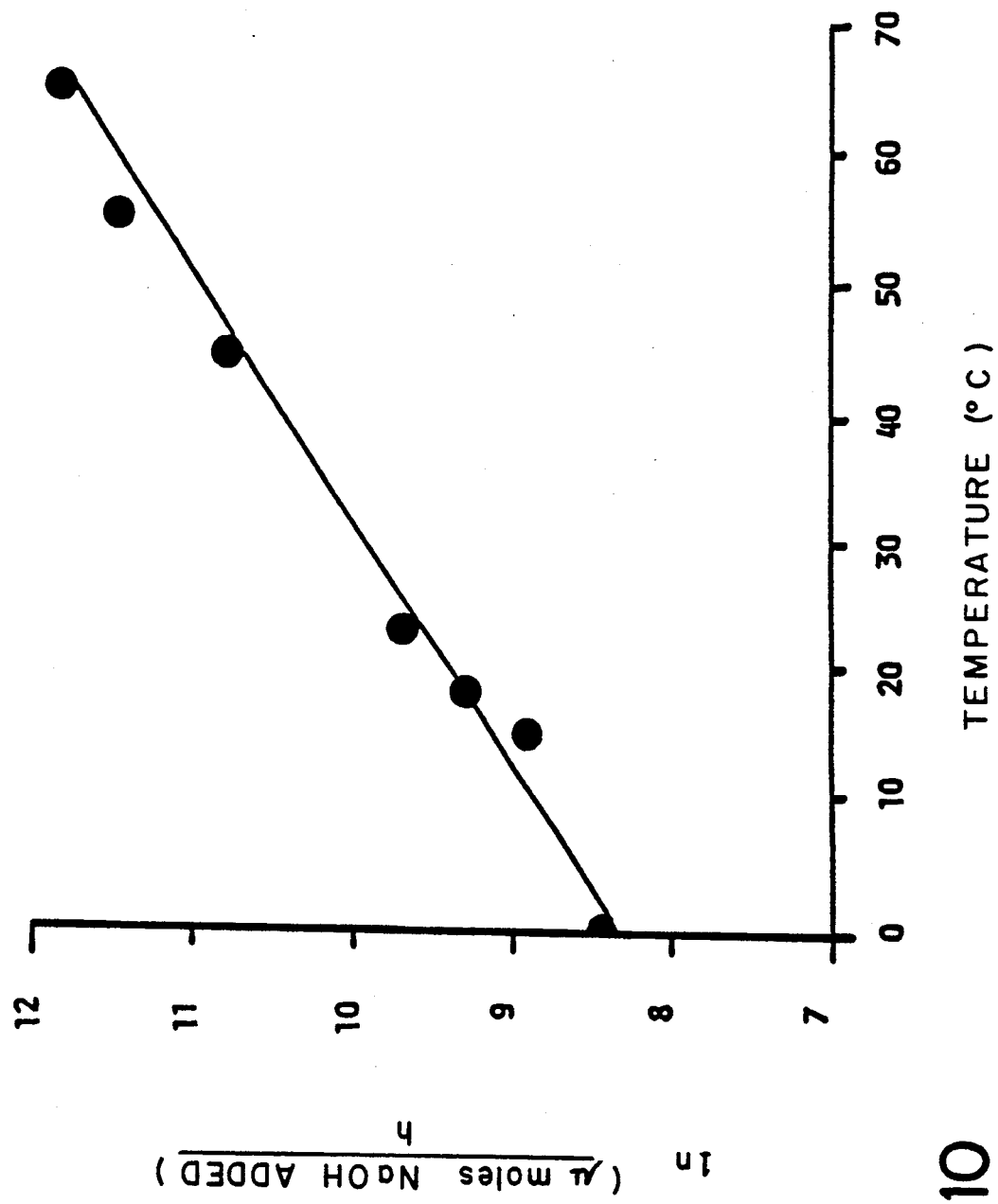
Figure 11:
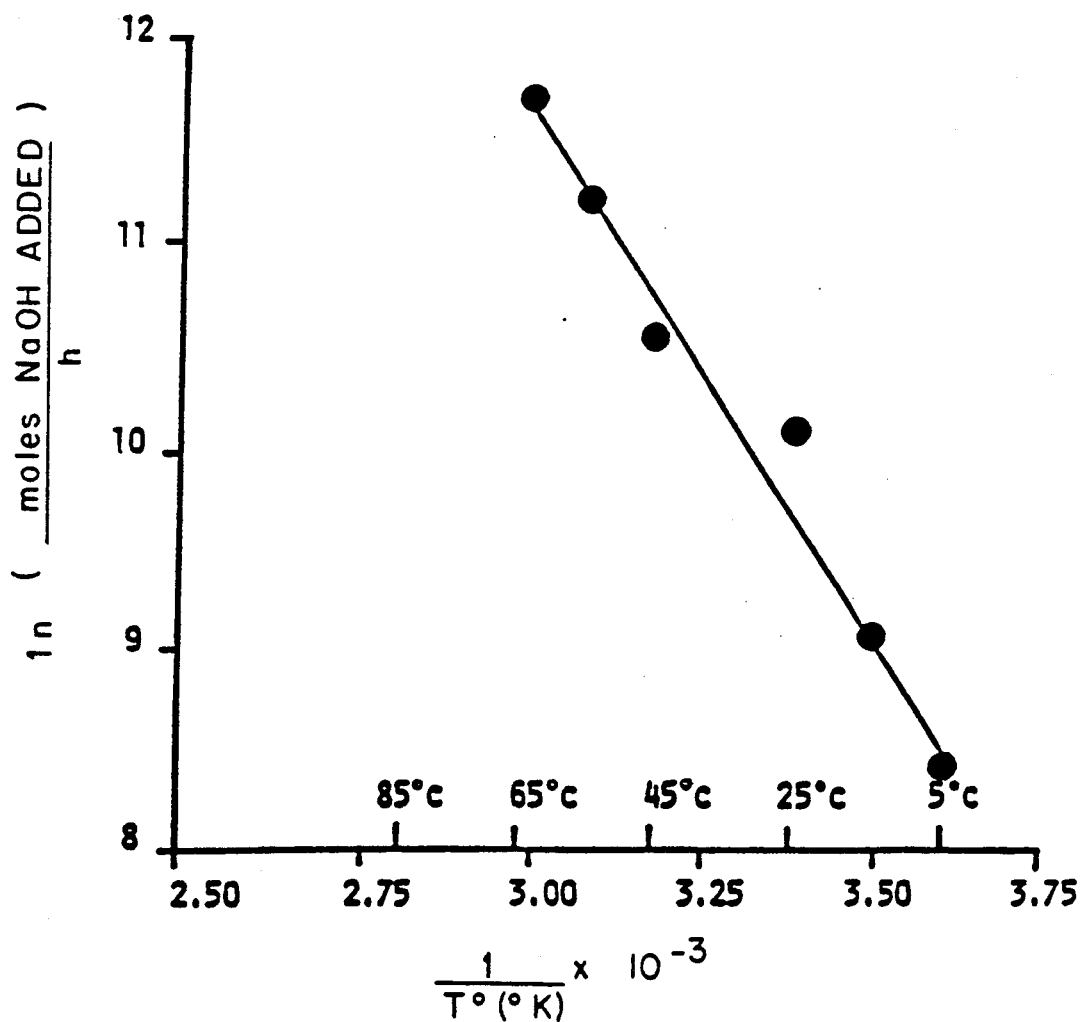
Figure 12:
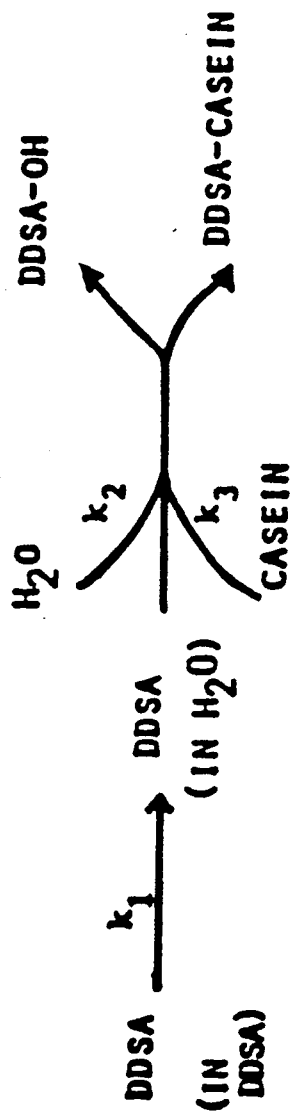
Figure 13:
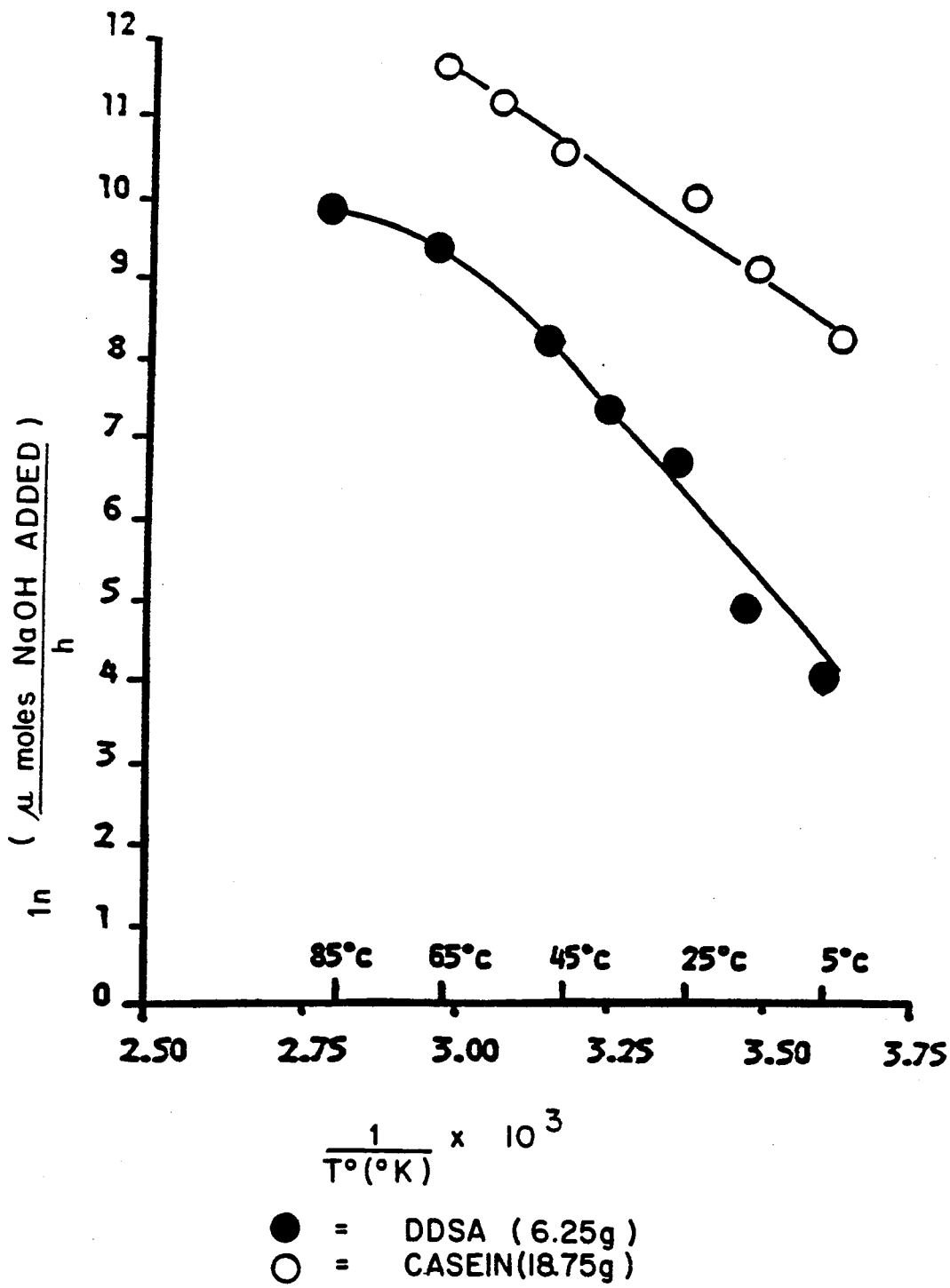
Figure 14:
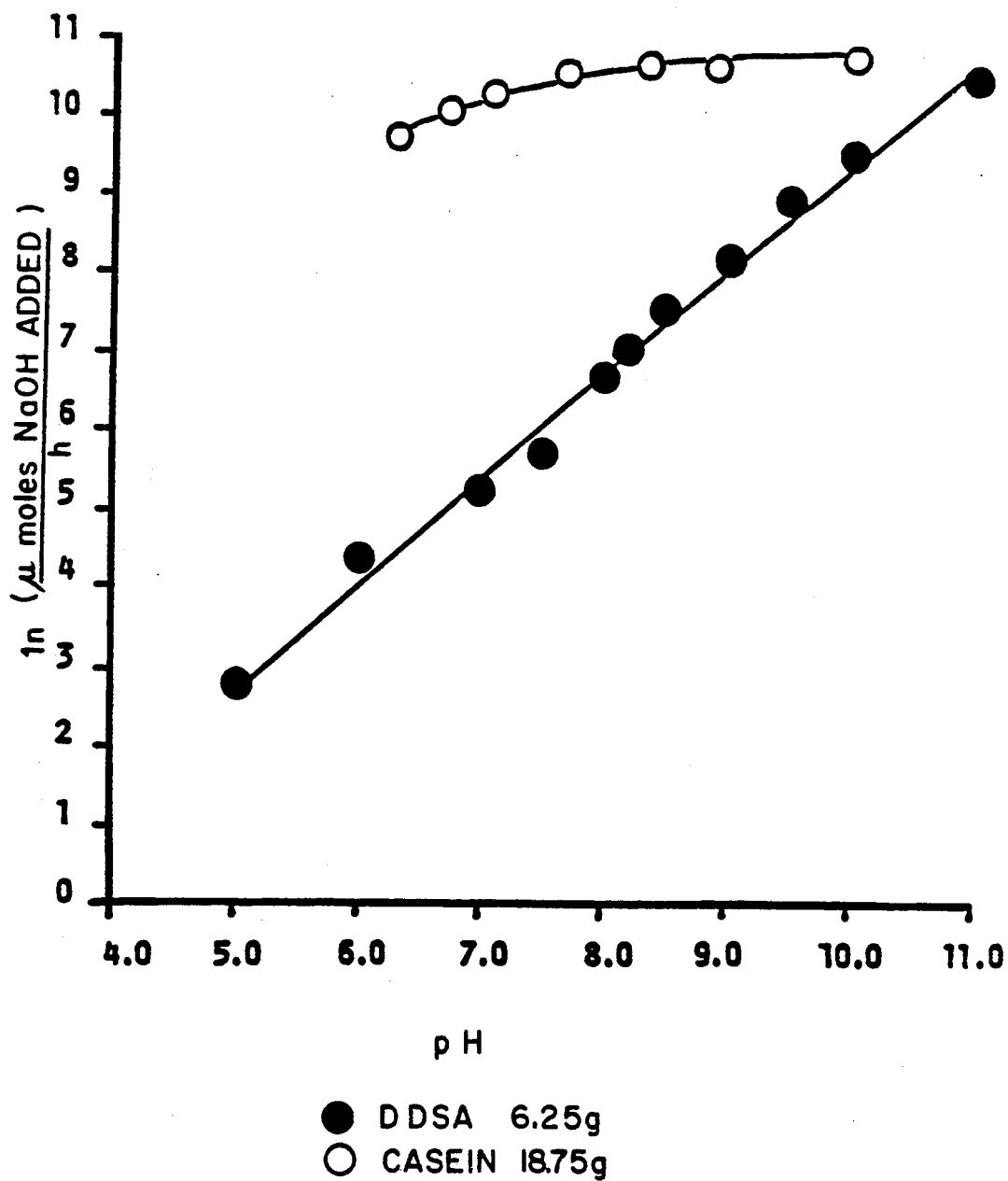
Figure 15:
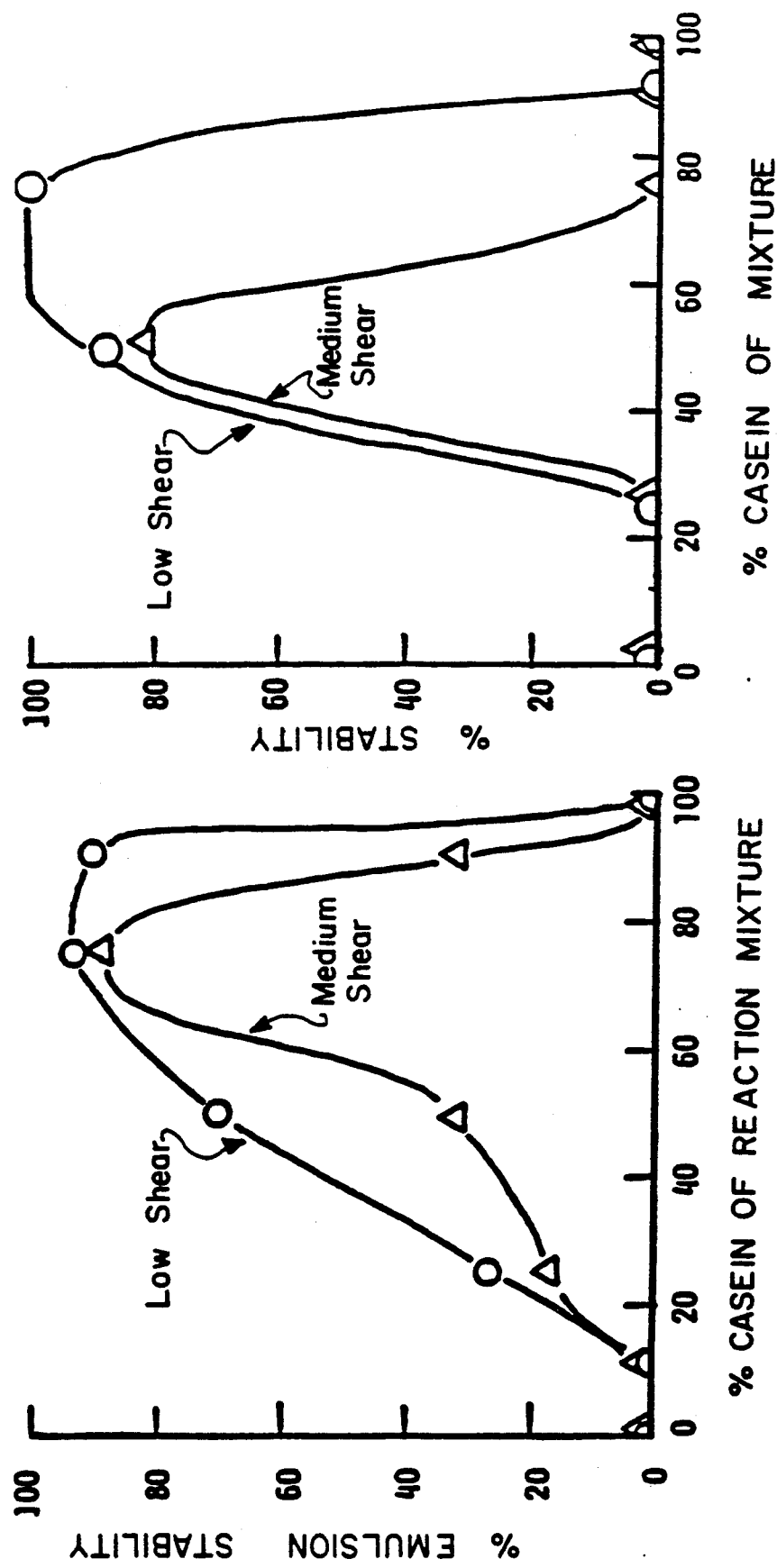
Figure 16:
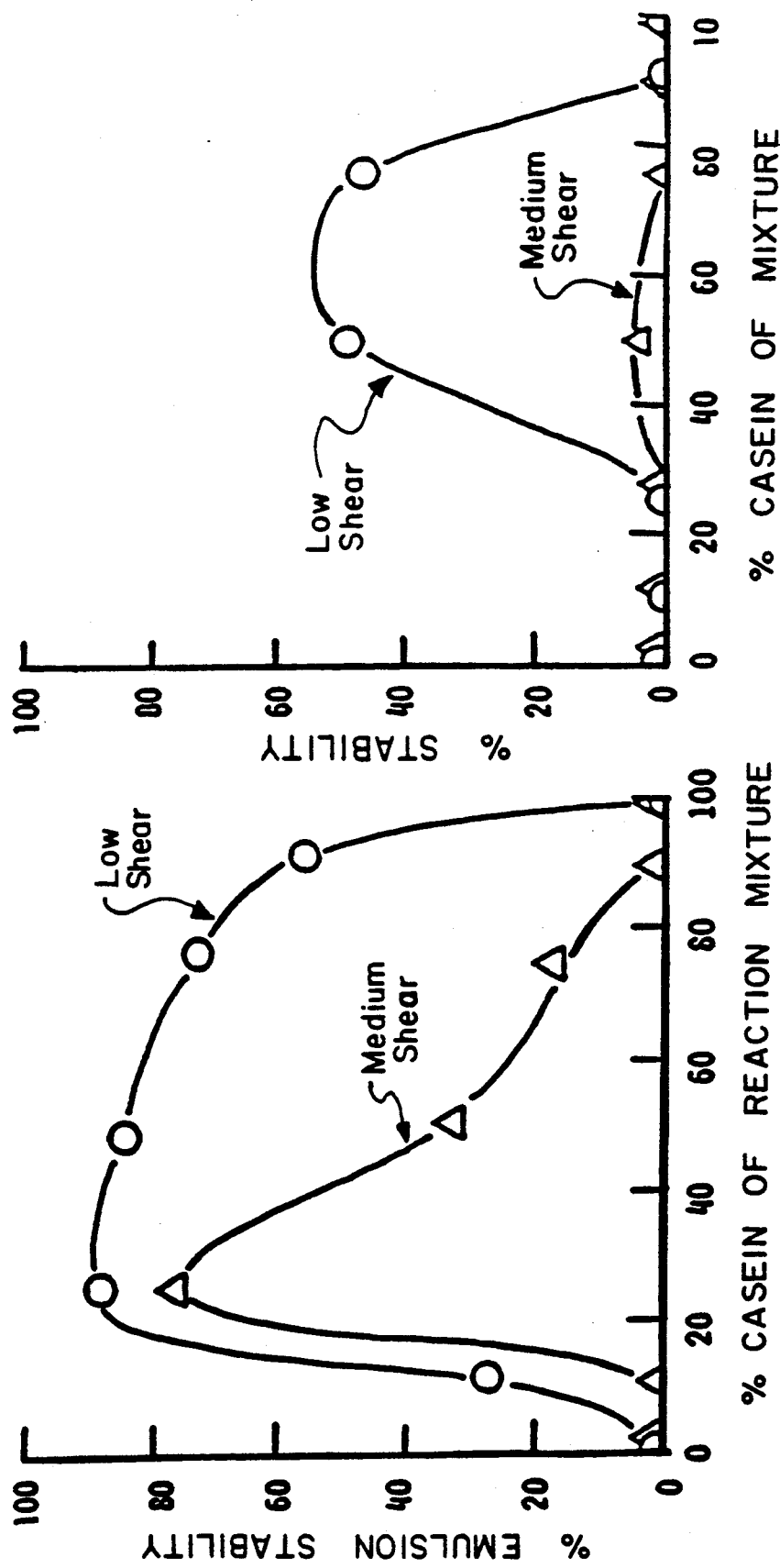
Figure 17:
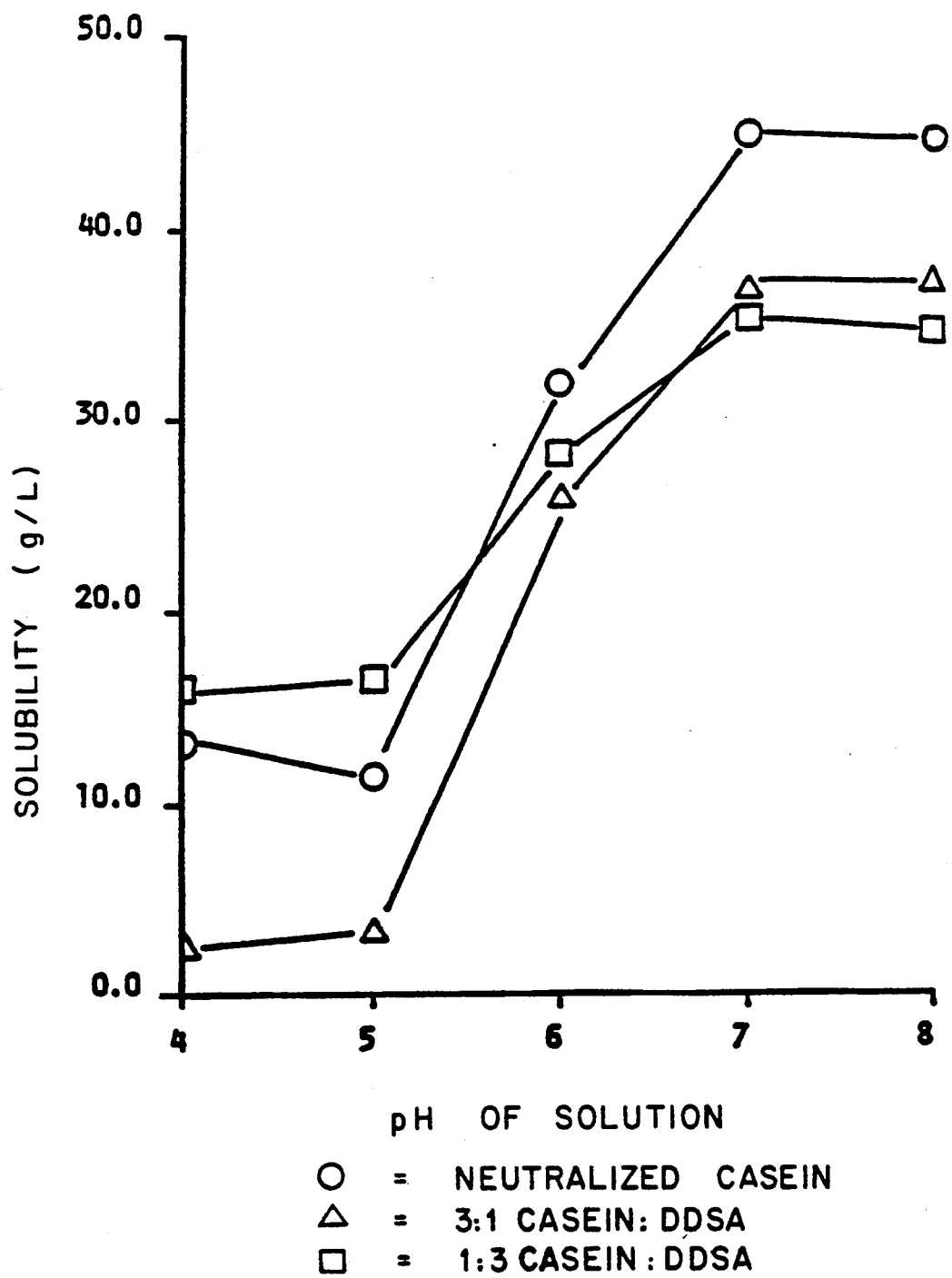
Figure 18:
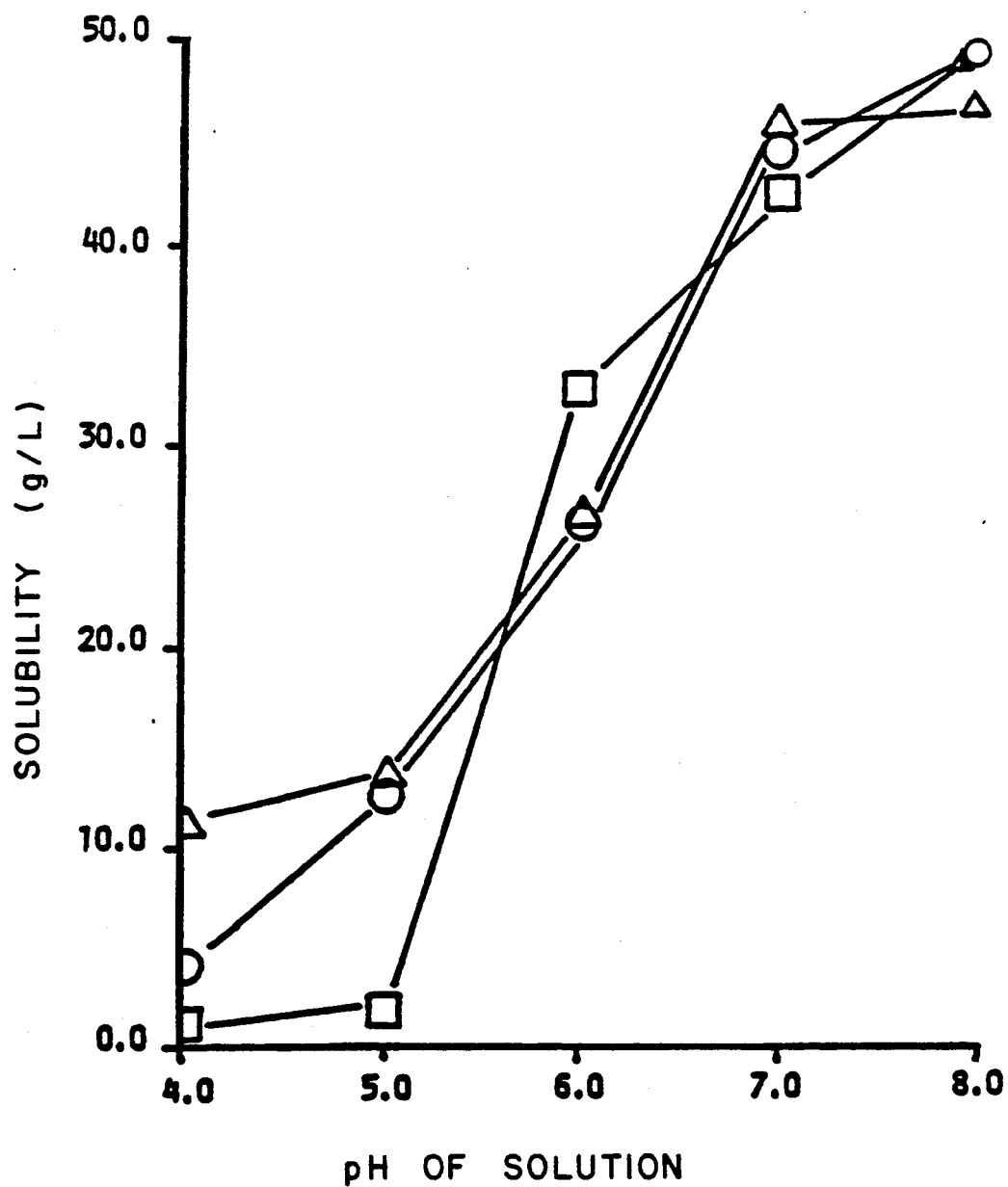
Figure 19:
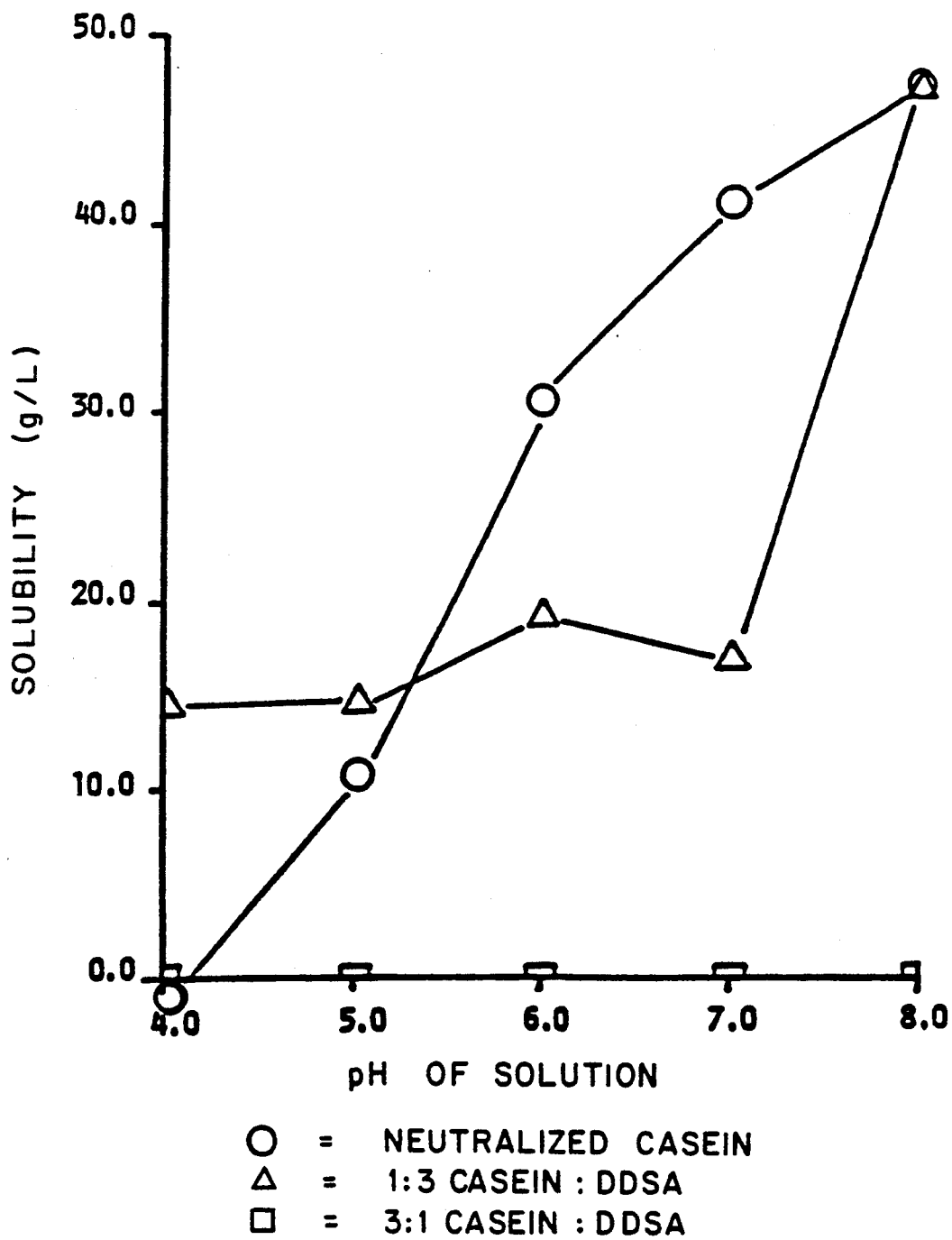
Figure 20:
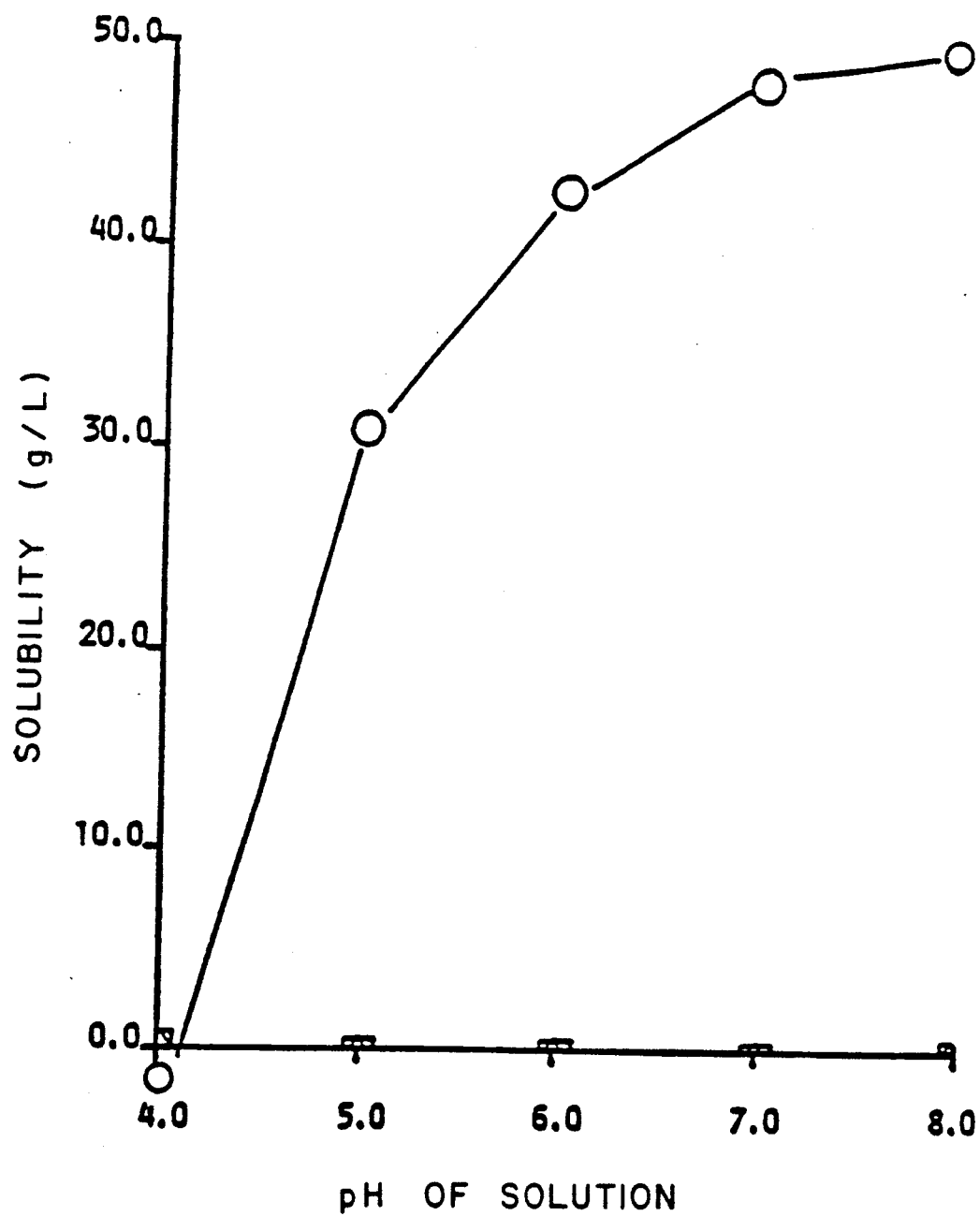
Figure 21:
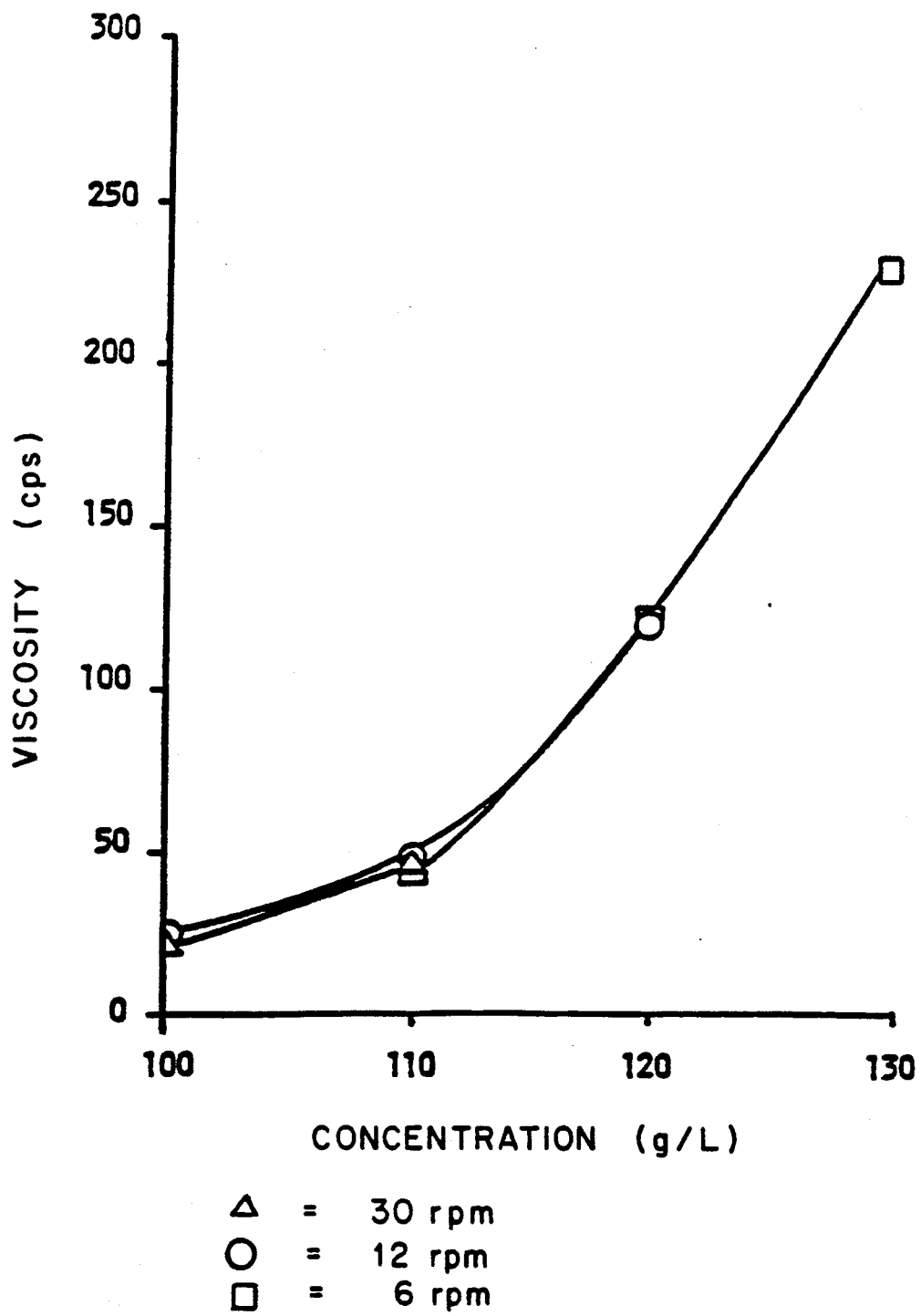
Figure 22:
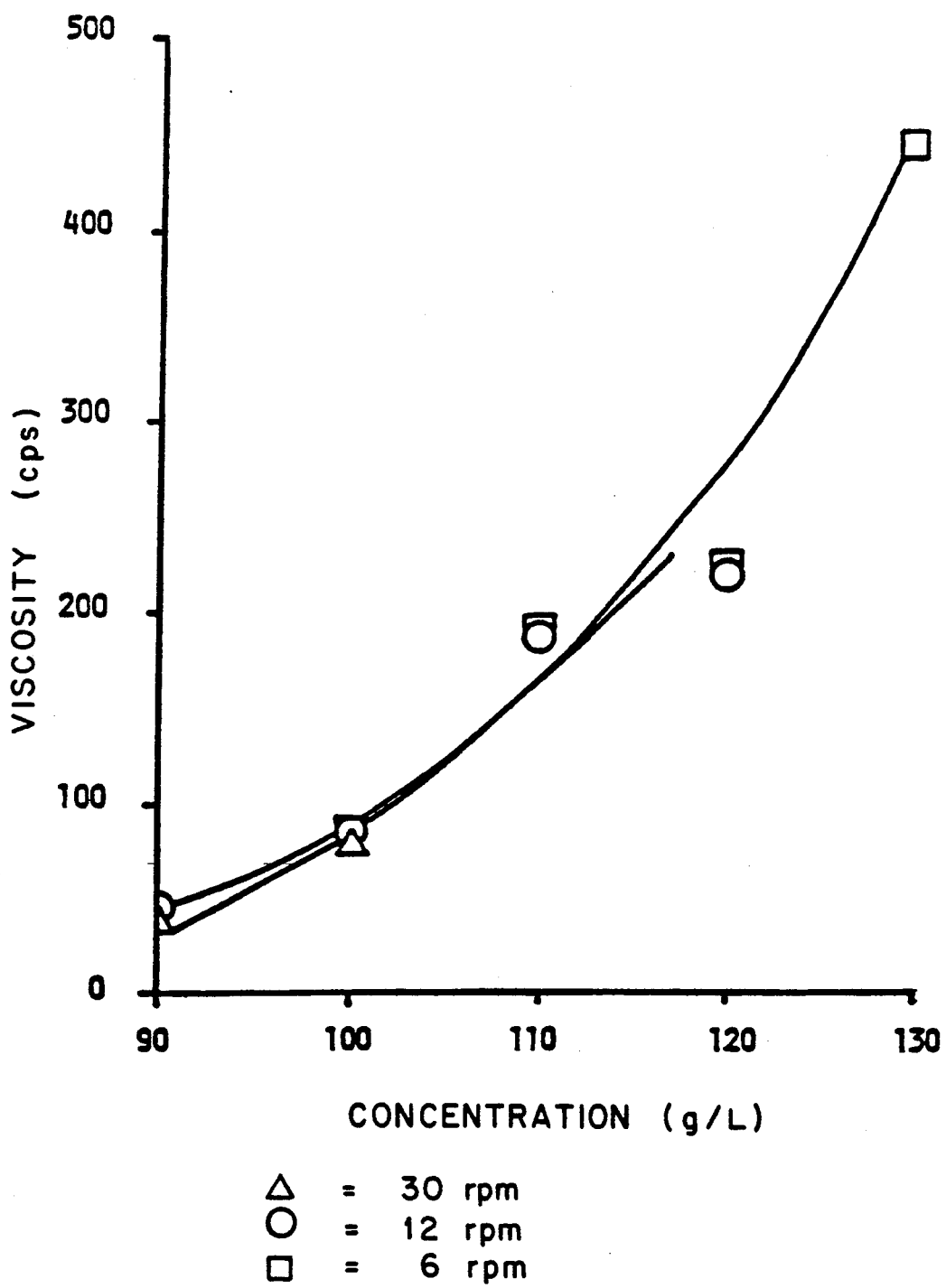
Figure 23:
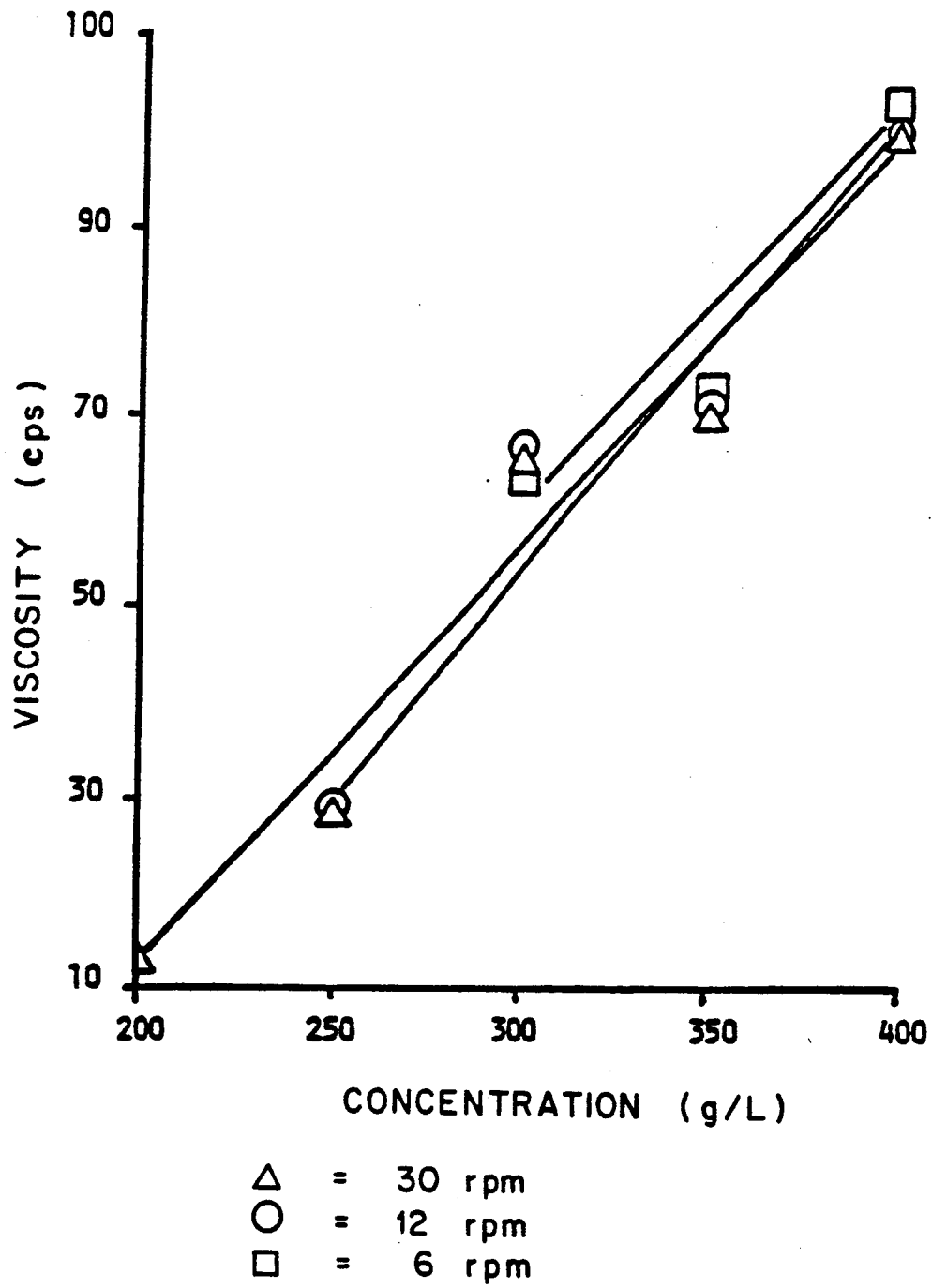
Figure 24:
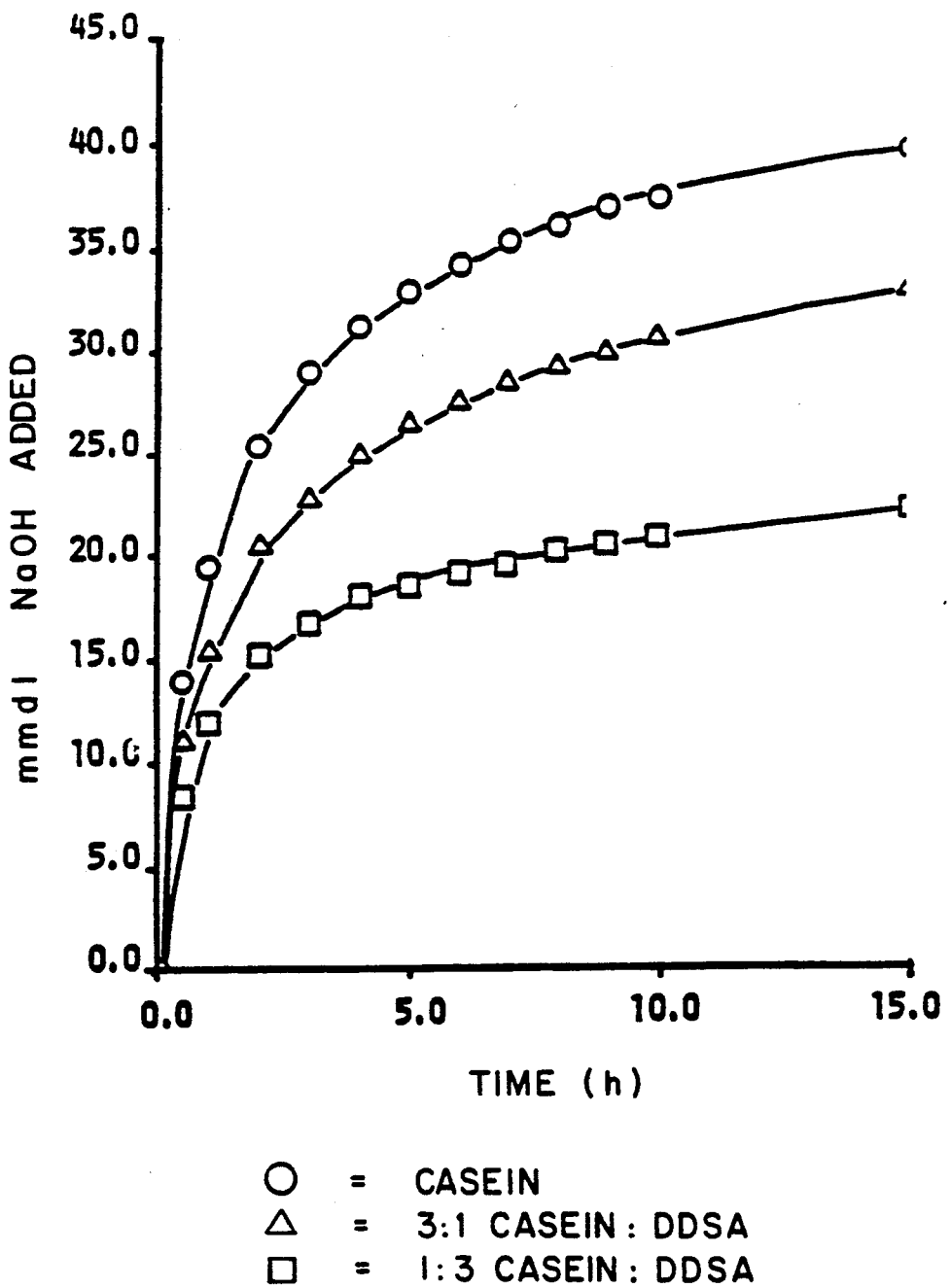
Figure 25:
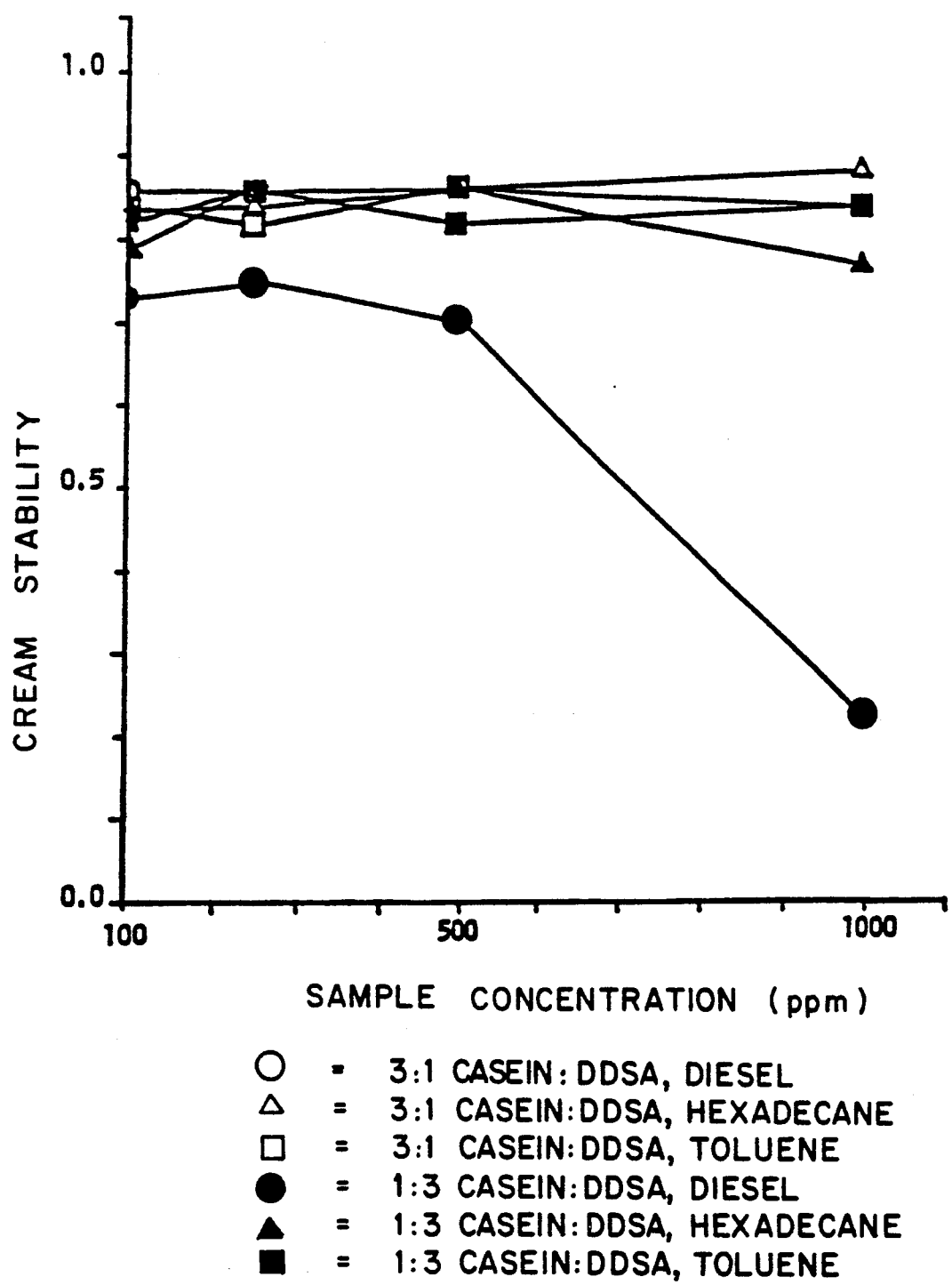
Figure 26:
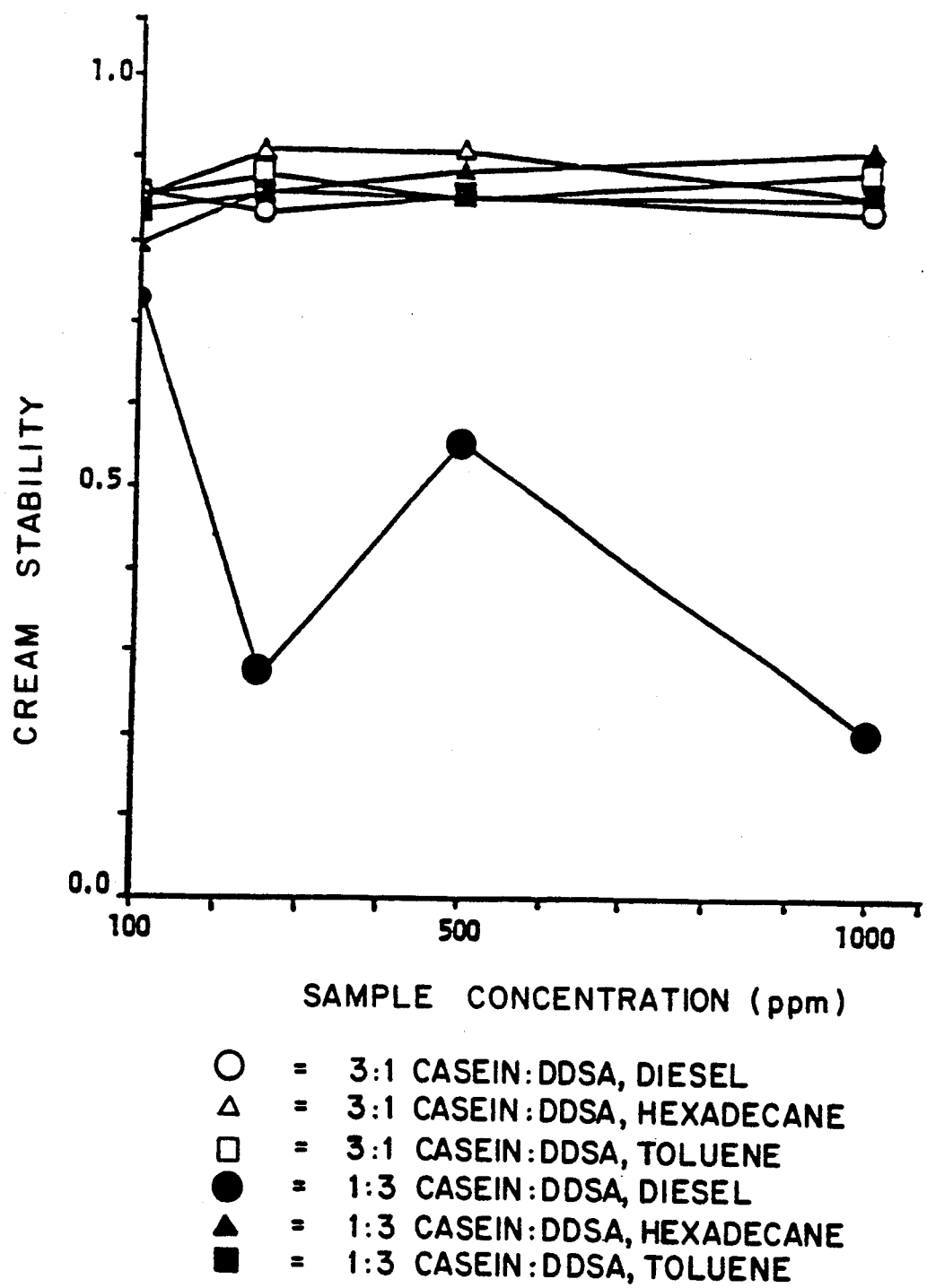
Figure 27:
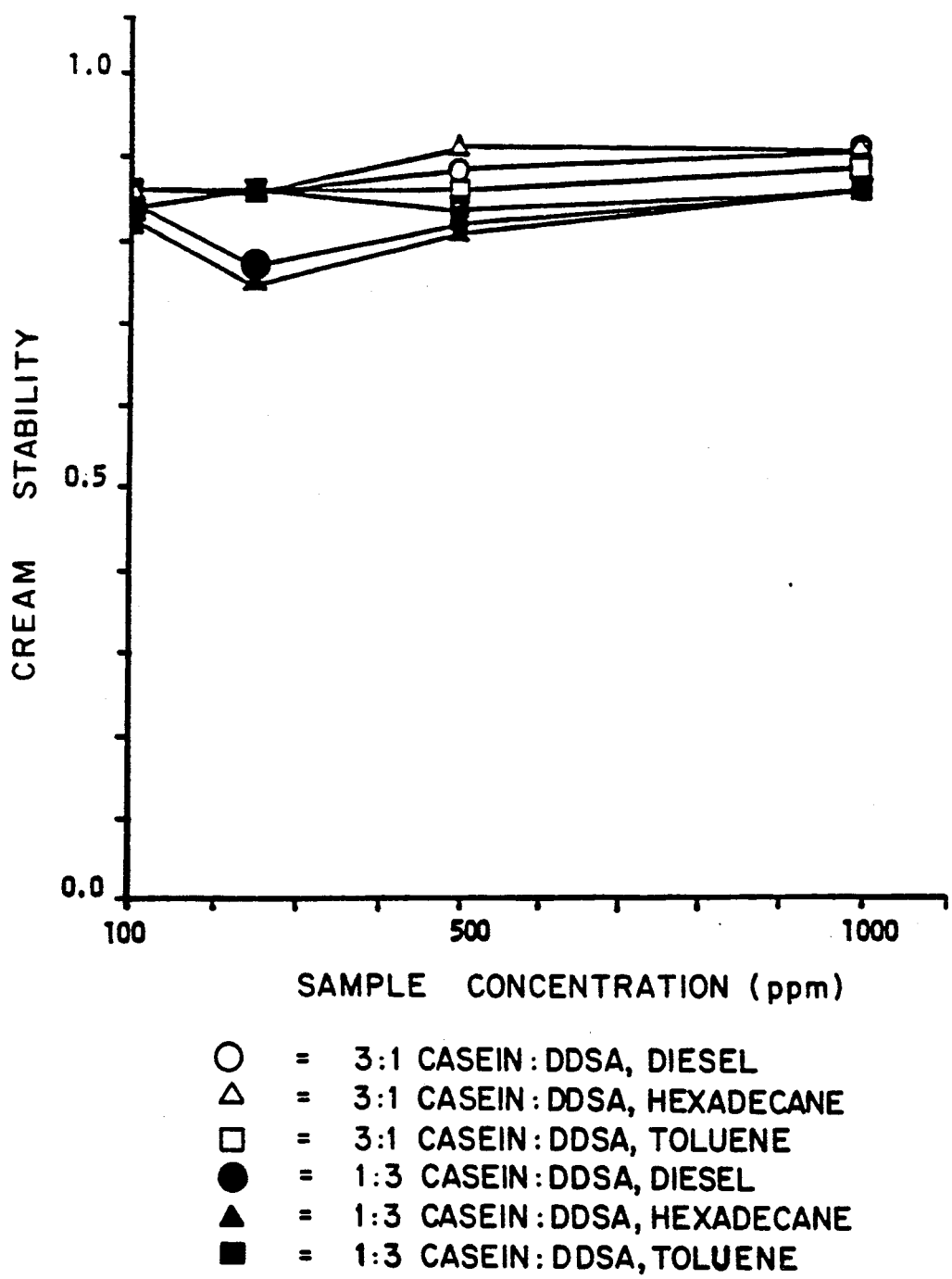
Figure 28:
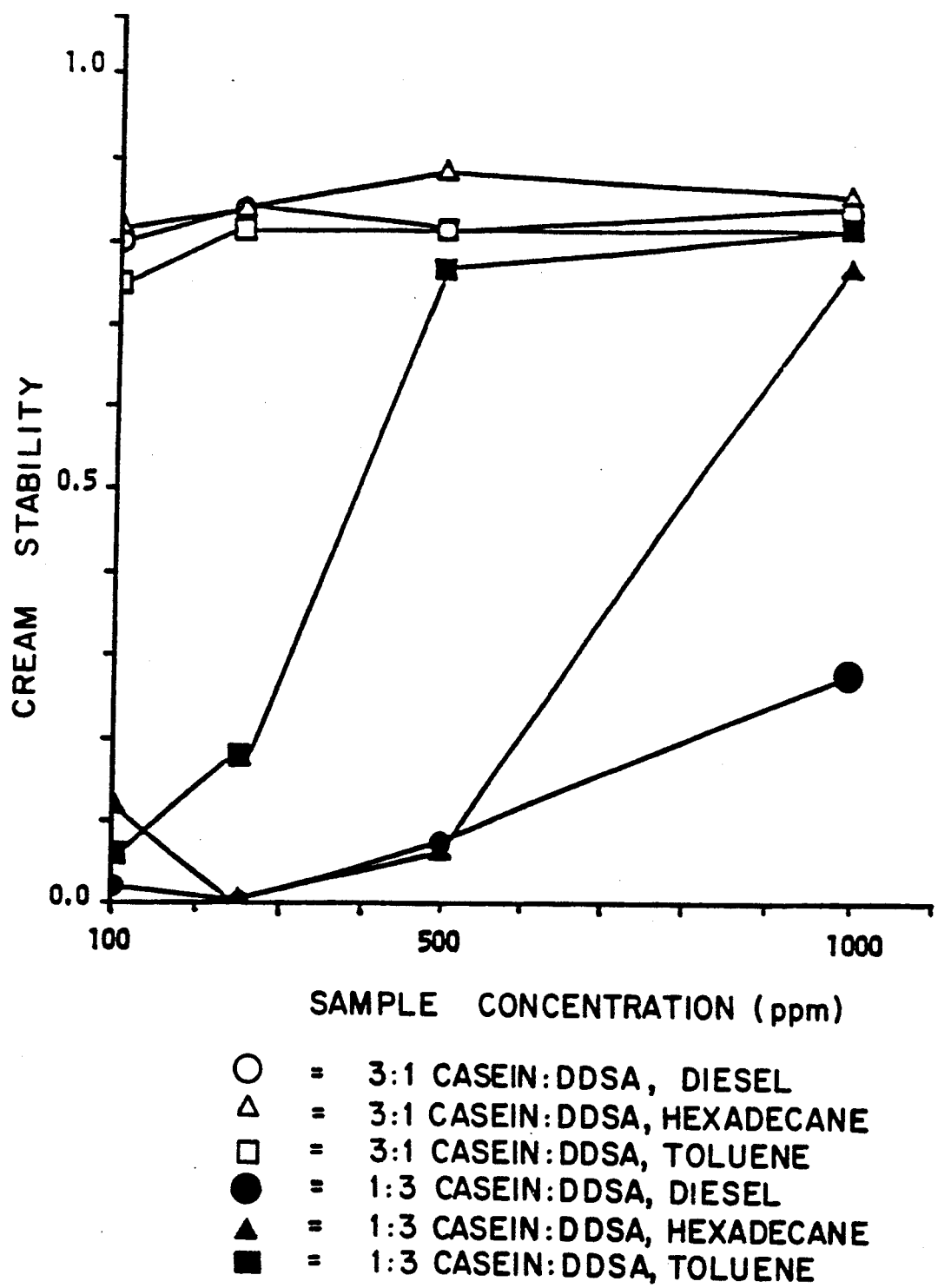
Figure 29:
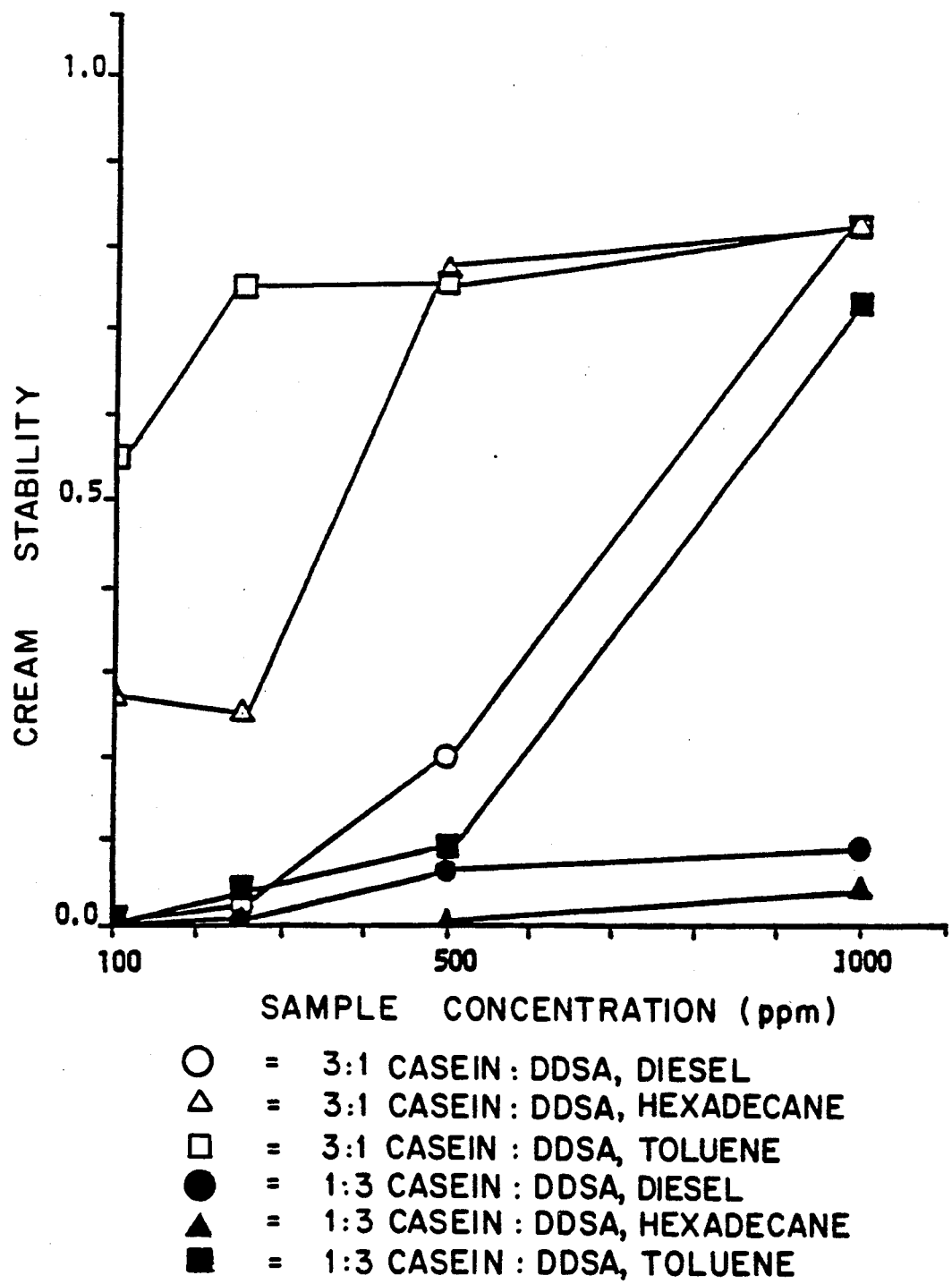
Figure 30:
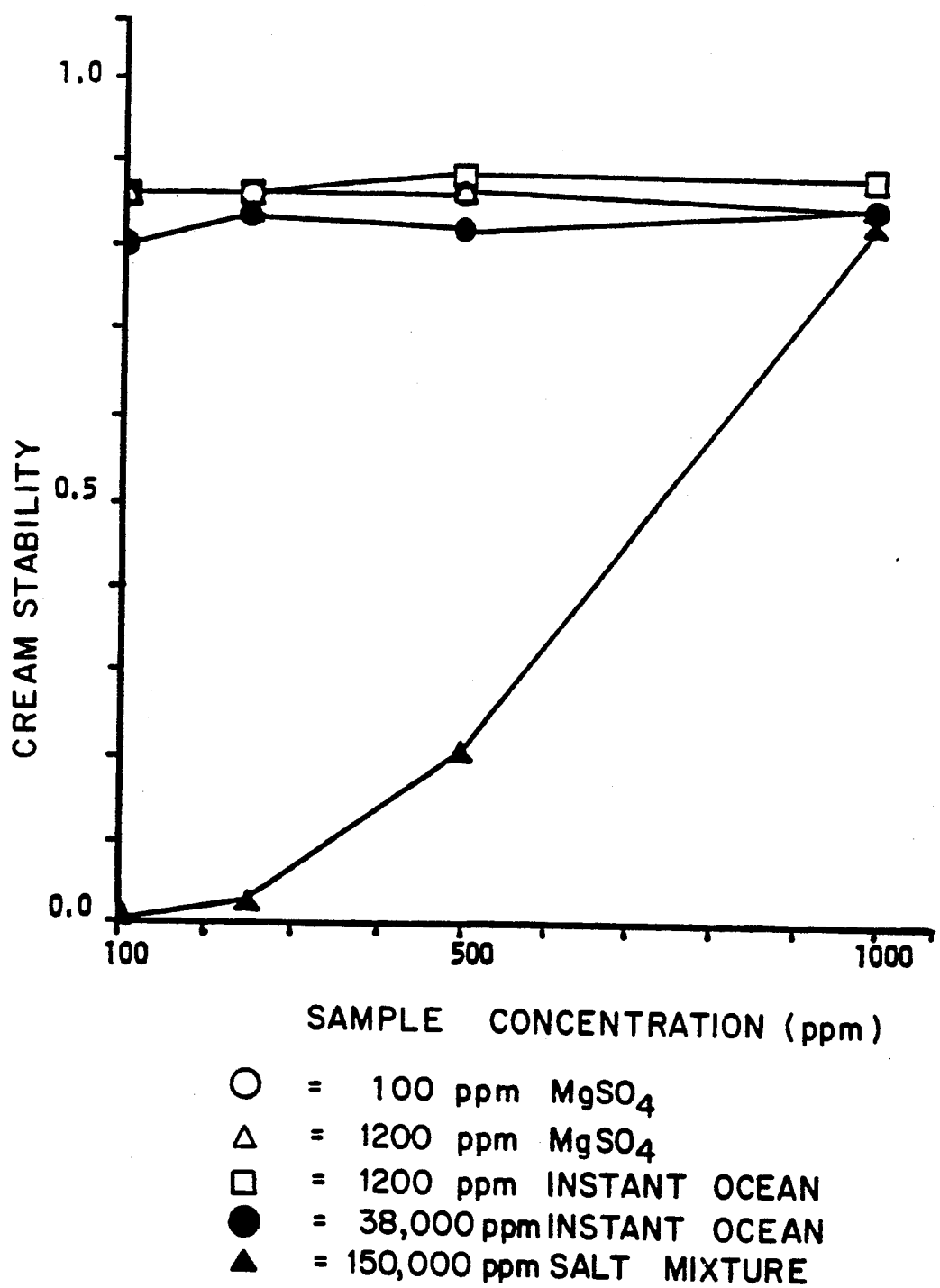
Figure 31:
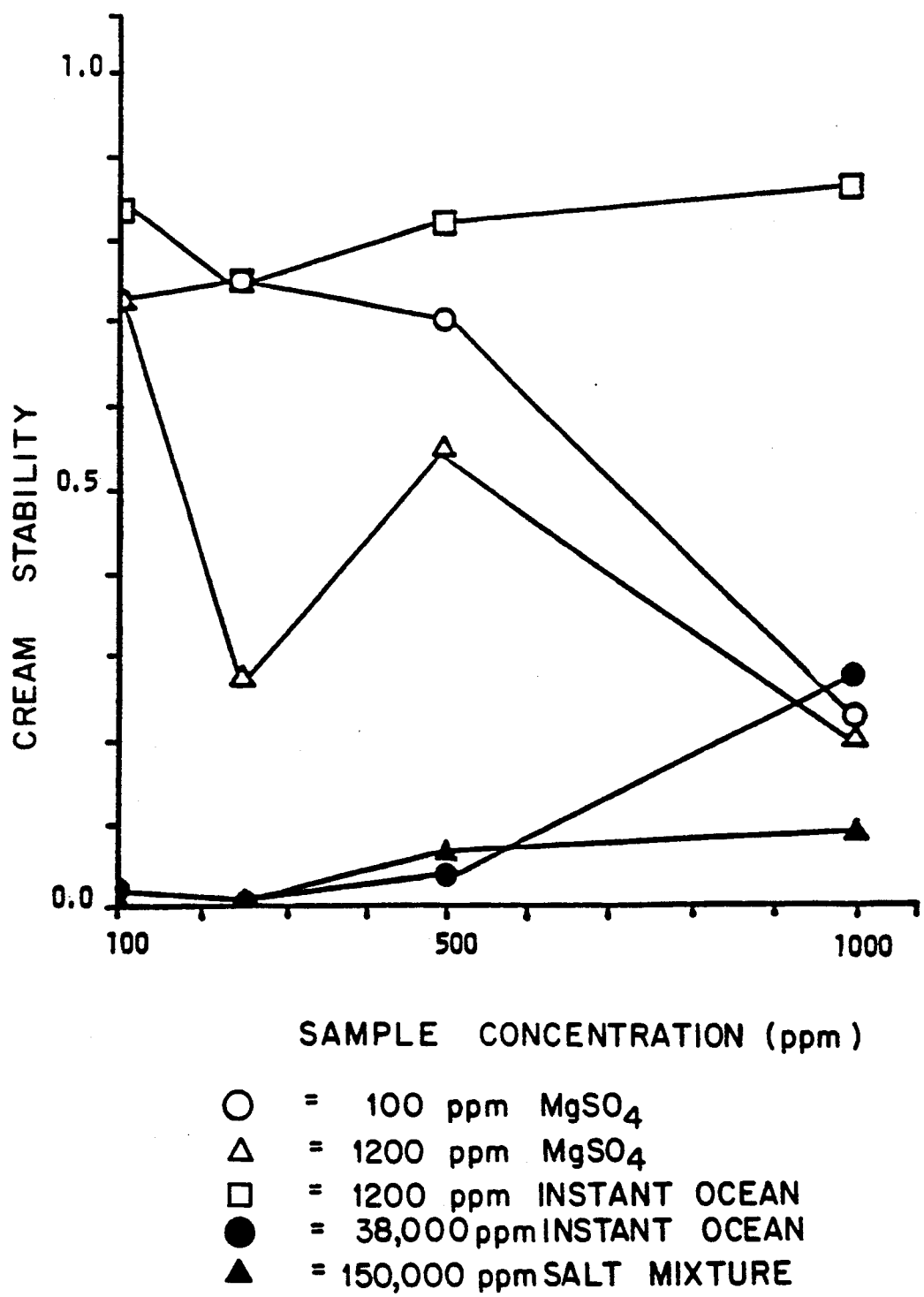
Figure 32:
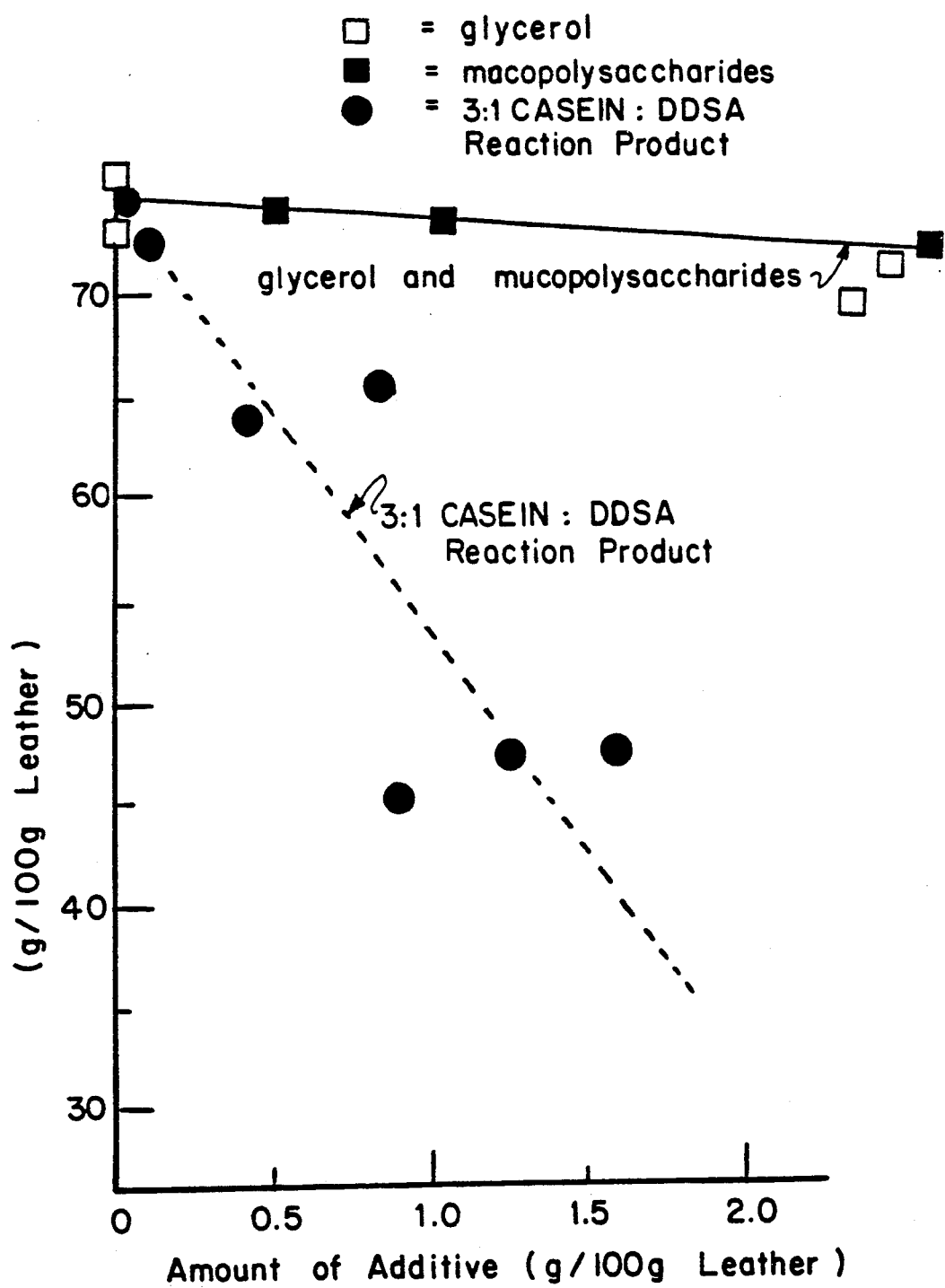

FIG. 1 graphically illustrates the effect of DDSA concentration on the DDSA Hydrolysis rate;

FIG. 2 graphically illustrates the effect of pH on the DDSA Hydrolysis rate;

FIG. 3 graphically illustrates the effect of temperature on the DDSA Hydrolysis rate;

FIG. 4 graphically illustrates the determination of the activation energy of DDSA hydrolysis;

FIG. 5 graphically illustrates the effect of DDSA concentration on the reaction of casein with DDSA;

FIG. 6 graphically illustrates the effect of stirring speed on the 3:1 casein:DDSA reaction rate;

FIG. 7 graphically illustrates the mass transport surface dependence of the casein:DDSA reaction (3:1);

FIG. 8 graphically illustrates the effect of pH on the 3:1 casein:DDSA reaction rate;

FIG. 9 graphically illustrates the effect of casein concentration on the reaction rate of casein with DDSA;

FIG. 10 graphically illustrates the effect of temperature on the 3:1 casein:DDSA reaction rate;

FIG. 11 graphically illustrates the determination of activation energy of the reaction of casein with DDSA (3:1);

FIG. 12 illustrates the proposed mechanism for DDSA reactions;

FIG. 13 graphically illustrates the comparison of activation energies of DDSA hydrolysis and the reaction of casein with DDSA (3:1);

FIG. 14 graphically illustrates the comparison of reaction rates of DDSA hydrolysis and the reaction of casein with DDSA (3:1);

FIG. 15 graphically illustrates hexadecane emulsification by 100 ppm casein:DDSA with 100 ppm salt;

FIG. 16 graphically illustrates hexadecane emulsification by 100 ppm casein:DDSA with 150,000 ppm salt;

FIG. 17 graphically illustrates the solubility of neutralized casein, 3:1 casein:DDSA and 1:3 casein:DDSA versus pH;

FIG. 18 graphically illustrates the solubility of neutralized casein, 3:1 casein:DDSA and 1:3 casein:DDSA in 0.1M NaCl versus pH;

FIG. 19 graphically illustrates the solubility of neutralized casein, 3:1 casein:DDSA and 1:3 casein:DDSA in 1.0M NaCl versus pH;

FIG. 20 graphically illustrates the solubility of neutralized casein, 3:1 casein:DDSA and 1:3 casein:DDSA in 1.0M $MgCl_2$ versus pH;

FIG. 21 graphically illustrates the viscosity of neutralized casein versus concentration;

FIG. 22 graphically illustrates the viscosity of 3:1 casein:DDSA versus concentration;

FIG. 23 graphically illustrates the viscosity of 1:3 casein:DDSA versus concentration;

FIG. 24 graphically illustrates the comparison of digestions of casein, 3:1 casein:DDSA and 1:3 casein:DDSA with maxatase;

FIG. 25 graphically illustrates the effect of concentration of 1:3 and 3:1 casein:DDSA on cream stability in 100 ppm $MgSO_4$;

FIG. 26 graphically illustrates the effect of concentration of 1:3 and 3:1 casein:DDSA on cream stability in 1200 ppm $MgSO_4$;

FIG. 27 graphically illustrates the effect of concentration of 1:3 and 3:1 casein:DDSA on cream stability in 1200 ppm instant ocean (medium shear);

FIG. 28 graphically illustrates the effect of concentration of 1:3 and 3:1 casein:DDSA on cream stability in 38,000 ppm instant ocean (available commercially typically from aquarium supply stores) (medium shear);

FIG. 29 graphically illustrates the effect of concentration of 1:3 and 3:1 casein:DDSA on cream stability in 150,000 ppm salt mixture (medium shear);

FIG. 30 graphically illustrates the effect of concentration of 3:1 casein:DDSA on cream stability with diesel oil;

FIG. 31 graphically illustrates the effect of concentration of 1:3 casein:DDSA on cream stability with diesel oil;

FIG. 32 graphically illustrates the effect of 3:1 Casein: DDSA on water evaporation from leather.

5. Description of the Invention

Generally stated, one aspect of this invention is a method for producing novel emulsifiers and emulsion stabilizers comprising reacting a protein preferably in an aqueous solution with a hydrophobic anhydride wherein the reaction conditions permit the bonding of hydrophobic groups onto said protein preferably on appropriate reactive portions or groups on the protein (i.e., and as used herein, would encompass terminal amino groups and/or amino acid side chain groups). In another embodiment of the disclosed invention the reaction may also be carried out with the same type of protein preparation but using a hydrophobic acylating agent (i.e. esters or acid chlorides) instead of a hydrophobic anhydride.

More specifically, this process comprises reacting a homogeneous or heterogeneous protein preparation with a derivative of succinic anhydride (alkyl or alkenyl) wherein the reaction conditions permit the succinylation of terminal amino groups and/or reactive side chains on said protein. The reactive side chains present may be those such as the side chain terminal amino group on lysine.

A preferred derivative of succinic anhydride utilized in the practice of this invention is Dodecenyl Succinic Anhydride (hereinafter DDSA). A protein is preferably dispersed in an aqueous solution during the reaction procedure with DDSA. DDSA (or the desired hydrophobic anhydride) is preferably present in excess relative to the protein during the reaction procedure. The precise ratio of protein to hydrophobic anhydride during the reaction procedure will vary with the particular reactants used in the process and the desired product characteristics. The optimum emulsification or emulsion stability characteristics is easily ascertained or created by following the procedures described herein. Essentially, however, altering the respective ratios of protein to hydrophobic anhydride for the reaction serves to alter the emulsification or emulsion stabilizing characteristics of the reaction product.

5.1. Overview of DDSA and DDSA Reaction Chemistry

Dodecenyl succinic anhydride otherwise known as ($DDSA = C_{12}H_{23}$—$H(C_2HO)_2O$) is made by reacting tetrapropylene with maleic anhydride (See reaction Scheme I).

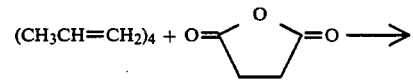

I

-continued

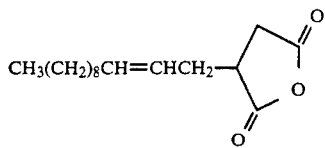

The product obtained is a mixture of various branched chains and not the normal straight chain compound. The advantage of the mixture of compounds is that it is a liquid and not a solid at room temperature as is the pure straight chain material. Each compound in the mixture contains a double bond which is necessary if the mixture is to be liquid at 25° C. DDSA is available commercially, from such companies as The Humphrey Chemical Co., North Haven, Conn. It has a boiling point of 377° F. and appears as a yellow, viscous liquid.

5.1.1 Reaction of DDSA with Water

DDSA reacts with water to form hydrolyzed DDSA as in the reaction II below:

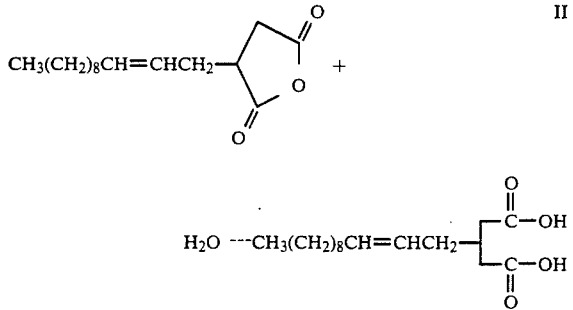

The heterogeneous (liquid:liquid) reaction is concentration independent of DDSA (FIG. 1) and stirring rate. The initial rapid increase in NaOH consumed (FIG. 1) is due to the initial neutralization of hydrolyzed DDSA and other acidic species in the DDSA used for these experiments.

The rate of reaction is pH dependent, increasing with increasing pH (FIG. 2). However, the disclosed inventive process can be carried out over a wide pH range from about a pH of 6 to a pH of about 11. The reaction is exothermic as expected of all anhydride-water reactions, and the reaction rate increases with increasing temperature (FIG. 3). Because the reaction is exothermic, the reaction mixture must be cooled, but on the laboratory scale the heat generated by the slow reaction of DDSA with water is easily controlled. FIG. 4 is semi-logarithmic plot of rate of reaction versus the inverse of the temperature. From the slope of the line on this figure one can determine the activation energy of the reaction.

$$E_a = \frac{R \ln \frac{\text{mmole NaOH}}{h}}{1/T (°K.)} = 8.7 \text{ kcal/mole}$$

Below 50° C. the data gives a straight line. The non-linearity above 50° C. is an indication that above 50° C. mass transfer of DDSA to water becomes a rate-limiting step.

5.1.2 Reaction of Protein with DDSA

DDSA reacts with dissolved protein to form a synthetic lipoprotein. More than one DDSA molecule can react with a molecule of protein yielding a protein core covered with molecules of DDSA, the extent of substitution largely depending on the concentration of reactants (see, for instance, FIG. 5). The rate of the reaction increases with increasing concentration of DDSA.

Unlike the DDSA-water reaction, the protein-DDSA reaction shows stirring rate dependence at room temperature. The rate determining step in the DDSA-protein reaction thus appears to be mass transfer of DDSA from insoluble DDSA (oil) to water. A double-logarithmic plot of reaction rate versus stirring speed results in a straight line with a slope of 1.94 (i.e. near 2.0) which is indicative of a reaction governed by liquid film mass transfer resistance.

DDSA reacts preferably with lysyl groups on the protein, therefore, the reaction is pH dependent (with the reaction being more rapid at higher pH since only the nonionized amino group reacts with the DDSA molecule). The reaction rate increases toward pH 9 and levels off at higher pH-values. However, DDSA may also react less rapidly with other groups such as serine and tyrosine or aspartic acid (as well as with the water present). Increasing the protein concentration increases the rate of the reaction, but the reaction is less than first order with respect to protein concentration.

5.2 Whole Broth Reaction

DDSA may be reacted with cell cultures whole broth harvests of microorganisms, such as *Acinetobacter calcoaceticus*. A fermentation is first carried with the microorganisms followed by preferably a cell-lysis step (e g. heat kill) prior to reaction of this broth with DDSA. An in situ reaction with DDSA may be performed on the whole broth. This reaction may be run in the fermentation vessel itself. The protein "substrates" in the reaction include cell-associated proteins, "free" extra-cellular proteins and extra-cellular proteins which may be "bound" to other cellular products, such as Emulsans produced by *Acinetobacter calcoaceticus*. In these reactions, the DDSA is allowed to react with whatever proteins are in the broth.

5.3. Overview of emulsifiers and emulsion stability

An emulsion is a significantly stable suspension of particles of liquid of a certain size within a second, immiscible liquid. The stability of the emulsion is relative to its intended use and may remain stable for either a long or short period of time. The size of the dispersed particles determine whether the emulsion is a macro-emulsion (typically, particle size of 0.2–50 um) or microemulsion (typically, particle size of 0.01–0.20 um). The appearance of the emulsion is determined by the size of the particle dispersed in the emulsion (1 um, milky white; 1–0.1 um , blue-white; 0.1–0.05 um, gray, semitransparent; 0.05 um, transparent).

The two types of macro-emulsions are based on the nature of the dispersed phase: oil-in-water (o/w) and water-in-oil (w/o). Neither type of emulsion is in thermodynamic equilibrium. Usually an emulsifying agent, typically also a surface-active agent, is required to render a suspension stable enough to be called an emulsion. Effective emulsifying agents are often mixtures of two or more substances. Typical commercial products such as paints, polishes, pesticides, metal cutting oils, margarine, cosmetics, metal cleaners, and textile processing oils are emulsions or are used in emulsified form.

In the formation of emulsions, one of the two immiscible liquids is broken up into particles that are dispersed in the second liquid. Since the interfacial tension between two immiscible pure liquids is always greater than zero, this dispersion of the inner liquid, which produces a large increase in the area of the interface between them, results in a correspondingly large increase in the interfacial free energy of the system. The emulsion produced is consequently highly unstable thermodynamically relative to the two bulk phases separated by a minimum area of interface. The function of the emulsifying agent is to stabilize this basically unstable system for a sufficient time so that it can perform some function. This the emulsifying agent does by absorption at the liquid/liquid interface as an oriented interfacial film. This oriented film performs a number of functions: (1) It reduces the interfacial tension between the two liquids and consequently the thermodynamic instability of the system resulting from the increase in the interfacial area between the two phases, (2) it decreases the rate of coalescence of the dispersed liquid particles by forming mechanical, steric, and/or electrical barriers around them. The steric and electrical barriers inhibit the close approach of one particle to another. The mechanical barrier increases the resistance of the dispersed particles to mechanical shock and prevents them for coalescing when they do collide.

The term stability, when applied to emulsions used for practical applications and as utilized herein, usually refers to the resistance of emulsions to the coalescence of their dispersed droplets. The mere rising or settling of the droplet's or creaming, because of a difference in density between them and the continuous phase is usually not considered instability. The rate of coalescence of the droplets in an emulsion provides, however, a quantitative measure of emulsion stability.

The rate at which the droplets of a macroemulsion coalesce to form larger droplets and eventually "break" the emulsion has been found to depend on a number of factors: (1) the physical nature of the interfacial film, (2) the existence of an electrical of steric barrier on the droplets, (3) the viscosity of the continuous phase, (4) the size distribution of the droplets, (5) the phase volume ratio, and (6) the temperature.

A molecule which is an effective emulsion stabilizer should have fatty acids or other hydrophobic groups attached to it, which can align themselves at the surface of an oil drop or from the surface of an oil drop into the oil drop of an emulsion. In addition, it should be a molecule which has charged and/or polar groups attached to it which can align themselves at or into the water phase of an emulsion. Furthermore, the molecule should have a high molecular weight, i.e. a polymer, which allows it to take advantage of cooperative as well as steric effects. Cooperative effects means that small individual interactions, such as the interaction of a single side chain with the solvent, are added together to make the removing of the molecule from the surface very difficult, hence resulting in a strong overall effect.

Generally stated, a cream stability assay provides a quantitative determination of the degree to which an emulsion stabilization agent delays the coalescence of the droplets in an emulsion. This assay is used in the following examples.

5.4. Assays for Emulsion Stability and Emulsification Activity

An "emulsifier" can have two different functions: (1) it may enhance the emulsification process by lowering free energy (interfacial tension) and thereby reduce the energy required to create small droplets (i.e. an emulsion), and (2) it may stabilize the surface that has been created against "coalescing forces" (gravity, impact, and attractive van der Waals forces) by establishing a "barrier" at the droplet surfaces.

The first function is typically satisfied by low molecular weight synthetic surfactants, while the second function is favored by high molecular stabilizers such as emulsan or hydrophobically modified proteins, i.e. DDSA protein compounds described herein.

A cream stability assay evaluates emulsion stability after an emulsification process is completed. This is necessary in order to compare the performance of new products as colloid stabilizers without getting false positives from products that also happened to be good surfactants.

The Emulsification Activity assay as utilized herein is performed by shaking a small emulsifier sample in 15 ml pH 7.2 Tris-Hcl buffer containing 10 mM $MgSO_4$ and 0.2 ml 1:1 mixture of hexadecane:2-methylnaphtalene in baffled 250 ml flasks for 30 minutes at 300 rpm and 30° C., immediately whereafter the turbidity (optical density) of the emulsion that is formed is recorded at 660 nm in a Spectronic-20 or other suitable spectrophotometer.

The results are compared to the optical density reading of a suitable standard (herein purified Emulsan) and are recorded as EAU/L solution or EAU/g sample (EAU='emulsification activity units').

The Cream Stability assay is performed by first emulsifying (by a standard shaking procedure) 2 ml oil into 4 mL aqueous phase (which contains the emulsion stabilizer and appropriate salts) in a test tube, and thereafter measuring the separation of oil phase (by coalescence) with time, either on the benchtop ("low shear"), or upon centrifugation ("medium shear" at about 290×g, and "high shear" at about 1880×g). The standard centrifugation time is 5 minutes.

The results of the cream stability test are scored either as % stability or fractional stability; i.e. as % or fraction of original oil volume remaining emulsified after this treatment. In some cases the results are presented semi-quantitatively as either "low", "medium", or "high" stability, where "low" represents (roughly) 0–20% stability, "medium" is in the range 30–70% stability, and "high" would be 80–100% stability (and in-between regimes would be denoted "medium-high", etc.). A difference in cream stability of less than $+/-10\%$ is not statistically significant for most test systems.

The HPLC-assay referred to for the microbial emulsifiers is a measurement of microbial polysaccharides at one million molecular weight (using a molecular sieve column) and quantified by UV-absorption at 205 nm (see enclosed procedure). This assay has been employed to determine "specific activity" of the polysaccharides (EAU/g polysaccharide rather than EAU/g dry weight).

6. EXAMPLES

The following examples further illustrate the preferred and novel process and compounds of the invention, here specifically relating to hydrophobically enhanced modified proteins such as a protein-DDSA complex or, more specifically, a casein-DDSA product.

6.1. Casein-DDSA

Casein is not a single pure protein, but rather a mixture of phosphoproteins related in structure which are derived from milk by acid precipitation under controlled conditions. [Windholz, Martha (ed.), "The Merck Index", 1983, p. 263. ] Bovine (cow) casein is used in this example exclusively since only bovine casein is commercially available in large quantities. An average casein molecule contains approximately 210 amino acid residues with an approximate molecular weight of 23,000 daltons. Table 1 gives the amino acid composition of casein.

TABLE 1

Amino Acid Composition of Bovine B - Casein (Residues per monomer M.W. 27,000)

| | |
|---|---|
| Gly | 10.2 |
| Ala | 10.3 |
| Ser | 9.4 |
| Thr | 4.9 |
| Pro | 13.7 |
| Val | 11.9 |
| Ileu | 12.3 |
| Leu | 21.5 |
| Phe | 9.9 |
| Tyr | 12.3 |
| Try | 2.3 |
| Cys/2 | 0 |
| Met | 5.9 |
| Asp | 13.9 |
| Glu | 44.1 |
| $NH_3$ | 15.4 |
| Arg | 8.6 |
| His | 5.8 |
| Lys | 17.8 |
| Total N (%) | 14.7 |
| Phosphorus (%) | 1.0 |

DDSA reacts with dissolved casein to form a synthetic lipoprotein. The reaction is given below:

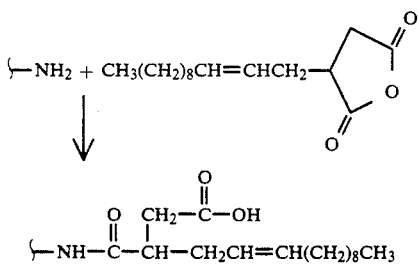

This reaction should not be considered the only reaction that can take place, since DDSA can also react with serine, aspartic acid, tyrosine and water. More than one DDSA molecule can and does react with a molecule of casein yielding a protein core covered with molecules of DDSA, the ratio of which largely depends on the concentration of reactants. FIG. 5 shows the reaction curves obtained (base addition w/time for pH-control) by varying the ratio of DDSA to casein under otherwise identical conditions. The rate of the reaction increases with increasing concentration of DDSA which is not the case of the reaction of DDSA with water.

6.1.1 Overview of Casein-DDSA Reaction

FIG. 6 shows the stirring rate dependence for casein-DDSA reaction. Unlike the DDSA-water reaction which shows no stirring rate dependence, this reaction shows stirring rate dependence. The reason for this stirring rate dependence with DDSA is that the rate determining step in the DDSA-Casein reaction must be mass transfer of DDSA from the insoluble liquid droplets of DDSA. Increasing the stirring rate causes the droplets to become smaller and have a larger combined surface area, hence creating more area for mass transfer. A double logarithmic plot of reaction rate versus stirring speed is shown in FIG. 7. A straight line was obtained with a slope of 1.94 which is indicative of a reaction whose rate is governed by a mass transport across a liquid film.

The DDSA molecule principally reacts with lysine amino acid on casein. Therefore, one expects the reaction to show a pH dependence with the reaction being more rapid at higher pH since only the nonionized amino group reacts with the DDSA molecule. FIG. 8 shows such a plot. The rate of reaction increases until approximately pH 9 after which the rate increase ceases.

The shape of this curve is not exactly the shape one would predict for the reaction of an anhydride with an amino group. There are two reasons for this difference. First, DDSA is reacting with other groups such as serine and tyrosine and aspartic acid as well as with the water present, and other reactions, while slower, do affect the shape of the curve because their reaction rates with DDSA are different than lysine's reaction rate. Second, casein shows a pH dependence with its solubility, hence at low pH, the real concentration of casein is lower than at pH 8.2.

FIG. 9 shows that increasing the casein concentration increases the rate of the reaction. The reaction is not first order to casein concentration since doubling the latter did not double the rate of reaction. These results are probably due to the competing reactions, and possibly due to the overall heterogeneous nature of the reaction.

The reaction of casein with DDSA increases with increasing temperature as shown in FIG. 10. In order to determine the activation energy of this reaction a semilogarithmic plot of reaction versus reciprocal absolute temperature was made (FIG. 11). The activation energy for this reaction is 5.2 kcal/mole.

The proposed mechanism for the Casein:DDSA Reaction is illustrated graphically in FIG. 12 and is described as follows:

1. The reaction of DDSA with water at lower temperatures is independent of stirring rate and concentration of DDSA. The rate determining step is the reaction of DDSA with water, and not the diffusion of DDSA through the barrier film surrounding the surface of the droplet, hence $$k_1 > k_2$$

2. The reaction of DDSA with casein is dependent on stirring rate and concentration of DDSA. The rate determining step for this reaction is the mass transport of DDSA to or through the surface of the barrier film on the droplets. Hence in the presence of casein $$k_3 > k_1 > k_2$$

3. The activation energy of the Casein-DDSA reaction (5.2 kcal/mole) is less than the activation energy for DDSA hydrolysis (8.7 kcal/mole). FIG. 13 shows the plot for both Casein:DDSA and DDSA hydrolysis.

The reaction conditions were optimized since there are two different competing reactions occurring during the Casein-DDSA reaction (DDSA Casein and DDSA-hydrolysis, with only one desired product (DDSA:-Casein). FIG. 14 (a comparison of the pH dependence of the Casein:DDSA reaction and DDSA hydrolysis) shows that the rate of DDSA hydrolysis is constantly increasing with increasing pH, while the rate of Casein-DDSA reaction increases up till approximately pH 8.5. Hence, increasing the pH past 8.5 only increases the rate of the competing hydrolysis and not the Casein:DDSA reaction.

By examining the slope of both lines in FIG. 14, the activation energies can be determined for both reactions (casein-DDSA versus DDSA-hydrolysis).

Since the lines are not parallel, being further apart at lower temperatures, the reaction preferably should be run at cool temperatures since the competing reaction (DDSA-hydrolysis) is proportionately slower at cold temperatures than the casein-DDSA reaction. The reaction could be carried out at near 0° C., but 25° C. is preferred for the following reasons:

1. The overall rate of the casein-DDSA reaction is approximately 200% faster at 25° C. than at 0° C. (FIG. 13).

2. The cost of cooling a large reactor to 0° C. is high; and

3. The additional small quantity of hydrolized DDSA formed at 25° C. does not seem to be detrimental to uses of Casein:DDSA.

6.2. Casein-DDSA Products

6.2.1 Covalently Linked Casein:DDSA

Under certain circumstances covalent bonded Casein:DDSA is superior in performance to a simple mixture of Casein:DDSH. Under high salt concentration the covalently bonded DDSA cannot dissociate from the casein which is more likely under those conditions with just a mixture. FIGS. 15 and 17 illustrate this point. FIG. 16 shows that under low salt concentrations the covalently linked product is only a little better than the non-covalently linked product. On the other hand, FIG. 16 shows that under high salt concentrations a very large improvement in cream stability is observed with the covalently linked product. Table 1 gives other examples of the advantage of covalently bonding the DDSA to the casein molecule.

6.2.2 Cream Stability of 3:1 Casein:DDSA in the Presence of Hydrolyzed DDSA The reaction of DDSA with casein is not 100% quantitative (some DDSA reacts with water) especially in the case of 1:3 Casein:DDSA. In the case of 1:3 Casein:DDSA the molar ratio of casein to DDSA is approximately 1:365. Since casein contains only 210 amino acid residues and DDSA can react with some of them, then it is apparent that a reasonable percentage of the DDSA is hydrolyzed. The effect of this hydrolyzed DDSA on the Casein:DDSA's emulsion stabilization properties was investigated, since if hydrolyzed DDSA interferes with emulsion stabilization, then it would be desirable to minimize the amount of hydrolyzed DDSA.

A series of experiments was performed to determine if adding hydrolyzed DDSA to 3:1 casein:DDSA has an effect on the cream stabilizing ability of 3:1 casein:DDSA (see Table 2A). Table 2B shows of adding hydrolyzed DDSA has no effect.

6.2.3 Comparison of Characteristics of Different Casein:DDSA Compounds

Most of the experiments were performed with 3:1 Casein:DDSA, a small number with 1:3 Casein:DDSA, and a few with other ratios. The choice of 3:1 was not arbitrary, but rather based on a number of experiments designed to optimize the ratio. Table 3 gives the results of some of these experiments. In most cases the 3:1 ratio yields the highest cream stability except in a few cases where the 1:3 is superior.

On a molar basis 3:1 Casein:DDSA (w/w) is approximately 1 mole casein to 30 moles of DDSA, while the 1:3 Casein:DDSA (w/w) is approximately 1 mole of casein to 265 moles of DDSA.

TABLE 2A

Comparison of Covalently Bonded Casein: DDSA with the Noncovalent Mixture Cream Stability Assay
(Cream Stability at Indicated Salinity)

| Sample | Hydrocarbon | Shear Level | 100 ppm $MgSo_4$ | 1200 ppm $MgSO_4$ |
|---|---|---|---|---|
| 3:1 Casein: DDSA (covalent) | Toluene | M | 0.95 | 1.0 |
| 3:1 Casein: DDSA (mixture) | Toluene | M | 0.81 | 0.72 |
| 3:1 Casein: DDSA (covalent) | 1/1 Hexadecane/2 methyl-napthalene | M | 0.86 | 0.91 |
| 3:1 Casein: DDSA (mixture) | 1:1 Hexadecane/2 Methyl-napthalene | M | 0 | 0 |
| 1:3 Casein: DDSA (covalent) | Toluene | M | 0.18 | 0.54 |
| 1:3 Casein: DDSA (mixture) | Toluene | M | 0 | 0 |
| 1/3 Casein: DDSA (covalent) | 1:1 Hexadecane/2-methyl-napthalene | L | 0.48 | 0.65 |
| 1:3 Casein: DDSA | 1:1 Hexadecane/2-methyl-napthalene | L | 0.09 | 0.04 |

| Sample | Hydrocarbon | Shear Level | 1200 ppm Instant Ocean | 38,000 ppm Instant Ocean | 150,000 ppm Salt Mixture |
|---|---|---|---|---|---|
| 3:1 Casein: DDSA (covalent) | Toluene | M | 1.0 | 0.91 | 0.91 |
| 3:1 Casein: DDSA (mixture) | Toluene | M | 0 | 0.54 | 0.54 |
| 3:1 Casein: DDSA (covalent) | 1/1 Hexadecane/2 methyl-napthalene | M | 0.91 | 0.95 | 0.72 |
| 3:1 Casein: DDSA (mixture) | 1:1 Hexadecane/2 Methyl-napthalene | M | 0 | 0 | 0 |
| 1:3 Casein: | Toluene | M | 0.09 | 0.81 | 0.22 |

TABLE 2A-continued

Comparison of Covalently Bonded Casein: DDSA with the Noncovalent Mixture Cream Stability Assay (Cream Stability at Indicated Salinity)

| | | | | | |
|---|---|---|---|---|---|
| DDSA (covalent) 1:3 Casein: DDSA (mixture) | Toluene | M | 0 | 0 | 0 |
| 1/3 Casein: DDSA (covalent) | 1:1 Hexadecane/2-methyl-napthalene | L | 0.65 | 0.58 | 0.41 |
| 1:3 Casein: DDSA | 1:1 Hexadecane/2-methyl-napthalene | L | 0 | 0.31 | 0.22 |

TABLE 2B

Effect of Addition of Hydrolyzed DDSA on 3:1 Casein: DDSA (Cream Stability Assay, Medium Shear, Hexadecane)

| Hydrolyzed DDSA | MgSO$_4$ 100 ppm | MgSo$_4$ 100 ppm | Instant Ocean 1200 ppm | Instant Ocean 38,000 ppm | Salt Mixture 150,000 ppm |
|---|---|---|---|---|---|
| 0 | 0.84 | 0.88 | 0.86 | 0.86 | 0.18 |
| 5 | 0.86 | 0.88 | 0.86 | 0.82 | 0.23 |
| 10 | 0.86 | 0.88 | 0.88 | 0.86 | 0.09 |
| 25 | 0.84 | 0.90 | 0.86 | 0.84 | 0.14 |
| 50 | 0.88 | 0.90 | 0.84 | 0.80 | 0.02 |
| 100 | 0.84 | 0.90 | 0.90 | 0.71 | 0.02 |
| 200 | 0.86 | 0.90 | 0.86 | 0.78 | |

A standard cream stability assay was performed. All tubes contained 100 ppm of Casein:DDSA. The concentration of hydrolyzed DDSA was varied.

TABLE 3

Comparison of Different Casein: DDSA Compounds Cream Stability Assay

| Sample | Hydrocarbon | Shear Level | 100 ppm MgSo$_4$ | 1200 ppm MgSo$_4$ |
|---|---|---|---|---|
| 10:1 Casein: DDSA | Hexadecane | M | 0.31 | 0.13 |
| 3:1 Casein: DDSA | Hexadecane | M | 0.91 | 0.95 |
| 1:1 Casein: DDSA | Hexadecane | M | 0.31 | 0.90 |
| 1:3 Casein: DDSA | Hexadecane | M | 0.18 | 0.95 |
| 1:10 Casein: DDSA | Hexadecane | M | 0 | 0 |
| 10:1 Casein: DDSA | Toluene | M | 0.04 | 0.04 |
| 1:1 Casein: DDSA | Toluene | M | 0.31 | 0.91 |
| 1:3 Casein: DDSA | Toluene | M | 0.82 | 1.0 |
| 1:10 Casein: DDSA | Toluene | M | 0 | 0 |
| 10:1 Casein: DDSA | 1:1 Hexadecane/2-methyl-napthalene | M | 0.04 | 0 |
| 3:1 Casein: DDSA | 1:1 Hexadecane/2-methyl-napthalene | M | 0.86 | 0.91 |
| 1:1 Casein: DDSA | 1:1 Hexadecane/2-methyl-napthalene | M | 0.31 | 0.22 |
| 1:1 Casein: DDSA | 1:1 Hexadecane/2-methyl-napthalene | M | 0.09 | 0.04 |
| 1:10 Casein: DDSA | 1:1 Hexadecane/2-methyl-napthalene | M | 0 | 0 |

TABLE 3-continued

Comparison of Different Casein: DDSA Compounds Cream Stability Assay

| Sample | Hydrocarbon | Shear Level | 12,000 ppm Instant Ocean | 38,000 ppm Instant Ocean | 150,000 ppm Salt Mixture |
|---|---|---|---|---|---|
| 10:1 Casein: DDSA | Hexadecane | M | 0.18 | 0.09 | 0 |
| 3:1 Casein: DDSA | Hexadecane | M | 0.95 | 0.09 | 0.18 |
| 1:1 Casein: DDSA | Hexadecane | M | 0 | 0.77 | 0.31 |
| 1:3 Casein: DDSA | Hexadecane | M | 0.04 | 0.31 | 0.77 |
| 1:10 Casein: DDSA | Hexadecane | M | 0 | 0 | 0 |
| 10:1 Casein: DDSA | Toluene | M | 0 | 0.45 | 0.63 |

| Sample | Hydrocarbon | Shear Level | 100 ppm MgSo$_4$ | 1200 ppm MgSO$_4$ |
|---|---|---|---|---|
| 1:1 Casein: DDSA | Toluene | M | 0.95 | 0.95 | 0.73 |
| 1:3 Casein: DDSA | Toluene | M | 0.55 | 0.89 | 0 |
| 1:10 Casein: DDSA | Toluene | M | 0 | 0 | 0 |
| 10:1 Casein: DDSA | 1:1 Hexadecane/2-methyl-napthalene | M | 0.18 | 0.63 | 0.54 |
| 3:1 Casein: DDSA | 1:1 Hexadecane/2-methyl-napthalene | M | 0.91 | 0.95 | 0.72 |
| 1:1 Casein: DDSA | 1:1 Hexadecane/2-methyl-napthalene | M | 0.86 | 0.91 | 0.72 |

| Sample | Hydrocarbon | Shear Level | 12,000 ppm Instant Ocean | 38,000 ppm Instant Ocean | 150,000 ppm Salt Mixture |
|---|---|---|---|---|---|
| 1:3 Casein: DDSA | 1:1 Hexadecane/2-methyl-napthalene | M | 0.13 | 0.09 | 0.09 |
| 1:10 Casein: DDSA | 1:1 Hexadecane/2-methyl-napthalene | M | 0 | 0 | 0 |

TABLE 4

Cream Stability of Casein:DDSA in Various Ratios of Hexadecane: Toluene (Medium Shear)

| Sample | Hydrocarbon | 100 ppm MgSo$_4$ | 1200 ppm MgSO$_4$ |
|---|---|---|---|
| 3:1 Casein: DDSA | Hexadecane | 0.86 | 0.88 |
| 3:1 Casein: DDSA | 3:1 Hexadecane/Toluene | 0.86 | 0.88 |
| 3:1 Casein: DDSA | 1:1 Hexadecane/Toluene | 0.88 | 0.88 |
| 3:1 Casein: DDSA | 1:3 Hexadecane/Toluene | 0.88 | 0.90 |
| 3:1 Casein: DDSA | Toluene | 0.90 | 0.90 |
| 1:3 Casein: DDSA | Hexadecane | 0.88 | 0.86 |
| 1:3 Casein: | 3:1 Hexa- | 0.86 | 0.82 |

TABLE 4-continued

Cream Stability of Casein:DDSA in Various Ratios of Hexadecane: Toluene (Medium Shear)

| DDSA | decane/ Toluene | | |
|---|---|---|---|
| 1:3 Casein: DDSA | 1:1 Hexa- decane/ Toluene | 0.76 | 0.77 |
| 1:3 Casein: DDSA | 1:3 Hexa- decane/ Toluene | 0.82 | 0.77 |
| 1:3 Casein DDSA | Toluene | 0.80 | 0.90 |

| Sample | Hydrocarbon | 12,000 ppm Instant Ocean | 38,000 ppm Instant Ocean | 150,000 ppm Salt Mixture |
|---|---|---|---|---|
| 3:1 Casein: DDSA | Hexadecane | 0.86 | 0.80 | 0.18 |
| 3:1 Casein: DDSA | 3:1 Hexa- decane/ Toluene | 0.86 | 0.82 | 0.66 |
| 3:1 Casein: DDSA | 1:1 Hexa- decane/ Toluene | 0.88 | 0.79 | 0.60 |
| 3:1 Casein: DDSA | 1:3 Hexa- decane/ Toluene | 0.90 | 0.80 | 0.57 |
| 3:1 Casein: DDSA | Toluene | 0.90 | 0.82 | 0.62 |
| 1:3 Casein: DDSA | Hexadecane | 0.82 | 0.09 | 0 |
| 1:3 Casein: DDSA | 3:1 Hexa- decane/ Toluene | 0.86 | 0.05 | 0 |
| 1:3 Casein: DDSA | 1:1 Hexa- decane/ Toluene | 0.84 | 0.05 | 0 |
| 1:3 Casein: DDSA | 1:3 Hexa- decane/ Toluene | 0.84 | 0.07 | 0 |
| 1:3 Casein DDSA | Toluene | 0.84 | 0.07 | 0 |

Table 4 gives the results of experiments that determined that Casein:DDSA (1:3 and 3:1) derivatives have a broad ability to stabilize different ratios of hexadecane:toluene.

FIGS. 17 through 20 give the solubilities versus pH of casein, 3:1 Casein:DDSA and 1:3 Casein:DDSA versus pH in water, 0.1M NaCl, 1.0M NaCl and 1.0M $MgCl_2$ respectively. Overall, especially at high salt concentrations, the casein is the most soluble, followed by 1:3 Casein:DDSA and finally the 3:1 Casein:DDSA. Adding EDTA to Casein:DDSA solutions containing $MgCl_2$ causes the Casein:DDSA to be somewhat more soluble.

FIGS. 21, 22, and 23 show the viscosity of casein, 3:1 Casein:DDSA and 1:3 Casein:DDSA, respectively. The 1:3 Casein:DDSA has the lowest viscosity of the three solutions, probably because a large percentage of the 1:3 Casein:DDSA is just low molecular weight hydrolyzed DDSA. A solution of the 3:1 Casein:DDSA is not pseudoplastic and behaves like a Newtonian fluid.

The viscosity of solution of pure casein, FIG. 21, shows a much higher viscosity per gram of casein than the 1:3 Casein:DDSA. This behavior is expected since casein has a higher molecular weight than the hydrolyzed DDSA which probably makes up a high percentage of the 1:3 Casein:DDSA .

Solutions of 3:1 Casein:DDSA have the highest viscosity of the three materials tested on a g/L basis. This is probably a result of confirmational change in the Casein molecule as a result of the higher negative charge density after chemical modification (electrostatic repulsion).

The viscosities of solutions of these three materials varies relative to their casein content. For casein a 100 g/L solution gives a viscosity of 25 cps. For 1:3 Casein:DDSA a 400 g/l solution which originally contains only 100 g/l of casein gives a viscosity of 95 cps or cP. Finally, a 133 g/l solution of 3:1 Casein:DDSA which originally contained 100 g/l casein gives a viscosity of 450 cps. It is not only the amount of casein originally present before the reaction with DDSA that determines the viscosity but rather more complex interactions, probably between hydrolyzed DDSA and DDSA covalently bonded to casein.

Since casein is a protein composed of peptide linkages, and DDSA when bound to casein is also linked by an amide linkage, one would expect Casein:DDSA derivatives to be stable chemical moieties. In order to determine if they were stable, 3:1 Casein:DDSA and 1:3 Casein:DDSA were subjected to conditions of pH and temperature extremes, and then tested to determine if their cream stabilizing ability had been impaired.

TABLE 5

Effect of pH on Stability of 3:1 Casein:DDSA (Cream Stability Assay, Medium Shear)

| 1.00 ppm | Hydrocarbon | $MgSO_4$ 100 ppm | $MgSO_4$ 1200 ppm |
|---|---|---|---|
| pH 8.2 25° C. | Hexadecane | 0.84 | 0.86 |
| pH 1, 25° C., 24 h | Hexadecane | 0.82 | 0.86 |
| pH 14, 25° C., 24 h | Hexadecane | 0.88 | 0.86 |
| pH 1, 100° C., 1 h | Hexadecane | 0.88 | 0.86 |
| pH 14, 100° C., 1 h | Hexadecane | 0.88 | 0.90 |
| pH 8.2, 25° C. | Toluene | 0.84 | 0.88 |
| pH 1, 25° C., 24 h | Toluene | 0.88 | 0.88 |
| pH 14, 25° C., 24 h | Toluene | 0.86 | 0.90 |
| pH 1, 100° C. 1 h | Toluene | 0.90 | 0.90 |
| pH 14, 100° C. 1 h | Toluene | 0.70 | 0.90 |
| pH 8.2 25° C. | Hexadecane | 0.86 | 0.86 | 0.04 |
| pH 1, 25° C., 24 h | Hexadecane | 0.86 | 0.82 | 0.44 |
| pH 14, 25° C., 24 h | Hexadecane | 0.84 | 0.86 | 0.15 |
| pH 1, 100° C., 1 h | Hexadecane | 0.86 | 0.84 | 0.09 |
| pH 14, 100° C., 1 h | Hexadecane | 0.90 | 0.90 | 0.09 |
| pH 8.2, 25° C. | Toluene | 0.90 | 0.78 | 0.23 |
| pH 1, 25° C., 24 h | Toluene | 0.90 | 0.84 | 0.57 |
| pH 14, 25° C., 24 h | Toluene | 0.84 | 0.70 | 0.40 |
| pH 1, 100° C. 1 h | Toluene | 0.90 | 0.86 | 0.09 |
| pH 14, 100° C. 1 h | Toluene | 0.84 | 0.90 | 0.09 |

3:1 Casein:DDSA (4 g/L) solutions were adjusted to various pH values for different time periods and heated when necessary. After treatment the solutions were readjusted to pH 8.2 and tested.

Table 5 gives the results of these tests for 3:1 Casein:DDSA. 3:1 Casein:DDSA seems to be unaffected by exposure for 24 hours at either pH 1 or pH 14, or by exposure for 1 hour and 100° C. at pH 1 or pH 14. Table 6 gives the results of these tests for 1:3 Casein:DDSA. 1:3 Casein:DDSA seems also to be unaffected by basic conditions, but is affected by acid conditions. Its cream stabilizing ability is totally destroyed by treatment at pH 1, but it will withstand pH 3.

6.2.4 Cream Stability of Casein:DDSA at Various pH Values

In many applications the pH of the emulsion to be stabilized will not be neutral. In order to determine the effect of varying the pH of the emulsion on the cream stabilizing ability of Casein:DDSA a series of experiments were performed at various pH values with hexadecane. Table 7 gives the results of these experiments. At low pH values, no cream stabilizing ability is observed for casein, 1:3 Casein:DDSA or 3:1 Casein:D-

DSA. At higher pH values 3:1 Casein:DDSA shows its ability to stabilize hexadecane:salt water emulsions. 1:3 also stabilizes the emulsions at higher pH values, but not as well as 3:1 Casein:DDSA (1:3 works better with other hydrocarbons, toluene for example). Significantly, casein itself shows no ability to stabilize emulsions.

The fact that the Casein:DDSA does not work as well as an emulsion stabilizer at all pH values can sometimes be an advantage. For example, changing the pH of a solution can be used to break an emulsion.

6.2.5 Effect of Heating and Drying of Casein:DDSA

Several industrial applications for which Casein:DDSA is suited are cosmetics, paints, dyes or drugs. In addition, the material itself may be sterilized if necessary. In other applications where the materials must be heated during processing the material would preferably be in the form of a dry powder.

In order to determine if harsher drying conditions could be tolerated by Casein:DDSA (spray-drying or drum drying), a sample of Casein:DDSA was dried in an oven and tested for activity. Table 8 gives the results of the test, and the results are positive. No difference in cream stability can be found between Casein:DDSA materials oven dried and not dried at all.

A similar experiment was performed to determine the effect of autoclaving on Casein:DDSA. Table 9 gives the results of this experiment and again there was no effect on the Casein:DDSA.

Casein, like almost all proteins, has a definite tertiary structure. A series of experiments were performed to determine if this structure has an effect on the Casein:DDSA product obtained. Table 10 shows that denaturing the casein before reaction with DDSA produces an inferior product. It is believed that the tertiary structure of casein causes a definite substitution pattern of DDSA onto the casein molecule which in turn is probably in large part responsible for Casein:DDSA being able to stabilize emulsions. Alteration of this structure also alters its emulsification properties.

6.2.6 Enzymatic Digestion of Casein:DDSA

Casein, being a protein, is subject to enzymatic digestion by proteolytic enzymes. A series of experiments was performed to determine if Casein:DDSA was subject to enzymatic digestion. FIG. 24 shows the results of these experiments which were the expected results. Pure casein was digested to the greatest extent, then 3:1 Casein:DDSA and finally 1:3 Casein:DDSA. The most probable reason for these results (the more DDSA bound, the less enzymatic hydrolysis) is that the bound DDSA sterically hinders the hydrolytic enzyme (Maxatase).

Since proteolytic enzymes hydrolyze Casein:DDSA (See Table 11) a series of experiments was performed to determine if proteolytic enzymes could be used to break emulsions stabilized with Casein:DDSA derivatives. Emulsions of salt solutions and either hexadecane or toluene were made and maxatase was added after making the emulsions. After one hour, no difference could be observed for the maxatase treated emulsions.

A second series of experiments was performed to determine if maxatase digested Casein:DDSA derivatives would stabilize emulsions. Table 11 shows that in most cases tested they would stabilize emulsions, except for 1:3 Casein:DDSA in 100 ppm $MgSO_4$.

6.3. Effect on Concentration of Emulsion Stabilizers on Emulsion Stability

Another comparison was made to determine the various Casein-DDSA products effect on emulsion stability. 100 ppm of the material was used in the cream stability assays. FIGS. 25–29 shows the effect of increasing the concentration of 3:1 and 1:3 Casein:DDSA in the cream stability assay at various salt concentrations with either toluene, hexadecane, or diesel oil as the hydrocarbon. In some cases adding more stabilizer has almost no effect (FIG. 21) but at high salt concentrations (FIGS. 28 and 29) increasing the concentration of stabilizer increased the stability of the emulsions.

Diesel oil often behaves irregularly. FIGS. 30 and 31 show the effect on Diesel oil of varying the concentration of 3:1 and 1:3 Casein:DDSA at various salt concentrations. 3:1 Casein:DDSA with diesel oil shows expected stabilization behavior but 1:3 Casein:DDSA shows almost random behavior. In addition, 3:1 Casein:DDSA has been shown to work in stabilizing diesel-water emulsions.

TABLE 6

Effect of pH and Temperature on Stability of 3:1 Casein:DDSA (Cream Stability Assay, Medium Shear)

| Sample 1.00 ppm | Hydrocarbon | $MgSO_4$ 1200 ppm | $MgSO_4$ 1200 ppm | Instant Ocean 1200 ppm | Instant Ocean 38,000 ppm | Salt Mixture 150,000 ppm |
|---|---|---|---|---|---|---|
| pH 8.2, 25° C. | Hexadecane | 0.82 | 0.86 | 0.08 | 0.09 | 0 |
| pH 1, 25° C., 1 h | Hexadecane | 0 | 0 | 0 | 0 | 0 |
| pH 14, 25° C., 24 h | Hexadecane | 0.90 | 0.88 | 0.84 | 0.09 | 0 |
| pH 1, 100° C., 1 h | Hexadecane | 0 | 0 | 0 | 0 | 0 |
| pH 14, 100° C., 1 h | Hexadecane | 0.27 | 0.84 | 0.55 | 0.30 | 0.05 |
| pH 3, 25° C., 24 h | Hexadecane | 0.86 | 0.98 | 0.82 | 0.18 | 0 |
| pH 3, 100°, 1 h | Hexadecane | 0.90 | 0.86 | 0.86 | 0.40 | 0.05 |
| pH 8.2, 25° C. | Toluene | 0.86 | 0.84 | 0.86 | 0.09 | 0 |
| pH 1, 25° C., 1 h | Toluene | 0 | 0 | 0 | 0 | 0 |
| pH 14 25° C. 24 h | Toluene | 0.83 | 0.88 | 0.80 | 0.09 | 0 |
| pH 1, 100° C, 1 h | Toluene | 0.00 | 0.16 | 0.05 | 0.09 | 0.05 |
| pH 3, 25° C., 24 h | Toluene | 0.86 | 0.90 | 0.86 | 0.09 | 0 |
| pH 3, 100° C. 1 h | Toluene | 0.84 | 0.84 | 0.84 | 0.18 | 0 |

3:1 Casein:DDSA (4 g/L) solutions were adjusted to various pH values for different time periods and heated when necessary. After treatment the solutions were readjusted to pH 8.2 and tested.

TABLE 7

Cream Stability of Casein:DDSA at Various pH Values

| Sample 100 ppm | pH | Shear Level | $MgSO_4$ 100 ppm | Instant Ocean 1200 ppm |
|---|---|---|---|---|
| 1:3 Casein:DDSA | 4 | M | 0.0 | 0.0 |

TABLE 7-continued

Cream Stability of Casein:DDSA at Various pH Values

| Sample 100 ppm | pH | Shear Level | MgSO$_4$ 100 ppm | Instant Ocean 1200 ppm |
|---|---|---|---|---|
| 3:1 Casein:DDSA | 4 | M | 0.0 | 0.0 |
| Casein | 4 | M | 0.0 | 0.0 |
| 1:3 Casein:DDSA | 5 | M | 0.0 | 0.0 |
| 3:1 Casein:DDSA | 5 | M | 0.15 | 0.77 |
| Casein | 5 | M | 0.0 | 0.0 |
| 1:3 Casein:DDSA | 6 | M | 0.0 | 0.0 |
| 3:1 Casein:DDSA | 6 | H | 0.80 | 0.73 |
| Casein | 6 | M | 0.0 | 0.0 |
| 1:3 Casein:DDSA | 7 | H | 0.0 | 0.18 |
| 3:1 Casein:DDSA | 7 | H | 0.77 | 0.82 |
| Casein | 7 | M | 0.0 | 0.0 |
| 1:3 Casein:DDSA | 8 | H | 0.55 | 0.40 |
| 3:1 Casein:DDSA | 8 | H | 0.77 | 0.82 |
| Casein | 8 | M | 0.0 | 0.0 |
| 1:3 Casein:DDSA | 9 | M | 0.56 | 0.25 |
| 3:1 Casein:DDSA | 9 | H | 0.86 | 0.82 |
| Casein | 9 | M | 0.0 | 0.0 |
| 1:3 Casein:DDSA | 10 | M | 0.40 | 0.40 |
| 3:1 Casein:DDSA | 10 | H | 0.77 | 0.86 |
| Casein:DDSA | 10 | M | 0.0 | 0.0 |
| 1:3 Casein:DDSA | 11 | M | 0.0 | 0.0 |
| 3:1 Casein:DDSA | 11 | H | 0.60 | 0.66 |
| Casein | 11 | M | 0.0 | 0.0 |

The salt solution (100 ppm MgSO$_4$ and 1204 ppm Instant Ocean) were adjusted to pH 4-11 after the addition of the sample to be tested.

TABLE 8

Effect of Drying of Casein:DDSA Cream Stability Assay

| Sample | Shear level | 100 ppm MgSO$_4$ | 1200 ppm MgSO$_4$ | 1200 ppm Instant Ocean | 38,000 ppm Instant Ocean | 150,000 ppm Salt Mixture |
|---|---|---|---|---|---|---|
| 3:1 Casein:DDSA | M | 0.02 | 0.90 | 0.86 | 0.86 | 0.70 |
| 3:1 Casein:DDSA Oven-Dried Re-Constituted | M | 0.82 | 0.90 | 0.90 | 0.86 | 0.70 |

PROCEDURE: A 4 g/l solution of 34:1 Casein:DDSA, pH 8.2 as prepared. 20 ml was put into a vial and the remainder was put in an oven at 95° C. to dry. When all water had evaporated, a stability test was run on both the original product and on the reconstituted product at all shears, all salts, 100 ppm sample and hexadecane as oil phase.

TABLE 9

Effect of Autoclaving on Casein:DDSA Cream Stability
Cream Stability Assay (Hexadecane)

| Sample | Shear level | 100 ppm MgSO$_4$ | 1200 ppm MgSO$_4$ | 1200 ppm Instant Ocean | 38,000 ppm Instant Ocean | 150,000 ppm Salt Mixture |
|---|---|---|---|---|---|---|
| 3:1 Casein:DDSA | M | 0.84 | 0.90 | 0.86 | 0.90 | 0.30 |
| 3:1 Casein:DDSA (autoclaved) | M | 0.90 | 0.90 | 0.90 | 0.90 | 0.41 |
| 1:3 Casein:DDSA | M | 0.80 | 0.86 | 0.80 | 0.18 | 0.05 |
| 1:3 Casein:DDSA (autoclaved) | M | 0.77 | 0.84 | 0.77 | 0.18 | 0 |

PROCEDURE: 4 g/l solution of 3:1 and 1:3 Casein:DDSA were prepared. One half of each solution was autoclaved. Cream stability assay was nm at medium shear using hexadecane as oil phase.

TABLE 10

Effect of pH and Temperature on Stability of 1:3 Casein:DDSA (Cream Stability Assay, Medium Shear)

| Sample 100 ppm | Hydrocarbon | 100 ppm MgSO$_4$ | 1200 ppm MgSO$_4$ | 1200 ppm Instant Ocean | 38,000 ppm Instant Ocean | 150,000 ppm Salt Mixture |
|---|---|---|---|---|---|---|
| 3:1 Casein:DDSA | Hexadecane | .91 | .95 | .95 | .09 | .18 |
| 3:1 Casein:DDSA | Hexadecane | .86 | .95 | .73 | .09 | 0 |
| 3:1 Casein:DDSA | Toluene | .95 | 1.0 | 1.0 | .91 | .91 |
| 3:1 Casein:DDSA | Toluene | .72 | .82 | .86 | .54 | 0 |
| 3:1 Casein:DDSA | 1:1 Hexadecane 2-Methylnapthalene | .86 | .91 | .91 | .95 | .73 |
| 3:1 Casein:DDSA (100° C.) | 1:1 Hexadecane 2-Methylnapthalene | .32 | .50 | .77 | .54 | 0 |

A solution of Casein was heated to 100° C. for 1 hour and then cooled to 25° C. before reaction with DDSA at pH 8.2 and 25° C. This material is compared to Casein:DDSA made without heating the Casein first.

TABLE 11

Cream Stability of Maxatase Digested Casein
3:1 Casein:DDSA and 1:3 Casein:DDSA
(Medium Shear)

| Sample | MgSO$_4$ 100 ppm | Instant Ocean 1200 ppm |
| --- | --- | --- |
| Casein | 0 | 0 |
| Maxatase Digested Casein | 0 | 0 |
| 3:1 Casein:DDSA | 0.86 | 0.86 |
| Maxatase Digested | | |
| 3:1 Casein:DDSA | 0.84 | 0.80 |
| 1:3 Casein:DDSA | 0.90 | 0.88 |
| Maxatase Digested | | |
| 1:3 Casein:DDSA | 0.18 | 0.90 |

Casein, 3:1 Casein:DDSA and 1:3 Casein:DDSA were digested with Maxatase (1:100 (w/w, Maxatase, Sample)) at pH 9.0 until complete.

6.4. DDSA Whole-Broth Harvest Reactions

6.4.1. Overview of Reaction

Another embodiment of this invention is a method for producing novel emulsifiers and/or emulsion stabilization comprising:

(a) reacting a fermentation broth mixture with an alkyl or alkenyl succinic anhydride, and (b) separating the reacted proteins from the remaining components of the fermentation broth.

More specifically, the preferred alkenyl succinic anhydride utilized in this embodiment is DDSA. The fermentation broth can contain whole cell microorganisms, cells which have been lysed or mixtures of both. The reaction can proceed with any of these mixtures. The organisms may also be producing other products prior to the reaction, such as lipoheteropolysacharrides (e.g., emulsans), or no particular products at all. The fermentation broth is preferably an aqueous based broth.

The separation or purification of the reacted proteins is carried out according to procedures which are well known to those of ordinary skill in the art such as filtration centrifugation or decantation. The microorganisms which comprise a large portion of the fermentation broth may be of any number of varieties such as Acinetobacter, yeast or *E. coli*. The purification product may include, in addition to the reaction protein, any other product produced by the microorganism which may be simultaneously or separately isolated from the broth, such as Emulsan from fermentation broth of certain Acinetobacter species.

A preferred embodiment of this invention is demonstrated below. This example utilizes two strains of *Acinetobacter calcoaceticus* each of which produce emulsan. By way of background, the term "emulsan," which reflects the polysaccharide structure of these compounds and the exceptional bioemulsifier activity of these materials, generically identifies those extracellular microbial protein-associated polyanionic lipoheteropolysaccharides produced by *Acinetobacter calcoaceticus* ATCC 31012 and its derivatives or mutants, which may be subdivided into the alpha-emulsans and the beta-emulsans. The alpha-emulsans are the products of *Acinetobacter calcoaceticus* ATCC 31012 when grown on either ethanol or fatty acids salts as carbon source and the beta-emulsans are the products produced when the organism is grown on crude oil or hexadecane, as determined under shake flask condition.

Generally stated, the water-soluble microbial interfacially active agents for use in conjunction with the modified proteins of this invention (i.e. with DDSA) and which may be produced by a microorganism are any microbial substances which function as bioemulsifiers, i.e., substances which, by virtue of such characteristics as large molecular weight, polymeric nature, highly specific three-dimensional structure, hydrophobic and hydrophilic nature, and sparing solubilitysolubility in oil, effectively cover the oil/water interface maintaining discrete, individual oil droplets in oil-in-water emulsions thereby substantially stabilizing emulsions from coalescence. Among the preferred bioemulsifiers are lipoheteropolysaccharide biopolymers produced by bacteria of the genus Acinetobacter and in particular, those produced by strains of *Acinetobacter calcoaceticus*. Such Acinetobacter lipoheteropolysaccharide biopolymers include, but are not limited to, polyanionic lipoheteropolysaccharide biopolymers, alpha-emulsans, beta-emulsans, psi-emulsans, apo-beta-emulsans, apo-beta-emulsans, and apo-psi-emulsans produced by *Acinetobacter calcoaceticus* ATCC 31012 and described in U.S. Pat. Nos. 4,395,353; 4,395,354; 3,941,692; 4,380,504; 4,311,830; 4,311,829; and 4,311,831, respectively (hereby incorporated by reference). Such Acinetobacter biopolymers also include the biopolymers produced by *Acinetobacter calcoaceticus* BD4 [Taylor and Juni, J. Bacteriol. 81:688–693 (1961), hereby incorporated by reference], and *Acinetobacter calcoaceticus* NRRL-15616, as well as those produced by *Acinetobacter calcoaceticus*, strains NS-1 (NRRL B-15847) and NS-4 (NRRL B-15850). The foregoing "NS" strains have been deposited at the Northern Regional Research Center, Peoria, Ill. and have been assigned the foregoing NRRL accession numbers. The "NS" strains of *Acinetobacter calcoaceticus* for example strains NS-5, NS-6 and NS-7, are described by Sar and Rosenberg, Current Microbiol. 9(6):309–14 (1983), the description of which is hereby incorporated by reference. Particularly preferred Acinetobacter lipoheteropolysaccharide biopolymers are the alpha-emulsans, the production of which is further described in U.S. Pat. Nos. 4,230,801 and 4,234,689 (hereby incorporated by reference.) The alpha-emulsans are characterized by a Specific Emulsification Activity of about 200 units per milligram or higher, where one unit per milligram of Specific Emulsifications Activity is defined as that amount of emulsifying activity per milligram of bioemulsifier which yields 100 Klett absorption units using standard hydrocarbon mixture consisting of 0.1 ml of 1:1 (v/v) hexadene/2-methylnaphthalene and 7.5 ml of Tris-Magnesium buffer.

In a preferred embodiment of this invention a fermentation of the desired organism is first conducted. A heat-kill step follows at the end of the fermentation which is, in turn, followed by an "in situ" reaction with DDSA on the whole broth. This reaction is preferably run in the fermentation vessel itself. The protein "substrates" in the reaction include cell-associated proteins, "free" extra-cellular proteins and extra-cellular proteins which are "bound" to emulsan. In these reactions, the DDSA is allowed to react with whatever proteins are in the broth.

The results of three fermentations are described below. The first two fermentations (CAM 23A and CAM 23B) were conducted with Acinetobacter strain NS-4A (NRRL B-15850) grown in minimal medium with glucose as the carbon source. The third fermentation (CAM 24B) was a "typical" strain (ATCC #31012)

ethanol run. The preferred conditions of the fermentations are described in Table 12 although any fermentation broth which contains suitable nutrients to sustain growth of the particular microorganism would be acceptable in the practice of this invention.

The PET-11, NS-1, -4, -5, -6, -7 strains ave been deposited with the Agricultural Research Culture Collection (NRRL, Peoria, Ill., and have been assigned accession numbers NRRL B-15616, B-15847, B-15848, B-15849, B-15860 and B-15850, respectively. The Rag-1 strain has been deposited with the American Type Culture Collection, Rockville, Md. and has been assigned accession number ATCC 31012. Cultures of these deposited organisms are available to the public.

TABLE 12

|  | CAM 23 A & B | CAM 24B |
|---|---|---|
| Strain | NS-4 | PET-11 |
| Carbon Substrate | Glucose | Ethanol |
| total substrate fed | 85 g/l | 55 g/l |
| Minimal Medium | 2.6 g/l K$_2$HPO$_4$ | 2.6 g/l K$_2$HPO$_4$ |
|  | 1.2 g/l KH$_2$PO$_4$ | 1.2 g/l KH$_2$PO$_4$ |
|  | 5.0 g/l (NH$_4$)$_2$SO$_4$ (80 mM) | 4.0 g/l (NH$_4$)$_2$SO$_4$ (60 mM) |
|  | 0.5 g/l MgSO$_4$.7H$_2$O | 0.5 g/l MgSO$_4$.7H$_2$O |
|  | 2.5 mg/l FeSO$_4$.7H$_2$O | 2.5 mg/l FeSO$_4$.7H$_2$O |
|  | 7.0 mg/l CaSO$_4$ | 7.0 mg/l CaSO$_4$ |
| pH | 7.0 | 7.0 |
| pH Control | 6 M NaOH | 6 M NH$_4$OH/ 6M NaOH |
| Total Elapse Time | 27 hr. | 48 hr. |
| Deration | 0.5 VVM | 0.8 VVM |
| Agitation | 600–800 rpm | 600–800 rpm |
| Temperature | 30° C. | 30° C. |
| TOTAL VOLUME | 6 liter | 6 liter |

Because DDSA will react preferentially with free ammonium rather than protein amino groups, it is preferable to try to reduce the ammonium concentration at final harvest to zero o near zero. This was done by limiting the ammonia fed to the fermenters to the required amounts for cell mass and protein production.

In all three fermentation runs, no ammonia was detectable at the time of final harvest. CAM 23B and CAM 24B broths were reacted at various levels of DDSA. CAM 23 A was protease-treated at final harvest, but no other downstream reaction or product evaluation was performed with this broth.

The protocol which was followed for the downstream reaction is summarized in Table 13.

TABLE 13

|  | NS4A/glucose | | PET-EtOH |
|---|---|---|---|
|  | CAM 23a | CAM 23B | CAM 24B |
| Heat Treatment: (90° C./40 min) | pH 7.0 | pH 7.0 | pH 8.2 |
| Protease Treatment: (1 g/l Maxatase/ 45° C.-pH8- 40 min./ 65°-10 min. | yes | no | no |
| DDSA Treatment: | | | |
| Stage 1: | | | 1 part DDSA: 1 part EAU (w Maxatase Treat.) |
| DDSA added | — | 20 g/L | 21.9 g/l |
| temperature | — | 27° C. | 27° C. |
| pH | — | 8.2 | 8.2 |

TABLE 13-continued

|  | NS4A/glucose | | PET-EtOH |
|---|---|---|---|
|  | CAM 23a | CAM 23B | CAM 24B |
| base feed | — | 6M NaOH | 6M NaOH |
| TOTAL VOLUME | — | 5.0 | 5.2 |
| Stage 2: | | | 4 part DDSA: 1 part EAU (w Maxatase Treat.) (5:1 cumulative) |
| DDSA added | — | — | 87.6 g/l (109.5 g/l cumulative) |
| temperature | — | — | 27° C. |
| pH | — | — | 8.2 |
| base feed | — | — | 6M NaOH |
| TOTAL VOLUME | — | — | 3.2 L |
| Purification by Ultra-Filtration | no | yes | yes |

The following assay procedures and techniques were used to monitor the fermentations and to evaluate the downstream processes:

| Biomass: | |
|---|---|
| cell dry weight | |
| turbidity (O.D. at 660 nm) | |
| Nutrient Concentration/Consumption: | |
| glucose | hexokinase assay |
| ethanol | mass spectroscopy or enzymatic assay |
| ammonia | primol filtration or selective electrode |
| Product Formation/Recovery: | |
| emulsification activity | |
| cream stability (low shear) | |
| total protein by Biuret | |
| HPLC | |
| dry weight | (heat to constant weight) |

At most stages of the processing, a small aliquot of sample was protease-treated to determine if treatment would enhance or hurt emulsification activity. All emulsification assay results in this report, therefore, are designated as "w Maxatase" (w Max.) or "w/o Maxatase" (w/o Max.).

6.4.2 Fermentation-Cell Growth

Three fermentation runs were conducted for this example. The first two fermentations (CAM 23A and CAM 23B) were identical, each being run with Acinetobacter Strain NS-4 on glucose substrate. In the last run, strain PET-11 was grown on ethanol.

6.4.3 Heat-Kill Treatment

In all three fermentations, a heat-kill step preceded the DDSA reaction (broth was held at 90°-95° C. for 40 minutes). This step is preferred because it assures 100% destruction of viable cells prior to harvesting. It is possible, however, to kill or lyse the cells by other methods such as with sonic destruction or chemically.

The effect that this "pre-treatment" may have on the DDSA reaction could be denaturation of protein possibly affecting the quantity of protein available to react with the anhydride. However, cellular protein could be expected to be released into the broth due to lysis, thereby increasing available proteins.

Biuret protein assays were performed on broth samples at each downstream stage. Most samples showed protein concentration in the range 10–20 g/l.

6.4.4 DDSA Reaction

In CAM 23B, heat-killed whole broth was reacted with 20.0 g/l DDSA. A DDSA concentration assumed to be equivalent to the protein concentration was used (1 gram DDSA/1 gram protein).

In CAM 24B, heat-killed whole broth was reacted initially with 21.9 g/l DDSA. In this case, a DDSA concentration equivalent to the "maxatase-treated emulsification activity" was chosen (1 gram DDSA/1 EAU activity). This is roughly equivalent to the protein concentration (i.e. 1 gram DDSA/1 gram protein).

After running the CAM 24B reaction nearly to completion, an additional 87.6 g/L DDSA was added to the broth to give a cumulative 5:1 ratio with emulsification activity (5 grams DDSA/1 EAU activity).

In all cases, the pH was controlled at 8.2 with NaOH. The reactions were considered complete when base addition ceased. Reaction data for CAM 23B and 24B are recorded in Table 14. The reactions would be:

$K_2$ Reaction

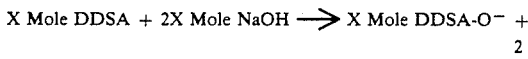
X Mole DDSA + 2X Mole NaOH → X Mole DDSA-O$^-$ + 2 H$_2$O $K_3$ Reaction
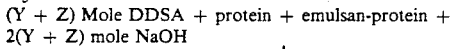
(Y + Z) Mole DDSA + protein + emulsan-protein + 2(Y + Z) mole NaOH

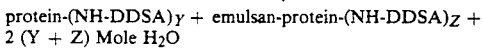
protein-(NH-DDSA)$_Y$ + emulsan-protein-(NH-DDSA)$_Z$ + 2 (Y + Z) Mole H$_2$O For both the $K_2$ and $K_3$ reactions, two moles NaOH will be required for each mole DDSA reached with protein. In order to assist driving the process toward the $K_3$ reaction, two sets of conditions had to be met:

(1) Those environmental conditions favoring the $K_3$ reaction were maintained (pH, temperature, etc.).

(2) Protein had to be present in sufficient quantity that the "molar concentration" of amino groups was greater than the molar concentration of DDSA. The protein concentration is fixed.

TABLE 14

| | | REACTION KINETICS | | |
|---|---|---|---|---|
| Rxm Time (hr.) | pH | Cumulative NaOH Fed (m Moles) | Cumulative DDSA Fed (m Moles) | Agitation Rate |
| 0 | 8.1 | 0 | 376 | 400 rpm |
| .10 | 7.9 | 105 | 375 | 400 rpm |
| .15 | 7.9 | 116 | 376 | 400 rpm |
| .25 | 7.9 | 127 | 376 | 800 rpm |
| .50 | 8.2 | 183 | 376 | 800 rpm |
| .83 | 8.1 | 266 | 376 | 600 rpm |
| .97 | 8.2 | 277 | 376 | 600 rpm |
| 1.25 | 8.1 | 327 | 376 | 600 rpm |
| 1.55 | 8.2 | 383 | 376 | 600 rpm |
| 2.12 | 8.2 | 433 | 376 | 600 rpm |
| 2.22 | 8.1 | 444 | 376 | 600 rpm |
| | | | 376 | 600 rpm |
| 0 | 8.2 | 0 | 428 | 400 rpm |
| | | | 428 | 400 rpm |
| | | | 428 | 400 rpm |
| | | | 428 | 400 rpm |
| .50 | 8.2 | 394 | 428 | 400 rpm Stage 1 |
| | | | 428 | 400 rpm (1:1) |
| 1.00 | 8.2 | 466 | 428 | 400 rpm |
| | | | 428 | 400 rpm |
| 1.50 | 8.2 | 594 | 428 | 400 rpm |

TABLE 14-continued

| | | REACTION KINETICS | | |
|---|---|---|---|---|
| Rxm Time (hr.) | pH | Cumulative NaOH Fed (m Moles) | Cumulative DDSA Fed (m Moles) | Agitation Rate |
| 2.00 | 8.2 | 687 | 428 | 400 rpm |
| 2.00 | 8.2 | 687 | 1484 | 400 rpm |
| | | | 1484 | 400 rpm Stage 2 |

6.4.5 Product Activity Enhancement

A pronounced enhancement of product performance, as measured by the emulsification activity assay, was seen following the "DDSA" reactions of both CAM 23B and CAM 24B (TABLE 15).

TABLE 15

| | Emulsification Activity (EAU/l) | | |
|---|---|---|---|
| | Final Harvest wo/ w Max. | After Heat-Kill wo/ w Max. | After DDSA wo/ w Max. |
| CAM 23B | 5.2/4.7 | 8.6/8.7 | 55.3/58.8 |
| CAM 24B (1:1) | 11.6/21.9 | 12.8/7.4 | 77.0/70.9 |
| CAM 24B (5:1) | | | 34.9/31.0 |

Three "blanks" were prepared in order to determine the "background" activity of DDSA. Hydrolyzed DDSA was diluted to a concentration of 20.0 g/L with deionized water and heat-killed CAM 23B broth respectively. DDSA-amide was also diluted to 20 g/1. Each sample was then assayed for emulsification activity.

The hydrolyzed DDSA alone had an activity equal to 1.0 EAU/1, showing that DDSA itself at that concentration has little or no "activity". When mixed with the heat-treated broth, an activity of only 4.8 EAU/1 was obtained. DDSA-amide at 20 g/1 in DI water had an activity of 1.3 EAU/1. When the heat-killed fermentation broths were reacted wtih 20 g/1 DDSA, a four to six-fold enhancement of emulsification activity was seen.

Cream stability assays were performed with the following conditions: sample concentration=100 ppm (Polymer concentration in broths assumed to be 5 g/l; 1200 ppm Instant Ocean; hexadecane and Hexadecane; low shear. Results are summarized below in Table 16.

TABLE 16

| | CREAM STABILITY | |
|---|---|---|
| | 1:1 Hexadecane 2-methylnopholene | Emulsified Oil Hexadecane |
| CAM 23B | | |
| Final Harvest | .67 | .24 |
| Heat Kill | .40 | .38 |
| 20 g/l DDSA | .16 | .17 |
| "Purified" Product | — | .10 |
| CAM 24B | | |
| Final Harvest | — | .86 |
| Heat-Kill | — | .52 |
| 1:1 DDSA Product | — | .07 |
| 5:1 DDSA Product | — | 0 |
| 1:1 DDSA "Purified" Product | — | .18 |
| 5:1 DDSA "Purified" Product | — | .78 |
| DDSA | .16 | .10 |

6.4.6 NS-4 Product Separation by Molecular Weight

In Table 15, it was seen that upon reaction with 20 g/l DDSA, emulsification activity is increased by a magnitude of four to six-fold. The role of individual components in this phenomenon of tremendously enhanced "activity" has been investigated in a limited way. Three broth components contribute to this enhanced product performance: "Emulsan", proteins, and DDSA.

Three successive ultra-filtration steps were carried out on the CAM 23B broth in order to determine whether DDSA and proteins became covalently bound during the "in situ" reaction, or whether they could still be separated back out from each other as individual components. It was also desired to determine whether or not such proteins were "bound" to Emulsan or whether they were "free" proteins.

A series of ultra-filtration steps was executed with progressively smaller pore sizes: 300,000 MW cut-off; 50,000 MW cut-off; and 10,000 MW cut-off. An Amicon stir-cell was used for this processing. The following sequence was followed with a 100 ml supernatant sample at each of the three stages of processing:
1. Final Harvest Cell-Free Broth
2. Heat-Killed Broth
3. DDSA-Reacted Broth The heat-killed step and the DDSA reaction were performed on whole broth. Only supernatants, however, were subsequently ultra-filtered. All three samples were centrifuged in a Sorvall centrifuge at 800 rpm for 15 minutes.

Four assay techniques were used to evaluate the various fractions separated in this sequential filtration process: total protein, dry weight, emulsification activity, and HPLC Assay results for these four tests are summarized in Tables 17 and 18.

Table 17 shows the absolute amount (mg or mEAU): (1) at the start of the filtration, (2-4) after each of the three filtration steps and (5) the cumulative total recovered at the end of the ultra-filtration process.

TABLE 17

Sequential Ultra-Filtration of CAM 23B Broth

| | FH | Heat-Kill | DDSA |
|---|---|---|---|
| Protein (mg) | | | |
| Total (initial) | 800 | 1350 | 1700 |
| 300,000 | 170 | 360 | 455 (1) |
| 50,000 | 137 | 161 | 207 (2) |
| 10,000 | 0 | 0 | 0 (3) |
| | 214 | 237 | 319 |
| TOTAL RECOVERED | 521 | 758 | 981 (5) |
| % RECOVERED | 65% | 56% | 58% |
| Dry Weight (mg) | | | |
| Total (initial) | 5380 | 6380 | 8220 |
| 300,000 | 1518 | 2268 | 3889 |
| 50,000 | 1026 | 564 | 963 |
| 10,000 | 0 | 0 | 0 |
| | 1360 | 979 | 1760 |
| TOTAL RECOVERED | 3904 | 3811 | 6612 |
| % RECOVERED | 73% | 60% | 80% |
| "Activity" w Max. (m EAU) | | | |
| Total (initial) | 470 | 870 | 5880 |
| 300,000 | 192 | 720 | 3318 |
| 50,000 | 0 | 14 | 282 |
| 10,000 | 0 | 0 | 0 |
| | 3 | 0 | 97 |
| TOTAL RECOVERED | 195 | 734 | 3697 |
| % RECOVERED | 41% | 84% | 63% |
| HPLC (mg) | | | |
| Total (initial) | 46 | 125 | 368 |
| 300,000 | 32 | 80 | 292 |
| 50,000 | 1 | 1 | 6 |

TABLE 17-continued

Sequential Ultra-Filtration of CAM 23B Broth

| | FH | Heat-Kill | DDSA |
|---|---|---|---|
| 10,000 | 0 | 0 | 0 |
| | 0 | 1 | 1 |
| TOTAL RECOVERED | 33 | 82 | 299 |
| % RECOVERED | 72% | 66% | 81% |

TABLE 18

% Recovery Following Sequential Ultra-Filtration

| | FH | Heat-Kill | DDSA |
|---|---|---|---|
| Protein (%) | | | |
| 300,000 | 33 | 47 | 46 |
| 50,000 | 26 | 21 | 21 |
| 10,000 | 0 | 0 | 0 |
| | 41 | 31 | 33 |
| Dry Weight (%) | | | |
| 300,000 | 39 | 60 | 59 |
| 50,000 | 26 | 15 | 15 |
| 10,000 | 0 | 0 | 0 |
| | 35 | 26 | 27 |
| "Activity" w Max. (%) | | | |
| 300,000 | 98 | 98 | 90 |
| 50,000 | 0 | 2 | 8 |
| 10,000 | 0 | 0 | 0 |
| | 2 | 0 | — |
| HPLC (%) | | | |
| 300,000 | 97 | 98 | 98 |
| 50,000 | — | — | — |
| 10,000 | 0 | 0 | 0 |
| | 0 | — | — |

Unless otherwise indicated, all assay values have been expressed as concentration per liter of the original volume of 100 ml (not the fraction volume). Looking first at the dry weight retained above the 300,000 MW cut-off filer the following profile is seen in Table 19:

TABLE 19

| | Final Harvest (F.H.) | Heat Kill (H.K.) | DDSA Treatment (DDSA) |
|---|---|---|---|
| Dry Weight | | | |
| initial sample | 53.8 g/l | 63.8 g/l | 82.2 g/l |
| 300,000 MW Retentate | 15.2 g/l | 22.7 g/l | 38.9 g/l |
| Dry Weight Increase: | | | |
| initial sample | — | 10.0 g/l+ | 18.4 g/l |
| 300,000 MW Retentate | — | 7.5 g/l+ | 16.2 g/l |

The total amount of solids in the initial sample increased 10 g/l with the heat-kill step and an additional 18.4 g/l with the DDSA treatment. The former is the result of cellular components being released into the medium as the result of lysis. The 18.4 g/l increase following DDSA addition is expected since 20.0 g/l DDSA was added after the heat-kill.

After passing the sample through the 300,000 MW cut-off filter, the dry weight increases following the heat-kill and DDSA treatment steps were 7.5 g/l and 16.2 g/l respectively. These data indicates, 88% of the DDSA added to the broth is retained above the 300,000 MW filter (16.2 g/l/18.4 g/l)..

Looking at biopolymer concentration in TABLE 20, it may be seen that for all three broths, most of the biopolymer is retained with the 300,000 MW filter (90-98%). The "activity" assay and the HPLC assay give similar results.

TABLE 20

| E.A.U./l: g/l biopolymer HPLC | | | |
|---|---|---|---|
| | F.H. | H.K. | DDSA |
| initial sample | 10.2 | 7.0 | 16.0 |
| 300,000 MW | 6.0 | 9.0 | 11.4 |
| 50,000 MW | — | * | * |
| 10,000 MW | — | — | * |

In the lower molecular weight fractions, the relationship cannot be determined, because these values fall below the sensitivity range of the HPLC assay test.

In two of the "low" molecular weight fractions, there are DDSA compounds which possess emulsification activity. The activity recovered in the 50,000 MW retentate is 2.8 g/l, and the activity recovered in the 10,000 MW permeate is 1.0 g/l. When these activity values are expressed as concentration in the actual fraction volume, they are 16.5 EAU/l and 3.5 EAU/l, respectively.

6.4.7 Product Recovery

Since the sequential filtration of CAM 23B broth showed that most emulsification activity was retained above 300,000 MW, it was preferred to process the bulk of the DDSA-reacted fermentation broths according to the schematic in Table 21.

Prior to ultra-filtration, all broths were centrifuged in the Sorvall. Since much non-active material flocculated following the DDSA reaction, simple decantation would also be feasible.

Decantation would be a preferred method to recover product with a scale-up of the process. The DDSA treatment would make it possible to eliminate centrifugation prior to ultra-filtration in the downstream processing scheme. Typical settling rates for CAM 24B are given in Table 22.

Each of the three broths was mixed by inversion and aliquoted to 100 ml graduated cylinders (100 ml per graduated cylinder). At each time interval, the optical density of the uppermost 5% (i.e. 5 ml) was measured on a Bausch & Lomb Spec 20 spectrophotometer. At 4 hours and 24 hours, optical density was also measured at the mid-point (i.e. 50 ml graduation). All samples were at ambient temperature.

TABLE 21

| DOWNSTREAM SCHEMATIC | | |
|---|---|---|
| CAM 23B | | CAM 24B |
| heat-kill | | heat-kill |
| | | 5.2 L |
| DDSA reacted (20.0 g/l) | | DDSA reacted (21.9 g/l) |
| 5.0 L | 2.0 L | 3.2 L |
| | | DDSA reacted (87.6) g/l |
| centrifugation | centrifugation | centrifugation |
| 4.3 L | | |
| purification by ultra-filtration | purification by ultra-filtration | purification by ultra-filtration |
| concentration by ultra-filtration | concentration by ultra-filtration | concentration by ultra-filtration |

TABLE 22

| | | SETTLING RATES | | |
|---|---|---|---|---|
| | | Plain | Optical Density at 660 nm | |
| | Incubation Time | Whole Broth | Heat-Treated Whole Broth | DDSA-Treated Whole Broth |
| "TOP" | 0 minutes | 10.5 | 8.3 | 7.6 |
| | 60 minutes | 9.9 | 7.2 | 5.9 |
| | 4 hours | 3.1 | 3.7 | 1.9 |
| | 24 hours | 1.4 | 6.1 | 1.2 |
| MID-POINT | 0 hours | 10.5 | 8.3 | 7.6 |
| | 4 hours | 8.4 | 7.3 | 6.2 |
| | 24 hours | 13.6 | 8.0 | 1.3 |

Addition of $Na_2$ EDTA to the 1:1 DDSA-reacted whole broth from CAM 24B was found to cause the broth to become even "clearer" and appeared to enhance flocculation. The floc was found to be non-active; that is, no "emulsification activity" was lost from the supernatant.

Ultra-filtration steps were performed at 4° C. with a one square foot Amicon hollow-fiber with a 100,000 MW cut-off. The broth was first concentrated, and then the retentate was washed with approximately 10 volumes of deionized water and concentrated again.

Downstream product recovery is summarized in Tables 23 and 24. Cumulative dry weight removed from the three broths from CAM 23B, CAM 24B (1:1), and CAM 24B (5:1) were 79%, 62% and 90% respectively. The total dry weights retained above 100,000 MW were 12.8 g/l, 13.0 g/l, and 9.7 g/l respectively.

Emulsification activity (w Max.) retained above 100,000 MW for CAM 23B, CAM 24B (1:1), and CAM 24B (5:1) were 42%, 78%, and 33% respectively. Total activity retained above 100,000 MW were: 24.6 EAU/l, 55.5 EAU/l, and 10.3 EAU/l respectively. These are concentrations per liter of original volume not retentate volume.

TABLE 23

| PRODUCT RECOVERY FOLLOWING DOWNSTREAM PROCESSING | | | |
|---|---|---|---|
| Total Volume (liter) | Dry Weight (g) | Total Protein (g) | Activity (EAU) wo/w Max. |
| (CAM 23B (NS-4A/glucose) | | | |
| 5.0 | 285 | 87 | 26/23 |
| heat-kill | | | |
| 5.0 | 290 (wb) | 150 | 43/43 |
| 20 g/l DDSA | | | |
| 5.0 | 419 (wb) | 140 | 176/293 |
| centrifugation | | | |
| 4.3 | 353 (sn) | 75 | 237/252 |
| ultra-filtration Retentate | | | |
| 1.4 | 64 | 15 | 60/123 |
| 12.1 | 224 | 50 | 26/41 |
| 2.0 | 58 | 36 | 23/44 |
| heat-kill | | | |
| 2.0 | 56 | 35 | 26/35 |
| 21 g/L DDSA | | | |
| 2.0 | 93 | 27 | 154/142 |
| centrifugation | | | |
| 1.7 | 79 | 13 | 131/121 |
| ultra-filtration Retentate | | | |
| 1.1 | 26 | 11 | 110/111 |
| 10.9 | 44 | 8 | 15/29 |
| 3.2 | 92 | 45 | 37/70 |
| heat-kill | | | |
| 3.2 | 90 | 56 | 41/56 |
| 105 g/L DDSA | | | |
| 3.2 | 415 | 32 | 112/99 |
| centrifugation | | | |
| 2.8 | 363 | 20 | 98/87 |
| ultra-filtration Retentate | | | |
| 1.8 | 31 | 14 | 40/33 |

TABLE 23-continued

PRODUCT RECOVERY FOLLOWING DOWNSTREAM PROCESSING

| Total Volume (liter) | Dry Weight (g) | Total Protein (g) | Activity (EAU) wo/w Max. |
|---|---|---|---|
| 18.2 | 319 | 14 | 25/50 |

Values from Table 23 may be used to calculate specific activity (EAU/1 gram dry weight):

|  | Final Harvest | DDSA Whole Broth | Purified DDSA/Product(s) |
|---|---|---|---|
| CAM 23B | .08 | .70 | 1.92 |
| CAM 24B (1:1) | .76 | 1.53 | 4.27 |
| CAM 24B (5:1) | .75 | .24 | 1.06 |

The specific activity on CAM 24B broth is much lower for the purified 5:1 product.

TABLE 24

PRODUCT RECOVERY (%)
(Each fraction is expressed as a percentage of the whole broth concentration following the DDSA treatment)

|  | Solids | Total Protein | Emulsification Activity w Max. | Emulsification Activity w/o Max. |
|---|---|---|---|---|
| CAM 23B (20 g/l DDSA): | | | | |
| Centrifugation | 16% | 46% | 14% | 14% |
| Ultra-Filtration | 63% | 36% | 9% | 14% |
| Cumulative Removed | 79% | 82% | 23% | 28% |
| Recovered as Retentate | 18% | 11% | 22% | 42% |
| (Total Accounted For) | 97% | 93% | 45% | 70% |
| CAM 24B (21 g/l DDSA): | | | | |
| Centrifugation | 15% | 52% | 23% | 15% |
| Ultra-Filtration | 47% | 30% | 10% | 13% |
| Cumulative Removed | 62% | 82% | 33% | 28% |
| Recovered as Retentate | 28% | 12% | 71% | 78% |
| (Total Accounted For) | 90% | 94% | 104% | 106% |
| CAM 24B (105 g/l DDSA): | | | | |
| Centrifugation | 13% | 37% | 3% | 12% |
| Ultra-Filtration | 77% | 44% | 22% | 51% |
| Cumulative Removed | 90% | 81% | 35% | 63% |
| Recovered as Retentate | 7% | 44% | 36% | 33% |
| (Total Accounted For) | 97% | 125% | 71% | 96% |

TABLE 25

Summarized below are the various activity assay results which have been obtained on CAM 24B broth:

|  | 0 Day (w/o Max w/ Max) | After 1 month (w/o Max w/ Max) | After Purification |
|---|---|---|---|
| Final Harvest | 11.6/21.9 | — | — |
| Heat Kill | 12.8/17.4 | — | — |
| 1:1 DDSA | 83.8/— | 77.0/70.9 | 64.7/6 |
| 1:1 DDSA | 12.4/15.0 | 34.9/31.0 | 14.3/11.8** |

**These values are expressed as units per liter of supernatant volume.

There was no significant activity change in the 1:1 broth versus time (Table 25). With the 5:1 broth, however, the activity increased substantially. The amount of "activity" retained above 100,000 MW was 14.3/11.8 EAU/1 (w/o Max/w/Max) in the 5:1 broth. These values are roughly equal to their original values (Table 26).

TABLE 26

| Heat-Kill | 5:1 Broth | 5:1 Retentate |
|---|---|---|
| 12.8/17.4 | 12.4/15.0 | 14.3/11.8 |

In sum, the "Activity" increased at a DDSA treatment rate of 1:1. This "activity" increase at a DDSA treatment rate of 1:1 was subsequently lost after the treatment ratio was increased to 5:1. In addition, the "activity" of the 5:1 product then increased as a function of storage time.

It can be concluded that in step #1 DDSA formed covalent linkages with high molecular weight proteins, because (1) most activity was retained above 100,000 MW during the ultra-filtration, and (2) the base:DDSA ratio approached 2:1. Upon the second addition of DDSA, the activity of the "1:1 product" decreased. Some gradual association between DDSA and low molecular weight broth components began to occur upon storage. These novel compounds/complexes possess significant emulsification activity. All three fermentation broths were stored and refrigerated as whole broth for 2-3 weeks prior to the downstream process was carried out. Gradual "release" of some additional broth component(s) into the supernatant could have occurred.

Upon ultra-filtration with a 100,000 MW cut-off hollow fiber filter this new activity was not lost but passed through the membrane and was recovered in the permeate. The dry weight also shows (Table 27) that most of the DDSA ends up in the permeate:

TABLE 27

| 28.0 g/l | 1:1 DDSA | 46.5 g/l | 5:1 DDSA | 129.7 g/l |
|---|---|---|---|---|
|  | U.F. |  | U.F. |  |
| Ret. | 15.3 g/l* | Ret. | 11.1 g/l* |  |
| Perm. | 25.9 g/l* | Perm. | 125.0 g/l* |  |

*These values are expressed as units per liter of supernatant volume.

Overall, it has been found that in situ DDSA treatment of broth results in a profound enhancement of emulsification activity when the treatment rate is at a ratio of 1:1 (DDSA: total protein). The preferred DDSA treatment ratio using the emulsification assay when it is the sole criterion for evaluating product performance would be the 1:1 product (s).

6.5. Modified Fish Protein

Fishmeal (or fish protein) is an inexpensive source of chemically functional proteinaceous biopolymers. For example, menhaden meal contains 60% or more protein and sells for about 13 cents/lb. A major factor complicating the conversion of this protein source into useful industrial chemicals is its physical form: the extensive mechanical and heat treatment the fishmeal has experienced during its manufacturing process has severely denatured the fish protein and made this protein very difficult to solubilize.

This problem was solved by exposing the fishmeal to heat and chaotropic agents (urea and sodium hydroxide). After partial solubilization the fishmeal protein was reacted with DDSA. The crude reaction product was an excellent cream stabilizing agent, and the water insoluble portion of the reacted product produced strong gels with high-water binding capacity.

The applications of such hydrophobically (i.e. DDSA)-modified fish protein could be for general colloid stabilization as well as for formation of functional gels (personal/health care), wound care, enzyme support, digestible rheology control agent in feed-particles for aqua-culture, etc.).

More specifically, in carrying out an example of the DDSA-fish protein, reaction the following procedures and materials were used:

100 g Sigma fishmeal was mixed with
480 g urea,
14 g 50% NaOH, and
520 g water.

This mixture turned into a gel, indicating that solubilization took place. The mixture was heated to 90° C., and maintained at that temperature for about 30 minutes. The material became less viscous upon heating.

The mixture was cooled to room temperature, and a sample of 100 grams was removed and adjusted to pH 8.2 with 3M sulfuric acid. This sample served as a solubilized, non-reacted control.

The remainder of the mixture (about 1,000 grams) was mixed with 34 grams DDSA. The pH was maintained at 8.2 during the reaction (at room temperature) by addition of 6M NaOH. The reaction was completed after about 3 hours, and a total amount of 19 grams NaOH-solution had been added during the reaction. This crude DDSA-modified material or reacted product (still containing about 8 M urea) was evaluated by cream stabilization.

The water-insolubles of both the control and DDSA-modified product were washed exhaustively with DI water. Between each water-wash the insolubles were separated by centrifugation at 3,000×g and the spent wash-water decanted The volume of the pellets were measured to determine water-binding ability.

The cream stability data are presented in Table 28 and illustrate that while the solubilized, but unmodified control product was unable to stabilize creams under any of the test conditions, the DDSA modified product gave stable creams of toluene in brines of intermediate salinity. DDSA by itself does not stabilize creams. The DDSA-modified product was also able to stabilize emulsions/slurries of waxy residue.

The washed gels of the two products differed substantially with respect to water binding ability after centrifugation at 3,000×g. The centrifuged pellet from the control had a specific volume of 68 ml/g dry weight, while the centrifuged pellet from the DDSA-modified product had a specific volume more than twice this value; 149 ml/g dry weight. In other words, a firm gel can be produced with washed DDSA-modified product at less than 7 g/l product concentration, while almost 15 g/l of the unmodified product is required to obtain similar gel-strength.

TABLE 28

Cream Stability at Medium Shear (Centrifugation)

| | | % Cream Stability at Salinity (ppm): | | | | |
|---|---|---|---|---|---|---|
| Sample (100 ppm) | Oil Phase | MgSO4 100 | MgSO4 1,200 | Instant Ocean Salt Mixture 1,200 | 38,000 | 150,000 |
| Control | Toluene | 0 | 0 | 0 | 0 | 0 |
| Control | Hexadecane | 0 | 0 | 0 | 0 | 0 |
| DDSA-protein | Toluene | 0 | 77 | 82 | 21 | 0 |
| DDSA-protein | Hexadecane | 0 | 0 | 0 | 0 | 0 |

6.6 Comparison of Various Anhydride-Protein Reaction Products at Different Salinities—Effect on Cream Stability All of the protein-hydrophobic anhydride products described below were synthesized by procedures (mixing, temperatures, pH, time) similar to the optimum procedures for Casein-DDSA described above.

TABLE 29

REACTION PRODUCTS OF BOVINE SERUM ALBUMIN (BSA) WITH DDSA. HEXADECANE CREAM STABILITY AT LOW SHEAR.

| REACTANT RATIO BSA:DDSA (WT/WT) | HEXADECANE CREAM STABILITY IN PRESENCE OF 5000 PPM REACTION PRODUCT AND TWO DAYS AFTER EMULSIFICATION AT | |
|---|---|---|
| | 30 PPM MgSO4 | 1200 PPM MgSO4 |
| 1:1 | LOW | HIGH |
| 10:1 | LOW | MEDIUM |
| 100:1 | HIGH | MEDIUM |

Table 29 describes BSA (Bovine Serum Albumin) derivatives. This table shows that by increasing the DDSA-reactant content (while reducing protein contents) performance at higher salinity (1200 ppm) was improved over that of the lower salinity. In addition, this demonstrates a BSA-hydrophobic anhydride derivative is an effective emulsion stabilization product under certain circumstances.

TABLE 30

REACTION PRODUCTS OF CASEIN (C) OR GELATIN (G) WITH DDSA. HEXADECANE CREAM STABILITY AT LOW SHEAR.

| REACTANT RATIO | HEXADECANE CREAM STABILITY TWO DAYS AFTER EMULSIFICATION IN PRESENCE OF 5000 PPM REACTION PRODUCT AND INSTANT OCEAN AT | | | |
|---|---|---|---|---|
| C:DDSA or G:DDSA | 300 PPM | 5,000 PPM | 12,000 PPM | 38,000 PPM |
| 3:1 C:DDSA | MEDIUM | HIGH | HIGH | HIGH |
| 100:1 C:DDSA | MEDIUM | HIGH | HIGH | HIGH |
| 3:1 G:DDSA | HIGH | HIGH | HIGH | HIGH |
| 100:1 G:DDSA | LOW | LOW | LOW | LOW |

Table 30 illustrate that gelatin (a form of collagen) when reacted with DDSA is also an effective emulsion stabilizer at varying degrees of salinity.

TABLE 31

REACTION PRODUCTS OF CASEIN WITH VARIOUS HYDROPHOBIC SUCCINIC ANHYDRIDE (SA) DERIVATIVES (ALKYL AND ALKENYL DERIVATIVES). THE REACTANT RATIO WAS CONSTANT FOR ALL REACTION PRODUCTS AT 1.23 MILLLIMOLES ANHYDRIDE PER GRAM CASEIN (CORRESPONDING TO 3:1 C:DDSA. HEXADECANE CREAM STABILITY AT MEDIUM (M) AND HIGH (H) SHEAR.

| CASEIN REACTED WITH (PPM) | SHEAR LEVEL (M OR H) | HEXADECANE CREAM STABILITY IN PRESENCE OF 100 PPM REACTION PRODUCT AND MgSO4 (PPM) INSTANT OCEAN (PPM) BRINE MIX | | | | |
|---|---|---|---|---|---|---|
| | | 100 | 1,200 | 1,200 | 3,000 | 150,000 |
| n-HEXYL | M | 0.90 | 0.90 | 0.90 | 0.86 | 0.82 |
| | H | 0 | 0 | 0.82 | 0 | 0 |
| HEXENYL-SA | M | 0.88 | 0.90 | 0.90 | 0.45 | 0.55 |
| | H | 0 | 0 | 0 | 0 | 0 |
| ISO-OCTA-DECENYL-SA | M | 0.73 | 0.88 | 0.88 | 0.90 | 0.73 |
| | H | 0 | 0 | 0.80 | 0.77 | 0 |

TABLE 31-continued

REACTION PRODUCTS OF CASEIN WITH VARIOUS
HYDROPHOBIC SUCCINIC ANHYDRIDE (SA)
DERIVATIVES (ALKYL AND ALKENYL DERIVATIVES).
THE REACTANT RATIO WAS CONSTANT FOR ALL
REACTION PRODUCTS AT 1.23 MILLIMOLES
ANHYDRIDE PER GRAM CASEIN (CORRESPONDING
TO 3:1 C:DDSA. HEXADECANE CREAM STABILITY
AT MEDIUM (M) AND HIGH (H) SHEAR.

| CASEIN REACTED WITH (PPM) | SHEAR LEVEL (M OR H) | HEXADECANE CREAM STABILITY IN PRESENCE OF 100 PPM REACTION PRODUCT AND MgSO$_4$ (PPM) INSTANT OCEAN (PPM) BRINE MIX | | | | |
|---|---|---|---|---|---|---|
| | | 100 | 1,200 | 1,200 | 3,000 | 150,000 |
| ISO-HEX-ENYL-SA | M | 0.90 | 0.90 | 0.90 | 0.18 | 0.64 |
| | H | 0 | 0 | 0 | 0 | 0 |
| N-DODECYL-SA | M | 0.90 | 0.90 | 0.90 | 0.73 | 0.68 |
| | H | 0.86 | 0.90 | 0.86 | 0 | 0 |
| DODECEN-YL-SA) (DDSA) | M | 0.86 | 0.88 | 0.90 | 0.86 | 0.23 |
| | H | 0.82 | 0.82 | 0.84 | 0 | 0 |

Table 31 compares 6 reaction products of casein and various hydrophobic succinic anhydride (SA) derivatives. The longer lipid chain (iso-octadecenyl-Sa) gives better performance toward higher salinity. A similar "shift" was observed for Casein:DDSA upon increasing DDSA-contents and may reflect a requirement of higher hydrophobicity toward higher salinity.

6.7. Products Incorporating Hydrophobically Modified Protein

Protein-hydrophobic anhydride reaction products may be used as emulsifiers and emulsion stabilizers in a variety of products. These emulsion stabilizers are naturally white in color and, therefore, may be used in many applications which cannot tolerate a colored compound, such as paints, detergents, toothpaste, dyes and cosmetics. These compounds can also be used in the following applications:

Abrasives

Rapid grinding action and fast removal of cuttings can be provided, along with excellent suspension of abrasives.

Adhesives

Adhesives will pump readily and have low viscosity on application, yet have high viscosity under low-shear conditions. Water release during drying can be fast.

Agricultural

As a suspending agent for herbicides, pesticides, fertilizers, and fungicides. Due to control of drift and cling during spraying, longer contact time can be possible. An excellent stabilizer for flowable agro-chemicals.

Ceramics

Suspend ingredients in glaze and maintain viscosity. Extrusions can be lubricated and strength can be improved.

Cleaners

Promote cling to vertical surfaces for longer contact time and can make possible formulation of gel-type acid and alkali cleaners for industrial applications.

Gels

A gelling agent in explosives.

Mining

Control settling rate of ores during sedimentation, can act as a flocculant in separation processes, and can provide foam stabilization. In slurry pumping, it can give drag reduction and can also suspend-especially under low-shear conditions.

Paper

As an antimigrant in the paper industry as a rheology modifier for high-solids size press and roll coatings, wet-end formation aid, and dewatering control of air knife coatings.

Pigments

Provide suspension of slurried pigments during shipment and storage and can help control reagglomeration. Provide solids suspension in shoe polish, abrasive suspension in silver and brass polish, and emulsion stabilization in wax polish.

Textile

As a suspending agent for dye pigments, control application in space printing and acts as flow modifier during printing application.

Wallpaper

As a flow modifier and suspending agent during printing.

Welding Ends

Lubricate during extrusion and can provide additional strength.

Deodorant

As a suspending agent for liquid/aerosol.

Fire Fighting

Improve the drop pattern and the cling of the fire-fighting fluid to trees and shrubs.

Paper Sizing

Paper industry can enhance the efficiency of rosin-alum sizes, increases Mullen reading, and can improve internal water resistance.

Suspensions

Produce stable suspensions of a variety of materials.

Blasting Explosives

Assist in producing water-resistant slurries.

Various Photographic Processing

Compatible with photoprocessing solutions.

Soil Erosion

Can be employed successfully in preventing soil erosion. Used as a suspending agent and stabilizer for water-based and emulsion inks and can provide controlled penetration and water release under uniform gloss.

In Suspending Applications

For example, shampoos for suspension of anti-dandruff agents. In stabilization of emulsions, for example, hand creams, foams, wax polishes

Cosmetics

Skin-protecting cosmetics are used to prevent the skin from chapping and keep the same fresh-looking. For this purpose, there have been proposed hand creams, cold creams, vanishing creams, milky lotions, beauty washes and the like. These skin-protecting cosmetics are, in general, in the form of an emulsion or solution by emulsification or solubilization of various oil substances with surface active agents. Such oil substances include, for instance, hydrocarbons such as liquid paraffin, vaseline, paraffin wax, squalane, ceresine wax and the like; esters such as bees wax, spermaceti, carnauba wax, lanolin and synthetic esters of higher alcohols and fatty acids; alcohols such as long-chain aliphatic alcohols, lanolin alcohol and the like; and fatty acids. By the term skin-protecting composition used herein are meant all cosmetic materials for purposes of skin protection which include, for instance, hand creams, cleansing creams, milky lotions, cold creams, vanishing creams, hair creams, foundation creams, beauty washes, facial packs and the like. In addition, powdered compressed cosmetic materials have been produced by compressing and molding under elevated pressure a mixture of a major component such as talc or sericite, and a combining agent such as a paste, for instance, carboxymethyl cellulose, or an emulsifying agent, for instance, squalane or lanolin. However, these known cosmetic materials, which are usually produced by compression to such extent that applicable hardness can be obtained are liable to be easily cracked when dried or dropped by mistake while being carried with the consumer, with eventual unfitness for use.

However, the present hydrophobically modified protein compounds of this invention may be used as emulsion stabilizers in any of these cosmetic preparations. These compounds will ensure that the cosmetic preparation will retain its desired characteristics and emulsified form for a longer period of time. The cosmetic composition according to the present invention can be produced in the same manner as in the conventional cosmetics, except that the hydrophobically modified protein is added as the emulsifier or emulsion stabilizer.

FIG. 32 also illustrates that when one of the preferred embodiments of the disclosed invention, a 3:1 Casein:D-DSA reaction product is applied to a moistened skin-like surface (leather) and compared to typical moisturizers (glycerol and mucopolysaccharides) the 3:1 Casein:DDSA product demonstrated superior moisturizing (water retention) characteristics. Therefore, the protein-lipid compounds of the present invention also have cosmetic utility as a moisturizer apart from and in addition to their emulsification and emulsion stabilizing utility in cosmetic applications. When used as a moisturizer the protein-lipid compound may be combined with other cosmetic compounds or composition such as those listed above (i.e. oil substances, skin-protecting compositions) and may be used in a variety of forms such as creams, lotions, powder, washes and compresses.

Dentifrice

The invention also relates to a liquid or pasty dentifrice and to a process for preparing such a liquid or pasty dentifice. More specifically, the invention provides a liquid or pasty dentifice uniformly incorporated therein a hydrophobically modified protein compound. Such liquid or pasty dentrifice has improved properties compared with the conventional liquid or pasty dentifice.

Paint

The invention also relates to water base and oil base paints and more particularly to dripless water base paints having a hydrophobically modified protein compound added as an emulsion stabilizer.

In general, water base paints are polymeric resin emulsions resulting from the polymerization of monomers. Such paints contain a pigment and may also contain other ingredients such as extenders; anti-foaming agents; dispersion agents; freeze-thaw stabilizers; thickeners; and preservatives.

In a water base paint, water takes the place of the thinner in the conventional oil base paint, when the paint is applied upon a surface in a thin film, the water evaporates, and the resinous or rubber-like materials form a continuous film where, by oxidation polymerization, or by coalescence of the resin particles, the film becomes water resistant. The use of the hydrophobially modified protein enables the water oil-based paint to retain its emulsion stability for longer periods of time.

The above descriptions are not meant to limit the spirit or scope of the claimed invention and or only illustrative of the variety of products where one might use a hydrophobicaly modified protein.

We claim:

1. A $C_{12}$ to $C_{30}$ alkyl- or alkenyl-succinylated emulsan in which the succinyl group is covalently attached to the protein or polypeptide of said emulsion via an amide linkage.

2. The alkyl- or alkenyl-succinylated emulsan of claim 1 in which the protein or polypeptide is a capsular polysaccharide of an *Acinetobacter calcoaceticus*.

3. The alkyl- or alkenyl-succinylated emulsan of claim 2 in which the *Acinetobacter calcoaceticus* is selected from the group consisting of RAG-1 (ATCC 31012), PET-11 (NRRL-15616), NS-1 (NRRL B-15847), NS-4 (NRRL B-15848), NS-5 (NRRL B-15849), NS-6 (NRRL B-15860) and NS-7 (NRRL B-15850).

* * * * *